US008481042B2

(12) United States Patent
Commercon et al.

(10) Patent No.: US 8,481,042 B2
(45) Date of Patent: Jul. 9, 2013

(54) CONJUGATES OF PYRROLO[1,4]BENZODIAZEPINE DIMERS AS ANTICANCER AGENTS

(75) Inventors: Alain Commercon, Vitry-sur-Seine (FR); Laurence Gauzy-Lazo, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/404,872

(22) Filed: Feb. 24, 2012

(65) Prior Publication Data

US 2012/0244172 A1    Sep. 27, 2012

Related U.S. Application Data

(63) Continuation of application No. PCT/FR2010/051709, filed on Aug. 12, 2010.

(30) Foreign Application Priority Data

Aug. 25, 2009  (FR) .................................... 09 04043
Sep. 11, 2009  (FR) .................................... 09 04368

(51) Int. Cl.
*A61K 39/44*    (2006.01)
*A61K 38/00*    (2006.01)
*A61K 31/7088*  (2006.01)
*A61K 31/5517*  (2006.01)
*A61P 35/00*    (2006.01)
*C07D 487/04*   (2006.01)
*C07H 21/00*    (2006.01)
*C07K 14/00*    (2006.01)

(52) U.S. Cl.
USPC ................... 424/181.1; 540/496; 530/391.1; 530/350; 536/23.1; 514/1.1; 514/220; 514/44 R

(58) Field of Classification Search
None
See application file for complete search history.

(56) References Cited

U.S. PATENT DOCUMENTS 7,230,101 B1    6/2007  Murthi et al.

FOREIGN PATENT DOCUMENTS

| WO | WO 00/12507      | 3/2000  |
| WO | WO 00/12508      | 3/2000  |
| WO | WO 2004/043344   | 5/2004  |
| WO | WO 2004/103272   | 12/2004 |
| WO | WO 2005/009369   | 2/2005  |
| WO | WO 2005/040170   | 5/2005  |
| WO | WO 2005/085260   | 9/2005  |
| WO | WO 2006/061258   | 6/2006  |
| WO | WO 2006/069246   | 6/2006  |
| WO | WO 2007/085930   | 8/2007  |
| WO | WO 2007085930 A1 * | 8/2007 |
| WO | WO 2007/127440   | 11/2007 |
| WO | WO 2007/144709   | 12/2007 |
| WO | WO 2008/010101   | 1/2008  |
| WO | WO 2008/047242   | 4/2008  |
| WO | WO 2009/016516   | 2/2009  |
| WO | WO 2009/026274   | 2/2009  |
| WO | WO 2009016516 A2 * | 2/2009 |

OTHER PUBLICATIONS

Cromwell et al., Protein Aggregation and Bioprocessing, AAPS Journal, 2006, 8(3), E572-E579.
Chari, Targeted Cancer Therapy: conferring specificity to cytotoxic drugs, Acc. Chem. Res., 2008, 41, 98-107.
Garnett, Targeted drug conjugates: principles and progress, Advanced Drug Delivery Reviews, 2001, 53, 171-216.
Litzen et al., Separation and Quantitation of Monoclonal antibody Aggregates by Asymmetrical Flow Filed-Flow Fractionation and comparison to Get Permeation, Analytical Biochemistry, 1993, 212(2), 469-480.
De Graaf et al., Nonnatural Amino Acids for Site-Specific Protein Conjugation, Bioconjugate Chem., 2009, 20(7)1281-1295.
Monneret et al., Ciblage de Molecules antiumoraies par les anticorps monoclonaux, Bulletin du Cancer, 2000, 87(11), 829-38.
Carter et al., Antibody-Drug Conjugatesor Cancer Therapy, Cancer J., 2008, 14(3), 154-169.
Richard et al., Internalization of a Peptide into Multilamellara Vesicles Assisted by the Formation of an alpha-Oxo Oxime Bond, Chem. Eur. J., 2005, 11(24), 7315-7321.
Kumar et al., Design, synthesis and in vitro cytotoxic studies of novel bis-pyrrolo[2,1][1,4] benzodiazepine-pyrrole and imidazole polyamide conjugates, Eur. J. Med. Chem., 2005, 40, 641-654.
Kitagawa et al., A Functional Model for the Cysteinate-Ligated Non-Heme Iron Enzyme Syperoxide reductase (SOR), J. Am. Chem. Soc., 2006, 128(45), 14448-14449.
Anderson et al., N,N'-Carbonyldiimidazole, a New Reagent for Peptide Synthesis, J. Am. Chem. Soc., 1958, 90, 4423.
Chin et al., Addition of p-Azido-L-phenylalanine to the Genetic code of *Escherichia coli*, J. Am. Chem. Soc., 2002, 124, 9026-9027.
Tozuka et al., Studies on Tomamycin. Total syntheses of the antitumor antiobiotics E- and Z-tomamycins, J. Antibiotics, 1983, XXXVI(3), 276-282.
Wang et al., Fractionation of monoclonal antibody aggregates using membrance chromatography, J. Membrane Sci., 2008, 318, 311-316.
Scrimin et al., Aggregate structure and ligand location strongly influence copper(II) binding ability of cationic metallosurfactants, J. Org. Chem., 1989, 54(25), 5988-5991.
Luening et al., Concave Pyridines and 1,10-Phenanthrolines with Sulfonamide Bridgeheads. Increased Basicity by 4-Diethylamino Substitution of the Pyridine Unit, Liebigs Ann. Chem., 1991, 10, 987-988.
Junutula et al., Site-specific conjugation of a cytotoxic drug to an antibody improves the therapeutic index, Nature Biotechnology, 2008, 26(8), 925-932.
Ricart et al., Technology Insight: cytotoxic drug immunoconjugates for cancer therapy, Nature Clinical Practice Oncology, 2007, 4(4), 245-255.

(Continued)

*Primary Examiner* — Julie Ha
*Assistant Examiner* — Erinne Dabkowski
(74) *Attorney, Agent, or Firm* — Brian R. Morrill

(57) ABSTRACT

The present invention relates to pyrrolo[1,4]benzodiazepine (PBD) dimer conjugates, to the compositions comprising them and to their therapeutic application, in particular as anticancer agents. The invention also relates to the process for the preparation of the conjugates, to their application as anticancer agents and to the dimers themselves.

13 Claims, 4 Drawing Sheets

OTHER PUBLICATIONS

International Search Report for PCT/FR2010/051709 as mailed on Jan. 12, 2011.

Wessjohann et al., 1,4-Addition of (Diphenylmethylene)amine to Acceptor Substituted Olefins. A Versatile Synthesis of Protected beta-Amino Acids, Nitriles, and Ketones, Synthesis, 1989, 5, 359-363.

Mori et al., Total Syntheses of Prothracarcin and Tomaymycin by Use of Palladium Catalyzed Carbonylation, Tetrahedron Letters, 1986, 42(14), 3793-3806.

Farmer et al., Synthesis and dna crosslinking ability of a dimeric anthramycin analog, Tetrahedron Letters, 1998, 29(40), 5105-5108.

Crisp et al., Preparation of Orthogonal pi-Conjugated Aryl Alkynes and Cyclophanes, Tetrahedron, 2000, 56(42), 8335-8344.

Singh et al., Ch. 23 Antibody-Cytotoxic Agent Conjugates: Preparation and Characterization, Therapeutic Antibodies: Methods and Protocols, 2009, vol. 525, 445-467.

Paul et al., N,N'-Carbonyldiimidazole, a New Peptide Forming Reagent, J. Am. Chem. Soc., 1960, 82, 4596-4600.

* cited by examiner

Fig.1 : Deconvoluted high resolution mass spectrum (HRMS) of the conjugate of Ex. 1 after deglycosylation
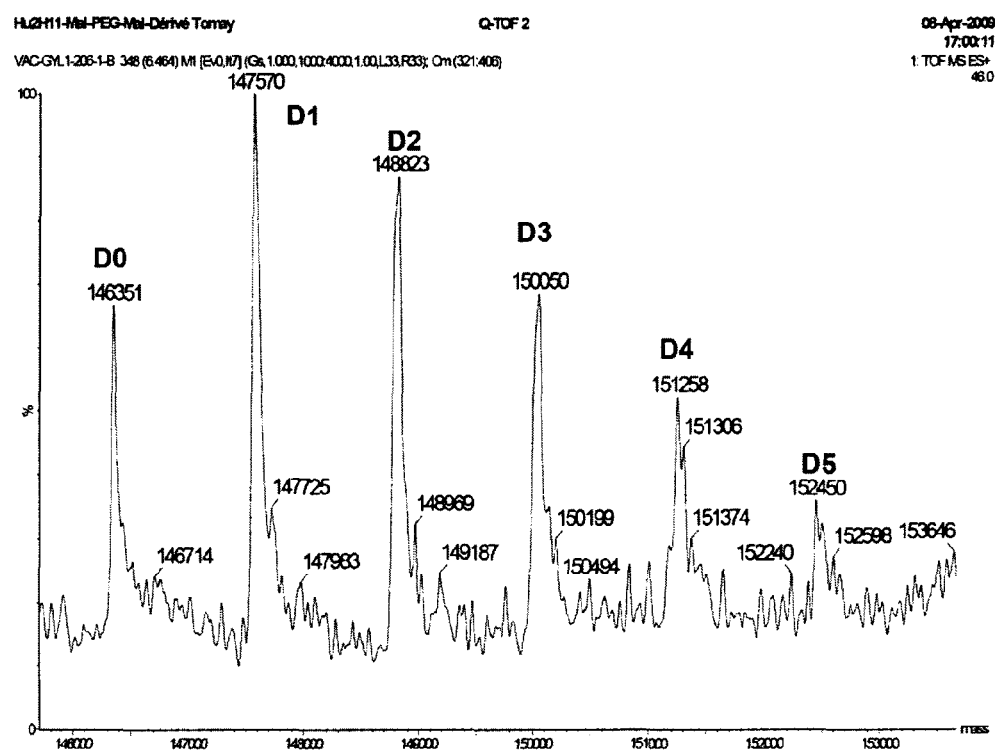

Fig.2 : Deconvoluted high resolution mass spectrum (HRMS) of the conjugate of Ex. 2 after deglycosylation
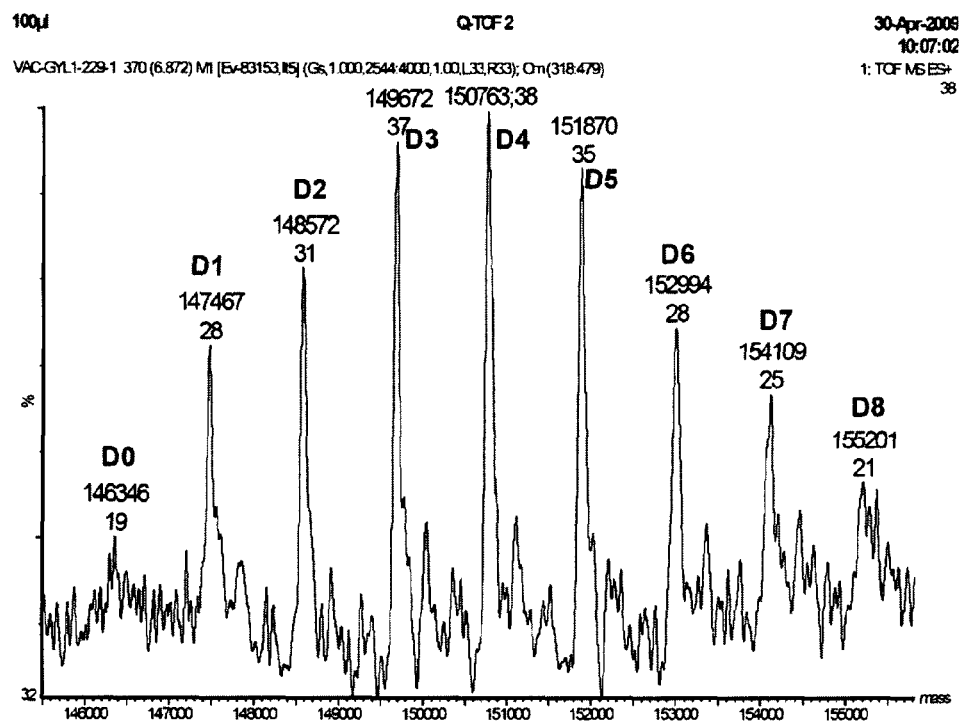

Fig.3 : Deconvoluted high resolution mass spectrum (HRMS) of the conjugate of Ex. 3 after deglycosylation
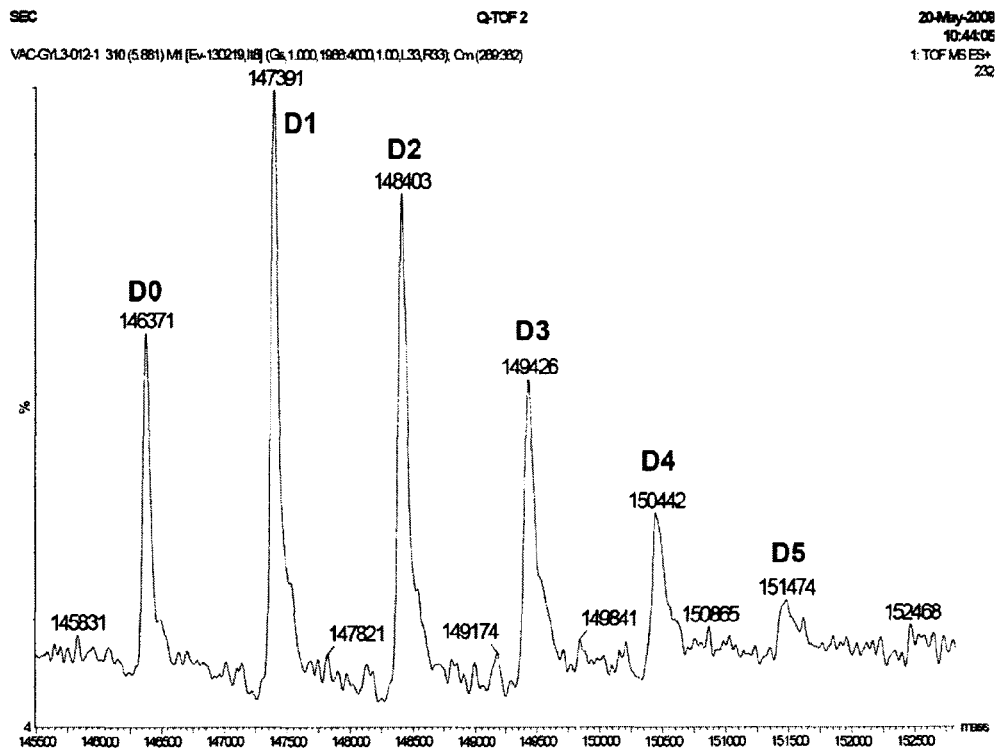
Fig.4 : Deconvoluted high resolution mass spectrum (HRMS) of the conjugate of Ex.4 after deglycosylation
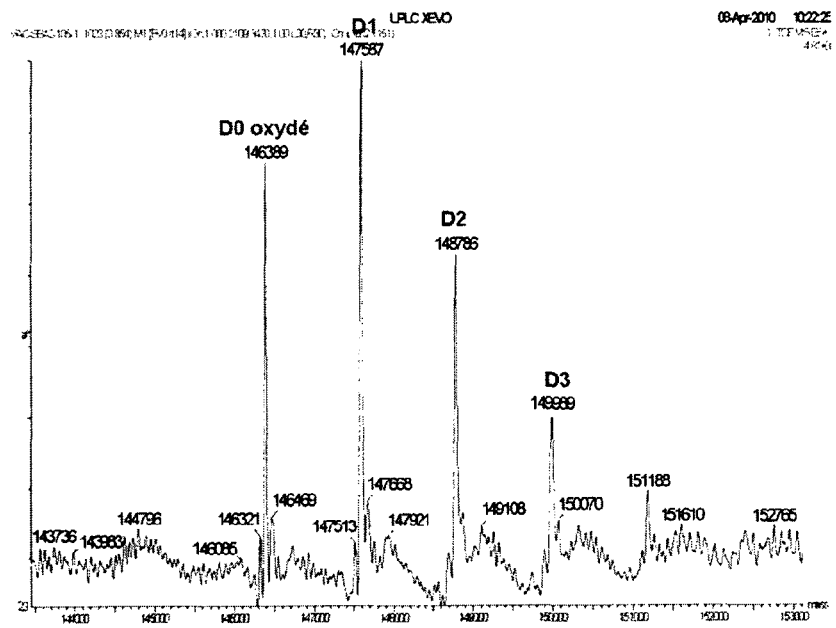

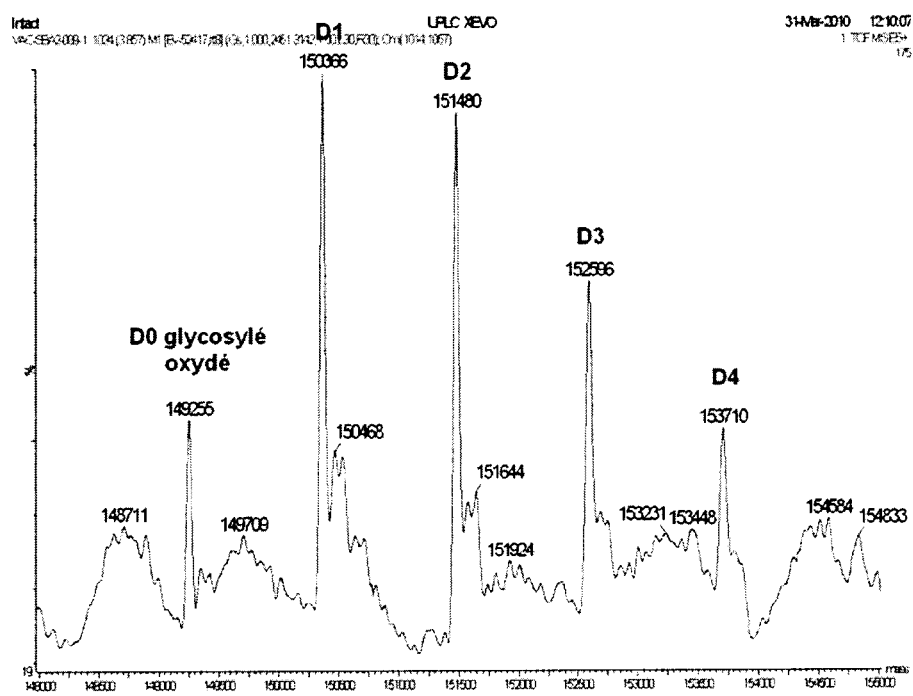
Fig.5 : Deconvoluted high resolution mass spectrum (HRMS) of the nondeglycosylated conjugate of Ex. 6

CONJUGATES OF PYRROLO[1,4]BENZODIAZEPINE DIMERS AS ANTICANCER AGENTS

The present invention relates to pyrrolo[1,4]benzodiazepine (PBD) dimer conjugates, to the compositions comprising them and to their therapeutic application, in particular as anticancer agents. The invention also relates to the process for the preparation of the conjugates, to their application as anticancer agents and to the dimers themselves.

TECHNICAL FIELD

Pyrrolo[1,4]benzodiazepine dimers are anticancer agents which act by covalently bonding to the DNA of the cells. These derivatives have been described in Applications WO 00/12508 and WO 2005/085260, and in the following publications: *Eur. J. Med. Chem.*, 2005, 40, 641-654; *Tetrahedron Letters*, 1988, 29(40), 5105-5108.

The chemistry of conjugates has been known for many years and has been applied to several families of cytotoxic agents, such as, for example, the maytansinoids (WO 04103272), the taxans (WO 06061258), the leptomycins (WO 07144709), or CC-1065 and its analogues (WO 2007102069); see also, with regard to the conjugates, Monneret C. et al., *Bulletin du Cancer*, 2000, 87(11), 829-38; Ricart A. D. et al., *Nature Clinical Practice Oncology*, 2007, 4, 245-255; Singh R. and Rickson H. K., *Therapeutic Antibodies: Methods and Protocols*, 2009, 525, 445-467.

PRIOR ART

Pyrrolo[1,4]benzodiazepine dimer conjugates have already been described in Applications WO 07085930 or WO 2009/016516. The dimers used have more particularly the formulae:

in which T can represent an aryl or heteroaryl group substituted by -G-D-$(Z)_p$—$SZ_a$ or -G-D-$(Z)_p$—C(=O)$Z_b R_b$. G represents a single or double bond or else —O—, —S— or —NR—. D represents a single bond or else one of the following groups: -E-, -E-NR—, -E-NR—F—, -E-O—, -E-O—F—, -E-NR—CO—, -E-NR—CO—F—, —CO-E-, -E-CO—F, -E-S—, -E-S—F—, -E-NR—CS—, -E-NR—CS—F—, for which E and F are chosen from —$(OCH_2CH_2)_i$alkyl$(OCH_2CH_2)_j$—, -alkyl$(OCH_2CH_2)_i$-alkyl-, $CH_2CH_2)_i$—, —$(OCH_2CH_2)_i$cycloalkyl$(OCH_2CH_2)_j$—, —$(OCH_2CH_2)_i$heterocyclyl$(OCH_2CH_2)_j$—, —$(OCH_2CH_2)_i$aryl$(OCH_2CH_2)_j$—, —$(OCH_2CH_2)_i$heteroaryl$(OCH_2CH_2)_j$—, -alkyl-$(OCH_2CH_2)_i$alkyl$(OCH_2CH_2)_j$—, -alkyl-$(OCH_2CH_2)_i$—, -alkyl-$(OCH_2CH_2)_i$cycloalkyl$(OCH_2CH_2)_j$—, -alkyl$(OCH_2CH_2)_i$heterocyclyl$(OCH_2CH_2)_j$—, -alkyl-$(OCH_2CH_2)_i$aryl$(OCH_2CH_2)_j$—, -alkyl$(OCH_2CH_2)_i$heteroaryl$(OCH_2CH_2)_j$—, -cycloalkyl-alkyl-, -alkyl-cycloalkyl-, -heterocyclyl-alkyl-, -alkyl-heterocyclyl-, -alkyl-aryl-, -aryl-alkyl-, -alkyl-heteroaryl-, -heteroaryl-alkyl-. i and j represent integers ranging from 0 to 2000. Z represents an alkyl group and p is an integer having the value 0 or 1.

The group $L_2$=—$CH_2C$(=O)$NR_3$—$(CH_2CH_2O)_i$-ALK- which characterizes some of the compounds of the present invention comprises the amide unit (—$CONR_3$—) and can correspond in WO 07085930 or in WO 2009/016516 only to the unit -E-CONR—F— with E=alkyl and F=—$(CH_2CH_2O)_i$-alkyl-. However, the group $L_1$ which is attached to the phenyl or pyridinyl ring and which is attached to $L_2$ is not described or suggested in these two patent applications. Specifically, it could correspond only to the unit G. In point of fact, G can only be a bond (single, double, triple) or else —O—, —S— or —NR—. As regards the other compounds of the present invention which are characterized by the linker —O-ALK-$NR_3$-ALK-S—$(CH_2CH_2O)_i$-ALK-, none of the units D of WO 07085930 or of WO 2009/016516 provides for the combination of an amine group $NR_3$ and of a bond —S—. The following dimers are described in WO 2009/016516:

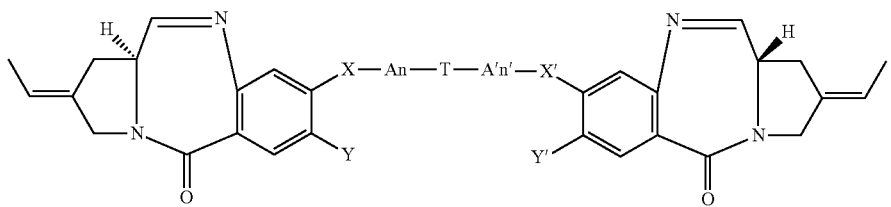

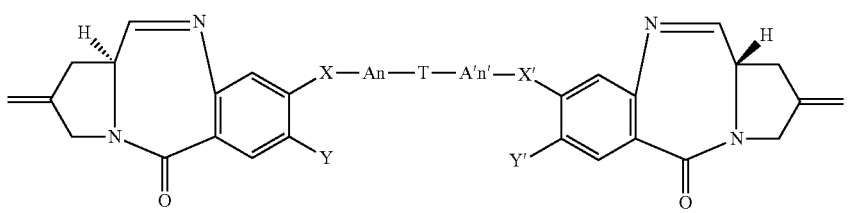

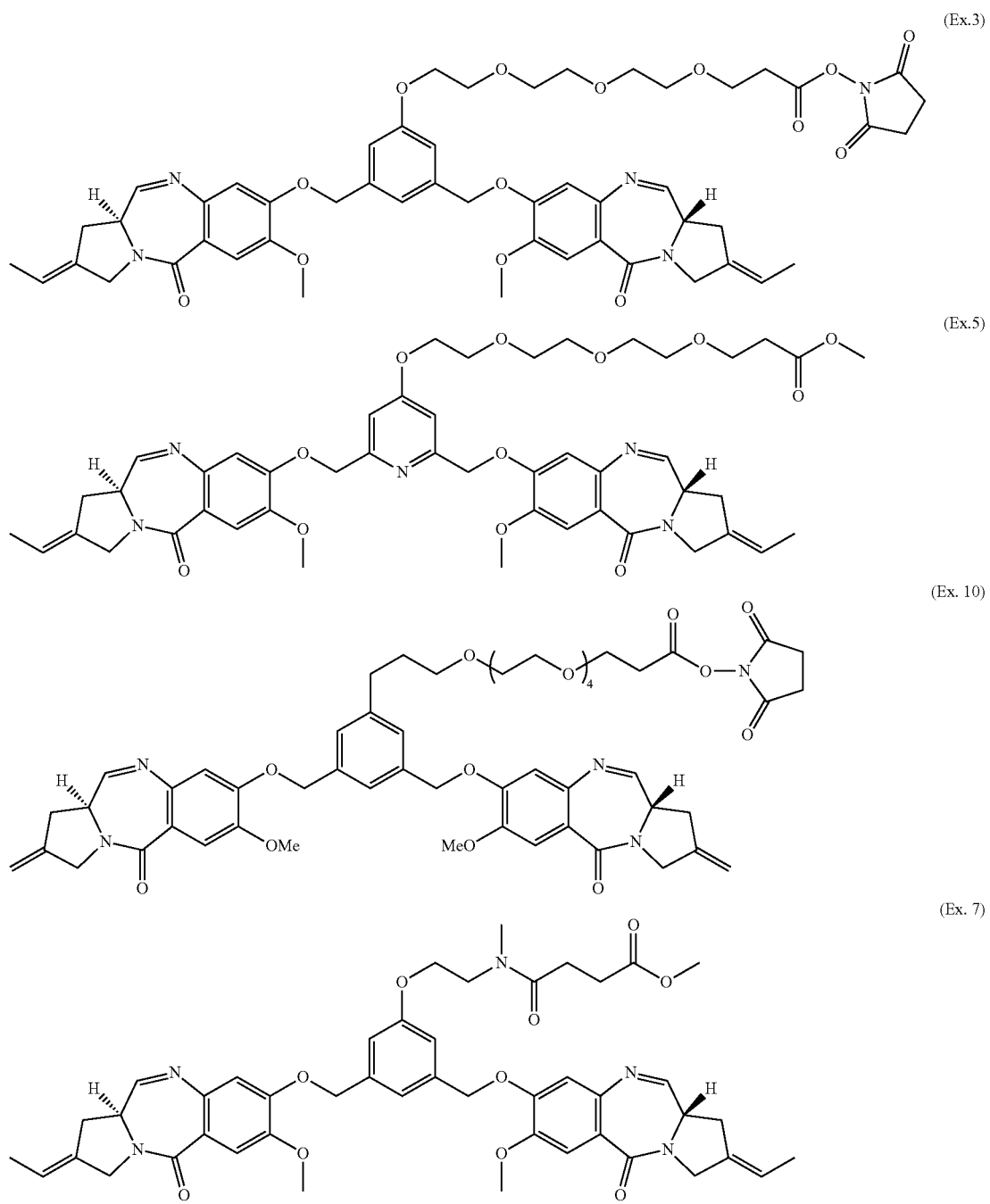

but none of these dimers comprises a linker similar to those described in the present invention (in particular, no -ALK-S— unit).

Thus, the two applications WO 07085930 and WO 2009/016516 neither describe nor suggest the compounds of the present invention.

TECHNICAL PROBLEM

The technical problem which the present invention intends to solve is that of providing novel pyrrolo[1,4]benzodiazepine dimer conjugates.

DEFINITIONS

The following terms have the accompanying meanings:
conjugate: a cell binding agent to which is covalently attached at least one molecule of a cytotoxic compound;
cell binding agent: a molecule having an affinity for a biological target: it can, for example, be a ligand, a protein, an antibody, more particularly a monoclonal antibody, a protein or antibody fragment, a peptide, an oligonucleotide or an oligosaccharide. The role of the binding agent is to direct the biologically active compound, such as a cytotoxic agent, towards the biological target;

biological target: an antigen (or group of antigens) preferentially located at the surface of the cancerous cells or stromal cells associated with this tumour; it being possible for these antigens to be, for example, a growth factor receptor, an oncogene product or mutated "tumour suppressant" gene product, an angiogenesis-related molecule or an adhesion molecule;

alkyl group: a saturated aliphatic hydrocarbon group obtained by removing a hydrogen atom from an alkane. The alkyl group can be linear or branched. Mention may be made, as examples, of the methyl, ethyl, propyl, isopropyl, butyl, isobutyl, tert-butyl, pentyl, 2,2-dimethylpropyl or hexyl groups;

cycloalkyl group: a cyclic alkyl group comprising between 3 and 8 carbon atoms involved in the cyclic structure. Mention may be made, as examples, of the cyclopropyl, cyclobutyl, cyclopentyl or cyclohexyl groups;

aryl group: a mono- or bicyclic aromatic group not comprising a heteroatom. The phenyl and naphthyl groups are more particularly concerned;

heteroaryl group: a mono- or bicyclic aromatic group comprising at least one heteroatom (O, S, N) involved in the ring and connected to the carbon atoms forming the ring. The pyridinyl, pyrrolyl, thienyl, furanyl, pyrimidinyl or triazolyl groups are more particularly concerned;

heterocycloalkyl group: a cycloalkyl group comprising at least one heteroatom (O, S, N) involved in the ring and connected to the carbon atoms forming the ring;

alkoxy group: an —O-alkyl group, where the alkyl group is as defined above;

alkanoyloxy group: an —O—CO-alkyl group, where the alkyl group is as defined above;

alkylene group: a saturated divalent group of empirical formula —$C_mH_{2m}$—, obtained by removing two hydrogen atoms from an alkane. The alkane can be linear or branched. Mention may be made, as examples, of the methylene (—$CH_2$—), ethylene (—$CH_2CH_2$—), propylene (—$CH_2CH_2CH_2$—), butylene (—$CH_2CH_2CH_2CH_2$—), isobutylene

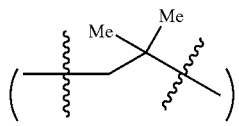

or hexylene (—$CH_2CH_2CH_2CH_2CH_2CH_2$—) groups. A linear alkylene group can more particularly be of formula —$(CH_2)_m$—, m representing an integer;

in the ranges of values, the limits are included (for example, a range of the type "i ranging from 1 to 6" includes the limits 1 and 6.

ABBREVIATIONS USED

AcOEt: ethyl acetate; ALK: ($C_1$-$C_{12}$)alkylene group, more particularly ($C_1$-$C_6$)alkylene group; TLC: thin layer chromatography; DAR: drug antibody ratio; DBU: 1,8-diazabicyclo[5.4.0]undec-7-ene; DCC: N,N'-dicyclohexylcarbodiimide; DCM: dichloromethane; DEAD: diethyl azodicarboxylate; DIC: N,N'-diisopropylcarbodiimide; DIPEA: N,N-diisopropylethylamine; DMA: dimethylacetamide; DMAP: 4-dimethylaminopyridine; DME: dimethoxyethane; DMF: dimethylformamide; DMSO: dimethyl sulphoxide; e: molar extinction coefficient; EEDQ: 2-ethoxy-1-ethoxycarbonyl-1,2-dihydroquinoline; EDCl: N-(3-dimethylaminopropyl)-N'-ethylcarbodiimide; EDTA: ethylenediaminetetraacetic acid; Fmoc: fluorenylmethoxycarbonyl; PG: protecting group; Hal: halogen atom; HOBt: 1-hydroxybenzotriazole; HEPES: 4-(2-hydroxyethyl)-1-piperazineethanesulphonic acid; LG: leaving group; NHS: N-hydroxysuccinimide; NMP: N-methylpyrrolidinone; RP: reduced pressure; Rf: retention factor; SEC: steric exclusion chromatography; AT: ambient temperature; TBDMS: tert-butyldimethylsilyl; TEA: triethylamine; TFA: trifluoroacetic acid; TIPS: triisopropylsilyl; THF: tetrahydrofuran; rt: retention time.

FIGURES

FIG. 1: high resolution mass spectrum of the conjugate of Ex. 1 after deglycosylation;

FIG. 2: high resolution mass spectrum of the conjugate of Ex. 2 after deglycosylation;

FIG. 3: high resolution mass spectrum of the conjugate of Ex. 3 after deglycosylation;

FIG. 4: high resolution mass spectrum of the conjugate of Ex. 4 after deglycosylation;

FIG. 5: high resolution mass spectrum of the non-deglycosylated conjugate of Ex. 6.

These figures show, for each conjugate after deconvolution, the distribution of the entities carrying from 0 to 8 tomaymycin dimers ($D_0$: no dimer; $D_x$: x dimers).

DESCRIPTION OF THE INVENTION

The invention relates to compounds of formula:

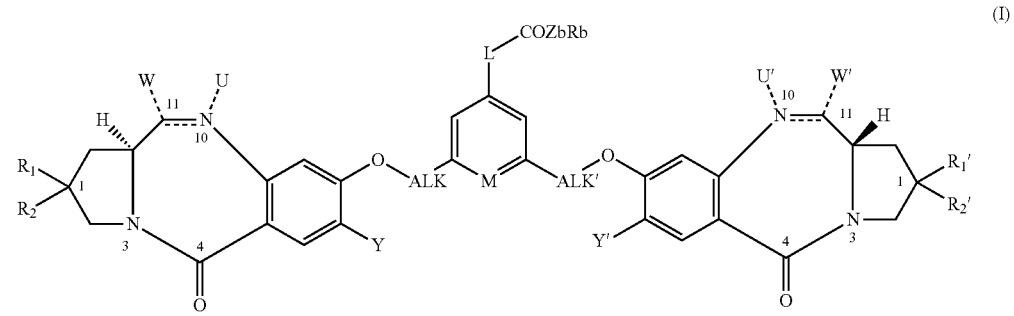

(I)

in which:
- ---- represents a single bond or a double bond with the condition that, if ---- represents a single bond, then:
- - - - represents a single bond;
- U and/or U', which are identical or different, represent(s), independently of one another, H;
- W and/or W', which are identical or different, represent(s), independently of one another: OH, —OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —SO$_3^-$, —NRSOOR', —NRR', a cyclic amine such that N10 and C11 are included in a ring, —NROR', —NRCOR', —N$_3$, —CN, Hal or a trialkylphosphonium or triarylphosphonium group;
- $R_1$, $R_2$, $R_1'$ and $R_2'$, which are identical or different, represent, independently of one another: H, Hal or a ($C_1$-$C_6$) alkyl group optionally substituted by one or more substituent(s) chosen from: Hal, CN, NRR', CF$_3$, OR, an aryl or heteroaryl group, or S(O)$_q$R with q=0, 1 or 2;
- or else
- $R_1$ and $R_2$ and/or $R_1'$ and $R_2'$ together form respectively a double bond =CH$_2$ or =CH—CH$_3$;
- Y and Y', which are identical or different, represent, independently of one another, H or OR;
- M represents CH or N;
- ALK and ALK', which are identical or different, represent, independently of one another, a ($C_1$-$C_6$)alkylene group;
- R and R' represent, independently of one another, H or a ($C_1$-$C_6$)alkyl or aryl group optionally substituted by one or more substituent(s) chosen from: Hal, CN, NRR', CF$_3$, OR or an aryl or heteroaryl group;
- L represents:
    - the -$L_1$-$L_2$- group in which $L_1$ is attached to the aromatic ring comprising M via the ALK or OALK group and represents one of the following groups:

—ALK—S—

—O—ALK—NR$_3$—S—[succinimide]—N—CH$_2$—

—O—ALK—NR$_3$—ALK—S—

—O—ALK—N[piperazine]N—C(O)—ALK—S—

—O—ALK—N[piperidine]—C(O)—ALK—S—

—O—ALK—N[piperazine]N—ALK—S— and $L_2$ represents the —CH$_2$C(=O)—NR$_3$—(CH$_2$CH$_2$O)$_i$-ALK- group attached to $L_1$ via —CH$_2$C(=O)—;

or else the —O-ALK-NR$_3$-ALK-S—(CH$_2$CH$_2$O)$_i$-ALK- group attached to the aromatic ring comprising M via the OALK group;

$R_3$ represents H or a ($C_1$-$C_6$)alkyl group;

i represents an integer ranging from 1 to 40, rather from 1 to 20, preferably from 1 to 10;

$Z_b$ represents a single bond, —O— or —NH— and $R_b$ represents H or a ($C_1$-$C_6$)alkyl, ($C_3$-$C_7$)cycloalkyl, aryl, heteroaryl or ($C_3$-$C_7$)heterocycloalkyl group or else $Z_b$ represents a single bond and $R_b$ represents Hal.

The compounds of formula (I), including those exemplified, can exist in the form of bases or of addition salts with pharmaceutically acceptable acids or also of hydrates or solvates of these bases or of these salts.

More particularly, the two ALK and ALK' groups attached to the phenyl or pyridinyl nucleus both denote a methylene group:

More particularly, among the compounds of formula (I), those of formula (IA) or (IB):

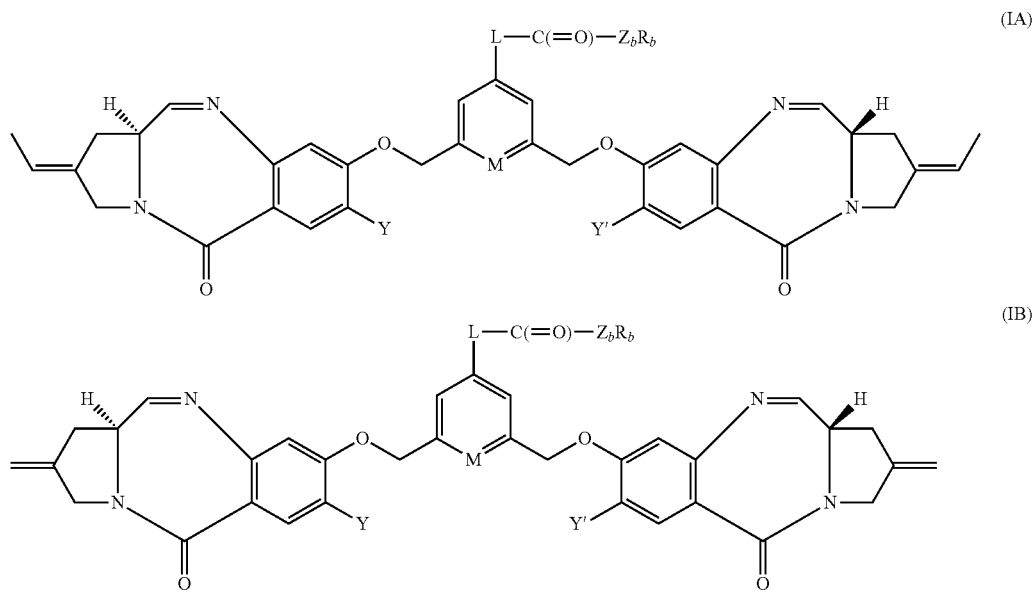

are singled out.

Y et Y' more particularly represent a $(C_1$-$C_4)$alkoxy group, in particular the methoxy group. R and R' can more particularly represent, independently of one another, H or a $(C_1$-$C_6)$ alkyl group. According to a particular form, U=U' and/or W=W and/or $R_1$=$R_1$' and/or $R_2$=$R_2$' and/or Y=Y' and/or the two ALK and ALK' groups attached to the phenyl or pyridinyl nucleus are identical.

L can more particularly be chosen from one of the following:

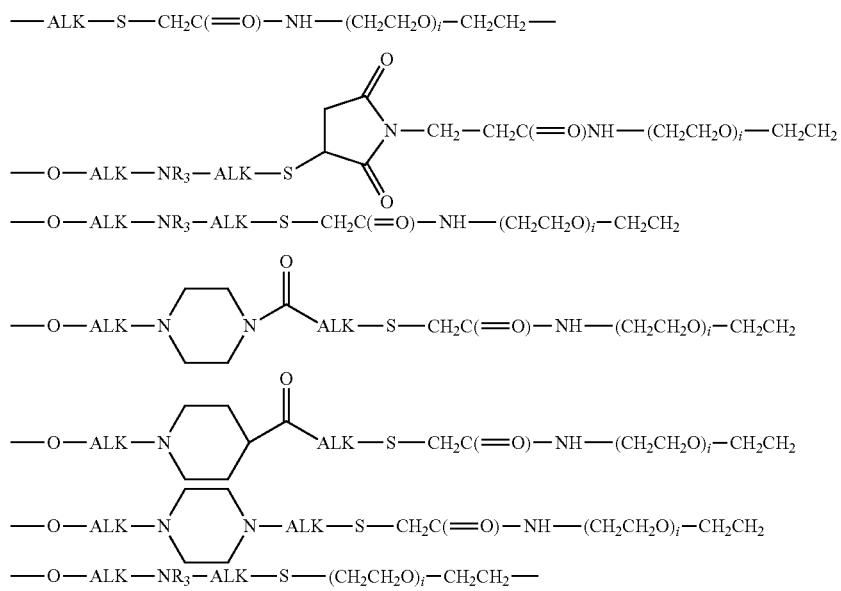

Among these, ALK more particularly represents a $(C_1$-$C_4)$ alkylene group. In particular, ALK can be one of the following: —$CH_2CH_2$—, —$CH_2CMe_2$- or —$CH_2CH_2CMe_2$-. L can also be one of those described in Table I below or in Table II.

i represents an integer ranging from 1 to 40, rather from 1 to 20, preferably from 1 to 10. i can take each of the values ranging from 1 to 40; in particular, i can have the value 3, 4, 5, 6, 7, 8, 9 or 10.

Table I describes representative examples of compounds according to the formula (IA). Each compound of this table can exist in the form with M=CH (benzene) or M=N (pyridine). The compounds with M=N are more soluble in water.

TABLE I
Compound of formula (IA)
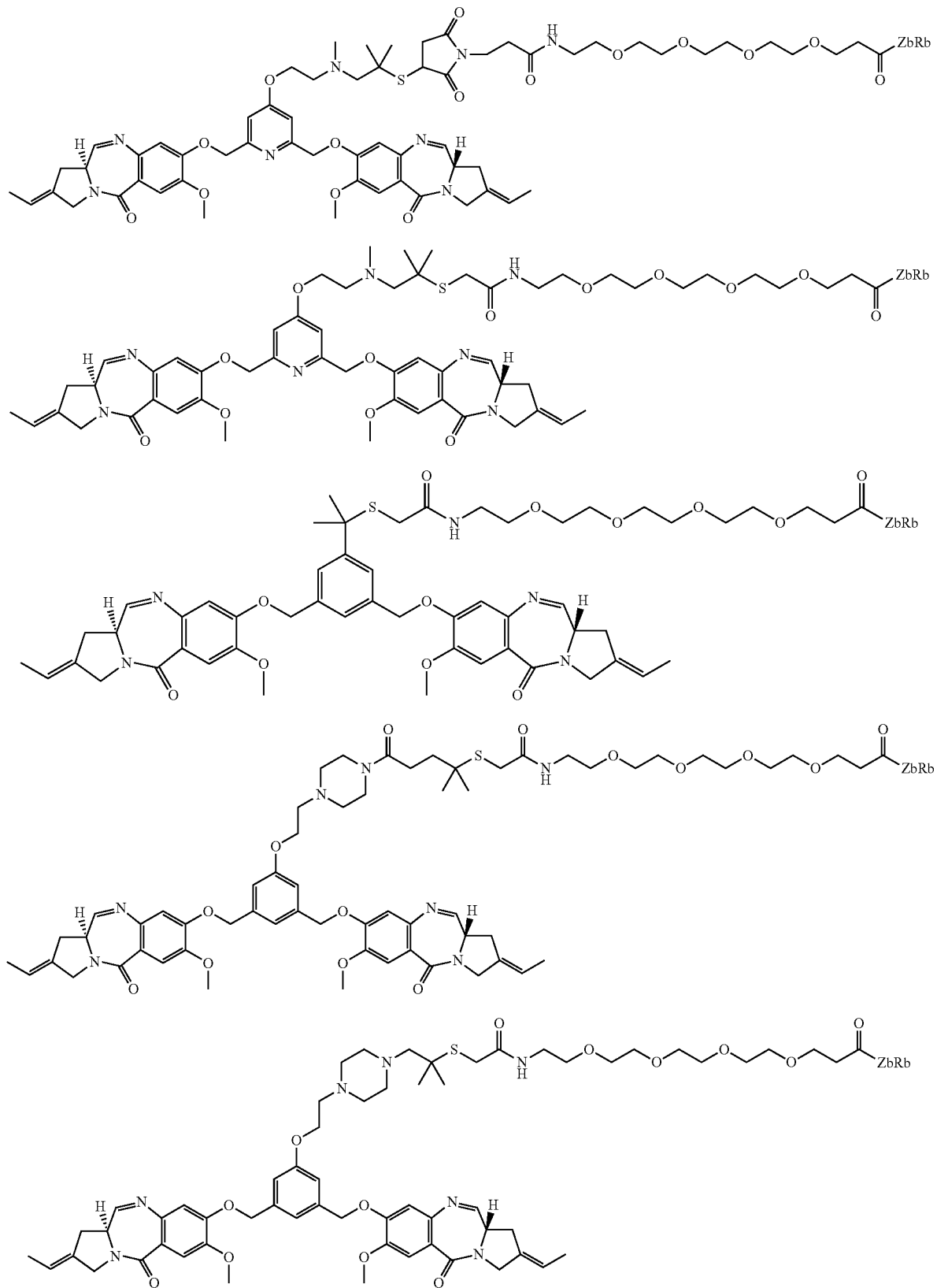

TABLE I-continued

Compound of formula (IA)

[Chemical structures showing two PBD dimer compounds with PEG linkers terminating in ZbRb groups]

The compounds according to the invention comprise the chemical group —C(=O)$Z_b R_b$ (RCG1) which is reactive with regard to a reactive chemical group (RCG2) present on the binding agent. The reaction between RCG1 and RCG2 ensures the attachment of the compound to the binding agent by formation of a covalent bond. Thus, the compound is capable of being conjugated to a binding agent. More particularly, $Z_b$ represents O; in this case, RCG1 represents an acid functional group ($R_b$=H) or an ester functional group. More particularly, —C(=O)$Z_b R_b$ represents —COOH, —COO($C_1$-$C_6$)alkyl, in particular —COOCH$_3$, or —COOCH$_2$CH=CH$_2$. Preference is given, among the ester functional groups, to the "activated" esters which exhibit a good reactivity with regard to the RCG2 groups, in particular with regard to the amino groups present on antibodies. Examples of activated esters are the following:

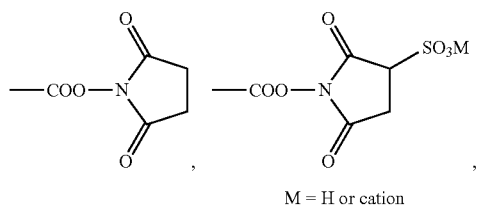

M = H or cation

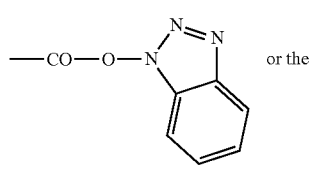 or the

-continued

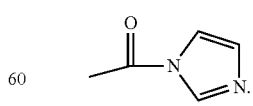

group,
in which IG represents at least one inductive group, such as —NO$_2$ or -Hal, in particular —F. The following groups may be concerned, for example:

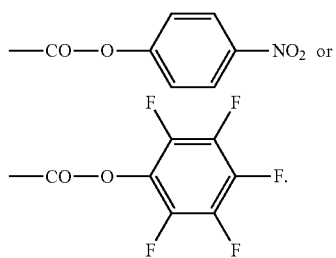

Another type of —C(=O)$Z_b R_b$ group is the following:

[imidazole carbonyl structure]

Mention may be made, as examples of RCG2, of the epsilon-amino groups of the lysines carried by the side chains of the lysine residues which are present at the surface of an antibody, the saccharide groups of the hinge region or the thiols of cysteines by reduction of intrachain disulphide bonds (Garnett M. C. et al., *Advanced Drug Delivery Reviews*, 2001, 53, 171-216). More recently, other approaches have been considered, such as the introduction of cysteins by mutation (Junutula J. R. et al., *Nature Biotechnology*, 2008, 26, 925-932; WO 09026274) or the introduction of non-natural amino acids, making possible other types of chemistry (de Graaf A. J. et al., *Bioconjugate Chem.*, 2009, Feb. 3, 2009 (Review); DOI: 10.1021/bc800294a; WO 2006/069246, and according to Chin J. W. et al., *JACS*, 2002, 124, 9026-9027 (ReCode® technology)). These methods of attachment used with the antibodies can be applied to all known binding agents according to their structure.

The compounds according to the invention can thus be used in the preparation of a binding agent to which is covalently attached, in the position para to M, the dimer of formula:

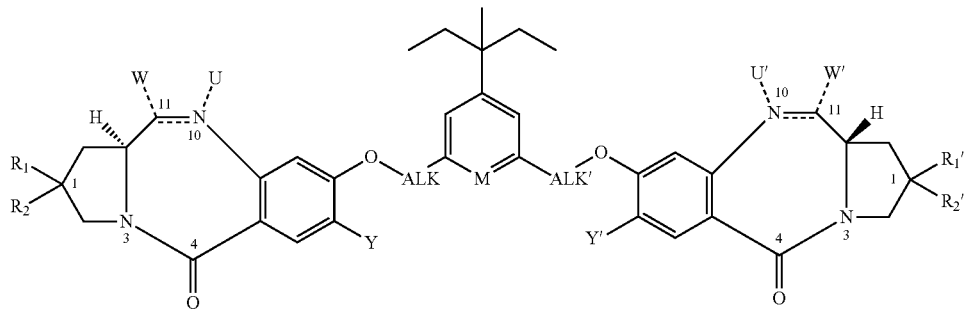

More particularly, the binding agent is an antibody. More particularly, the dimer has the formula:

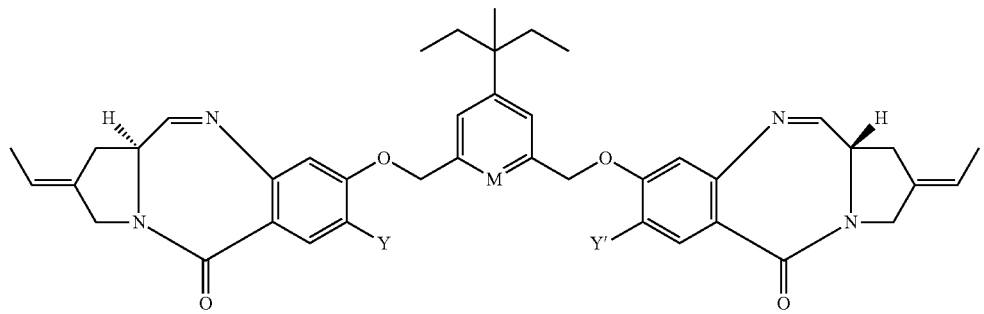

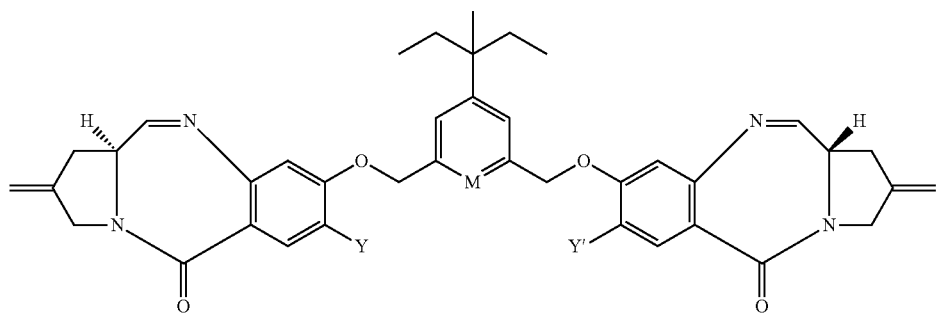

Process for the Preparation of the Compounds of Formula (I)

The compounds of formula (I) can be prepared according to Scheme 1:

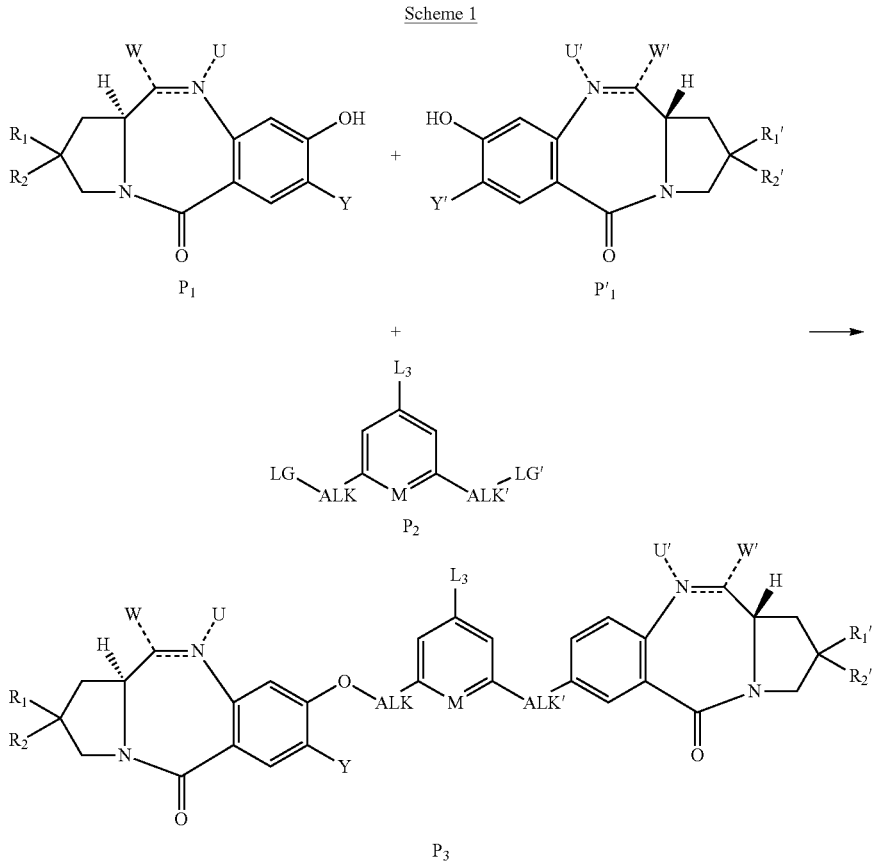

The compounds $P_1$, $P'_1$ and $P_2$ are reacted together to result in $P_3$. LG and LG' denote a leaving group. $L_3$ can represent the -L-C(=O)$Z_b R_b$ group; in this case, $P_3$ thus represents a compound of formula (I). In the case where $P_3$ does not represent the -L-C(=O)$Z_b R_b$ group, it is necessary to convert $L_3$ to the -L-C(=O)$Z_b R_b$ group using one or more reactions. In particular, in the case where —C(=O)$Z_b R_b$=

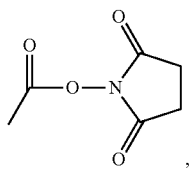

it is possible, to introduce the $L_3$ group terminated by the —C(=O)$Z_b R_b$ group=—C(=O)O—(C$_1$-C$_4$)alkyl or —C(=O)O-allyl, which is subsequently converted to the —C(=O)OH group, which finally reacts with N,N'-disuccinimidyl carbonate or NHS. The conversion of —COOalkyl/allyl to —COOH can be carried out by treatment with lithium hydroxide. It is particularly advantageous to use in particular a methyl ester. The reaction with N,N'-disuccinimidyl carbonate is carried out in the presence of a base, for example DIPEA; that with the NHS is carried out in the presence of a coupling agent, for example DCC. Likewise, in the case where —C(=O)$Z_b R_b$=

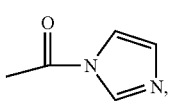

it is possible to introduce a —C(=O)$Z_b R_b$ group=—COOH which subsequently reacts with N,N'-carbonyldiimidazole (*JACS*, 1958, 80, 4423; *JACS*, 1960, 82, 4596).

The compounds $P_1$ and $P'_1$ are described in Patent Applications WO 00/12508, WO 00/12507, WO 2005/040170, WO 2005/085260, WO 07085930 or WO 2009/016516 or are accessible by total synthesis (Mori M. et al. *Tetrahedron*, 1986, 42, 3793-3806). In the case where $P_1$ and/or $P'_1$ represent(s) tomaymycin of formula:

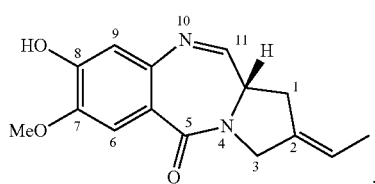

Tomaymycin the latter can be prepared using the *Streptomyces croceus* strain by following the teaching of FR 1516743 or else by total synthesis (see *J. Antibiotics*, 1983, *XXXVI*(3), 276-282, Z. Tozuka, "Studies on tomaymycin. Total syntheses of the antitumor antibiotics E- and Z-tomaymycins"). There also exist commercial $P_1/P'_1$ compounds. For the introduction of the W/W' groups, the imine functional group ($\cdots\cdots$ =double bond) is capable of adding various HW/HW' compounds (for example $H_2O$ or alcohol ROH).

With Regard to the Compounds of Formula $P_2$.

These have the formula:

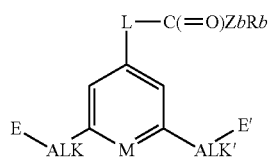

in which:

L, M, ALK, ALK', $Z_b$ and $R_b$ are as defined above;

E and E' represent, independently of one another, an —OH group or a leaving group.

L can more particularly represent one of those described in Schemes 2, 2', 3, 3', 3", 4, 5, 5', 6, 6', 6", 7.

The intermediates of formula:

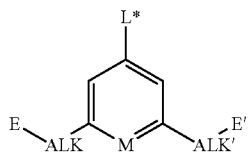

in which L* is chosen from: -ALK-SH; —O-ALK-$NR_3$-ALK-SH;

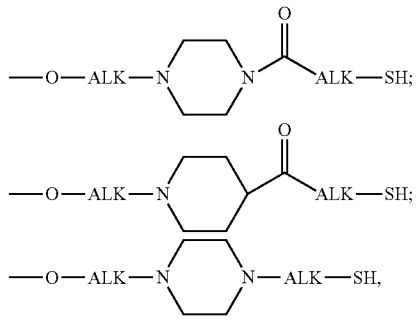

are also singled out.

In this invention, the term "leaving group" denotes an atom or a group of atoms which, in the heterolytic reaction between $P_2$ and $P_1$ or $P'_1$, leaves while carrying away the electron pair of the covalent bonds connecting ALK and LG or LG'. The leaving group is chosen more particularly from a halogen atom, in particular chlorine or bromine, or a mesylate, tosylate, nosylate or —$OPPh_3^+$ group.

For the other Schemes below, use is made, for simplicity, of the following abbreviations:

Scheme 2

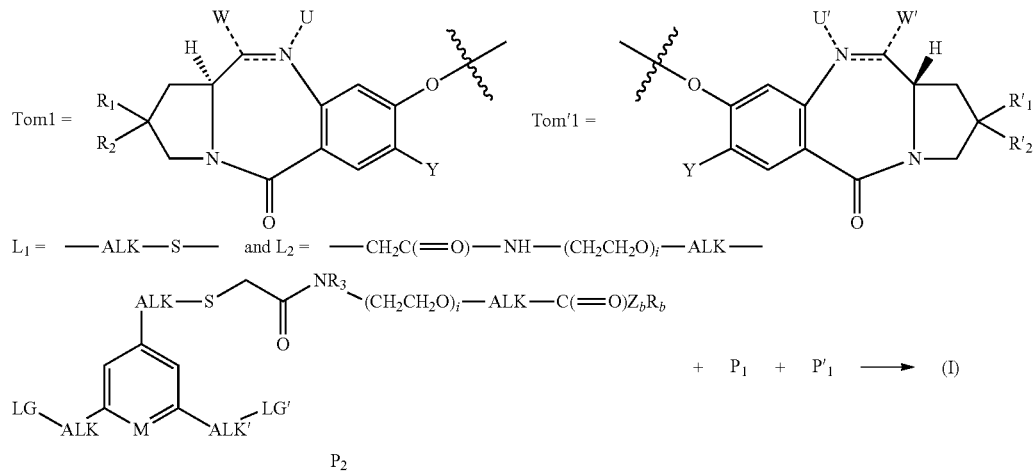

Preparation of $P_2$ $P_2$ is obtained from the corresponding halogenated diol of formula

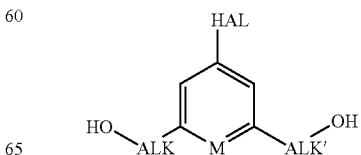

according to the teaching of Ex. 3 (Scheme 2'):

Scheme 2'
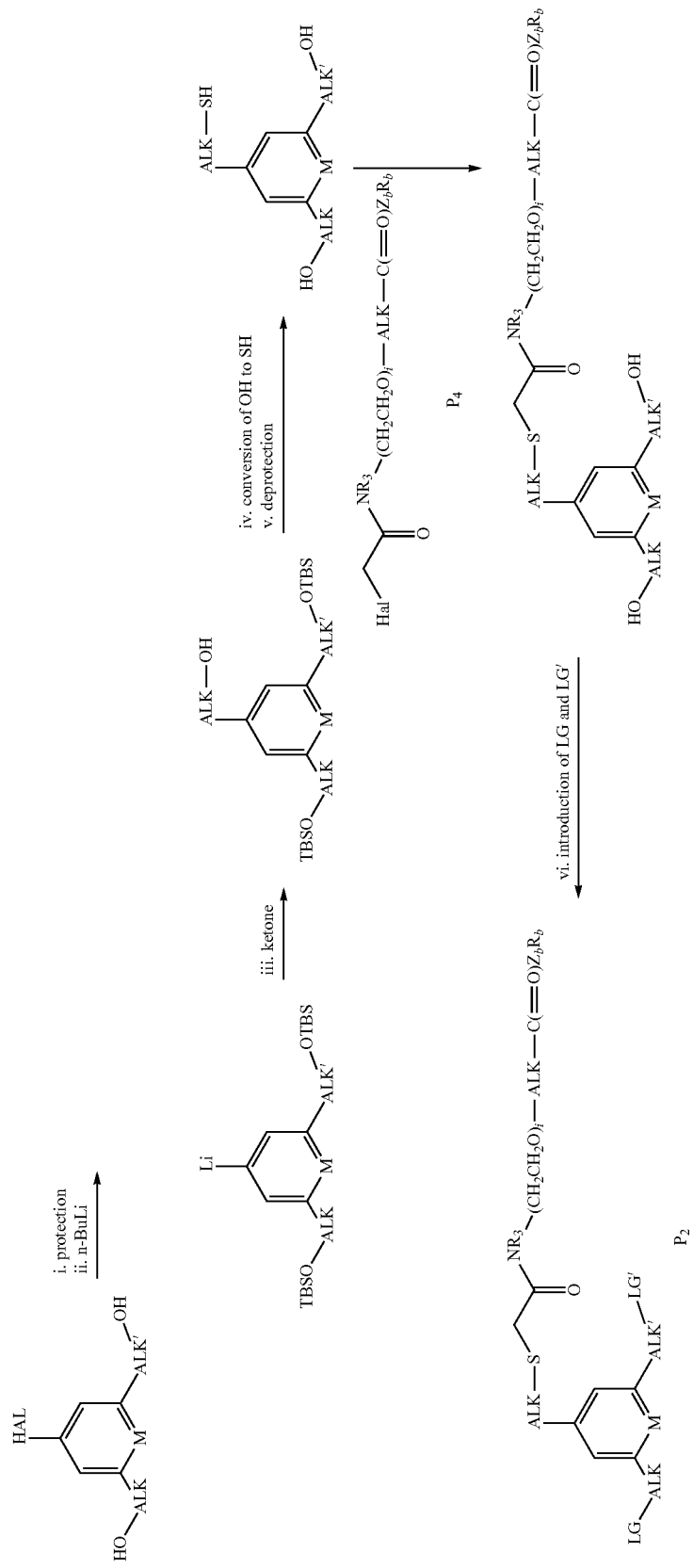

i. protection of the two alcohol functional groups using a protecting group, such as, for example, tert-butyldimethylsilyloxy (TBS);

ii. preparation of the corresponding organolithium or organomagnesium derivative using respectively n-BuLi or magnesium;

iii. nucleophilic addition to a ketone to form an alcohol functional group;

iv. preparation of the thiol via the formation of the corresponding thioacetate (see Ex. 3.7 and 3.8);

v. deprotection;

vi. introduction of LG and LG'. In the case of a mesylate group, use is made of methanesulphonyl chloride in the presence of a base, such as a tertiary amine (for example, TEA or DIPEA); see Ex. 1.4.

An example of halogenated diol and of the corresponding protected diol is that described in Scheme 1 on page 48 of WO 2009/016516 (compounds 2 and 3 of Scheme 1). Two examples of protected diols are those of CAS Nos. 181225-40-1 and 181225-41-2.

The halogenated diol can be obtained by reduction of the corresponding diacid or diester compound, for example that of CAS No. 193010-40-1. See also, in the case of a pyridine (M=N): *Liebigs Annalen der Chemie*, 1991, 10, 987-988 or *Tetrahedron*, 2005, 61(7), 1755-1763 (compound 3 of Scheme 1).

Preparation of $P_4$

Case where $ALK=CH_2CH_2$

Case where $R_3=H$

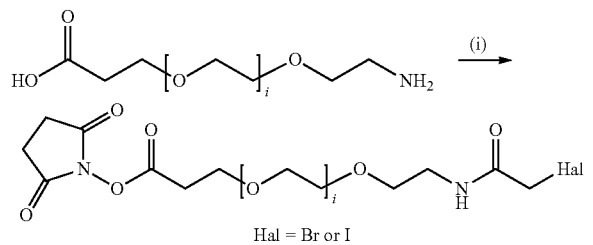

Stage (i): formation of the amide and activation of the acid; the two stages are carried out successively in a polar aprotic solvent, such as DCM: reaction between the amine functional group and N-hydroxysuccinimidyl haloacetate, followed by in situ addition of a coupling agent, such as DIC.

Case where $R_3 \neq H$

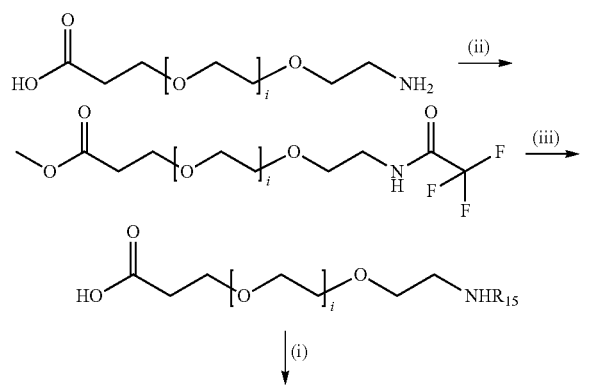

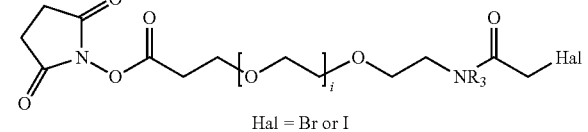

Hal = Br or I

Stage (ii): protection of the carboxylic acid in the methyl ester form and of the amine in the trifluoroacetamide form; the reaction is carried out in two successive stages in a polar aprotic solvent, such as DCM: protection of the acid by treatment with trimethylsilyldiazomethane in the presence of methanol, followed by protection of the amine by addition of trifluoroacetic anhydride and of a base, such as TEA;

Stage (iii): alkylation of the amine and saponification of the ester; the reaction is carried out in two successive stages in an anhydrous polar aprotic solvent, such as THF: alkylation of the amine by treatment with a base, such as NaH, in the presence of a reactant carrying a nucleofuge group, such as an alkyl halide $R_3Hal$, followed by addition of lithium hydroxide and of water;

Stage (i): subsequent to stage (iii), the reactions of stage (i) for the case $R_3=H$ are repeated.

Case where $ALK \neq CH_2CH_2$

Case where $R_3=H$

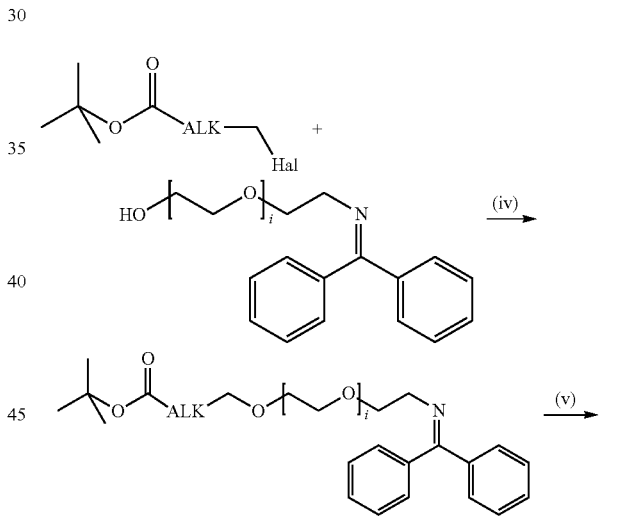

Case where $R_3 \neq H$

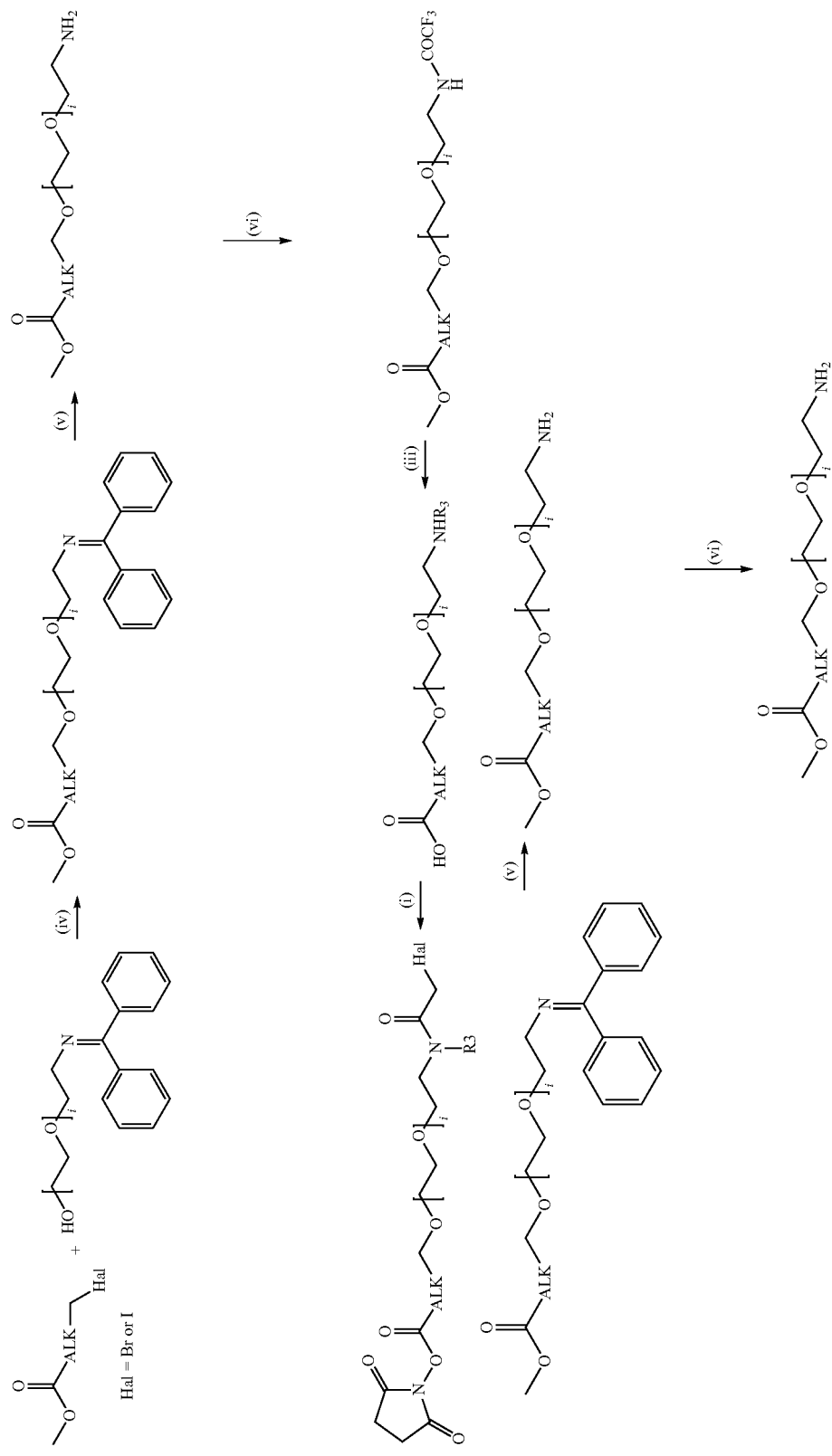

Stage (iv): elongation of the PEG chain; the reaction is carried out in an anhydrous polar aprotic solvent, such as THF or DMF, by treatment of a halogenated ester with the alkoxide of a benzophenone/imine/PEG alcohol generated by the action of NaH or of potassium naphthalenide, as described in WO 2007/127440;

Stage (v): selective cleavage of the imine by hydrogenation in the presence of palladium-on-charcoal according to Wessjohann L. et al., *Synthesis*, 1989, 5, 359-63;

Stage (vi): protection of the amine by addition of trifluoroacetic anhydride and of a base, such as TEA.

The amino/PEG alcohols are commercially available for, for example, i=3, 4, 7, 8 or can be prepared from the PEG diols, commercially available for i=3 to 12, according to the procedure described in U.S. Pat. No. 7,230,101. The protection of the amine functional group by benzophenone can be carried out by azeotropic dehydration in the presence of a Lewis acid, such as $BF_3$ etherate.

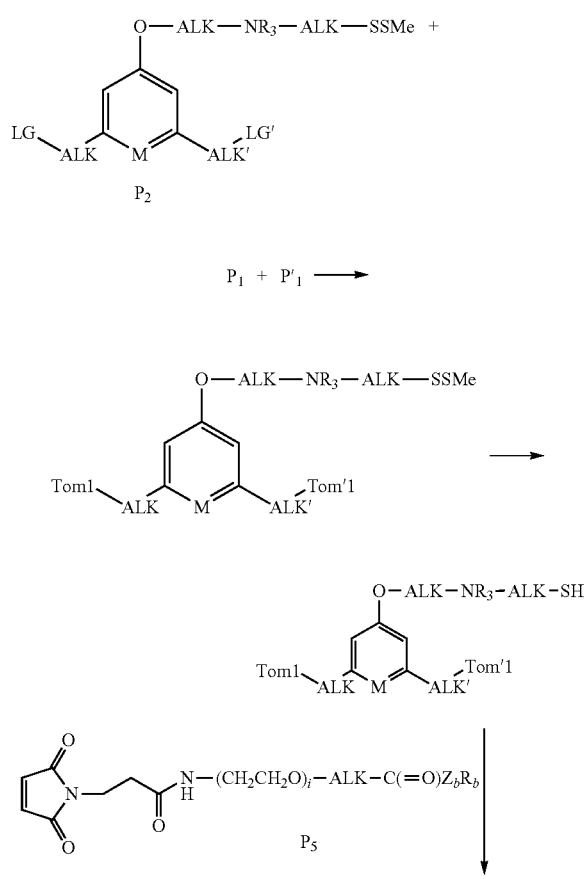

Preparation of $P_2$

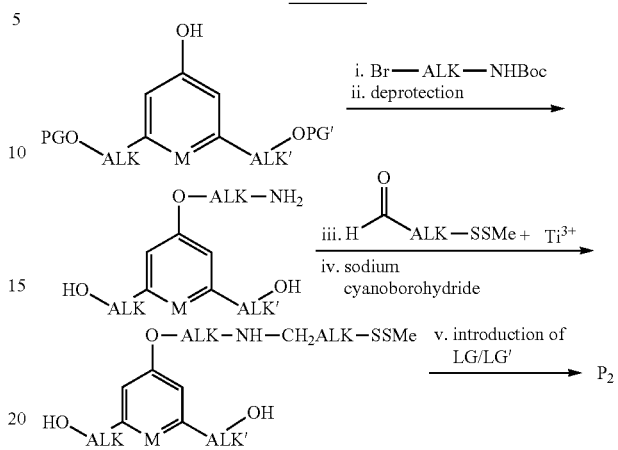

i. nucleophilic reaction between one of the —OH functional groups (the other two being protected by PG and PG', which denote protecting groups) and a bromoamine protected by Boc of formula Br-ALK-NHBoc in the presence of a base, such as, for example, $K_2CO_3$, in a polar solvent, such as DMF, THF or MeCN (see, for example, the conditions on page 63 of WO 07085930).

According to an alternative form, it is possible to carry out the nucleophilic substitution of the bromoamine by the hydroxydiester of formula:

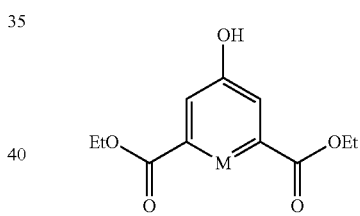

and then to subsequently reduce the ester functional group to give a —$CH_2OH$ functional group, for example with sodium borohydride; it is possible to apply, for this, the conditions of the nucleophilic substitution and of the reduction given on pages 62-63 of WO 2007/085930;

ii. deprotection of protecting groups;

iii. reductive amination with the aldehyde of formula HC(=O)-ALK-SSMe in the presence of titanium isopropoxide; the reaction is carried out at ambient temperature in an anhydrous polar aprotic solvent, such as THF;

iv. an intermediate complex is formed which is reduced in situ with a reducing agent, such as, for example, sodium cyanoborohydride;

v. introduction of LG and LG'. In the case of a mesylate group, use is made of methanesulphonyl chloride in the presence of a base, such as a tertiary amine (for example TEA); see Ex. 1.4.

An alternative form represented in Scheme 3" consists in introducing the -ALK-SSMe group onto the NHBoc group, under the inspiration in particular of the method described by Kitagawa T. et al., *JACS*, 2006, 128(45), 14448-14449, used to introduce acetylthioalkyl chains onto a secondary amine:

Scheme 3''

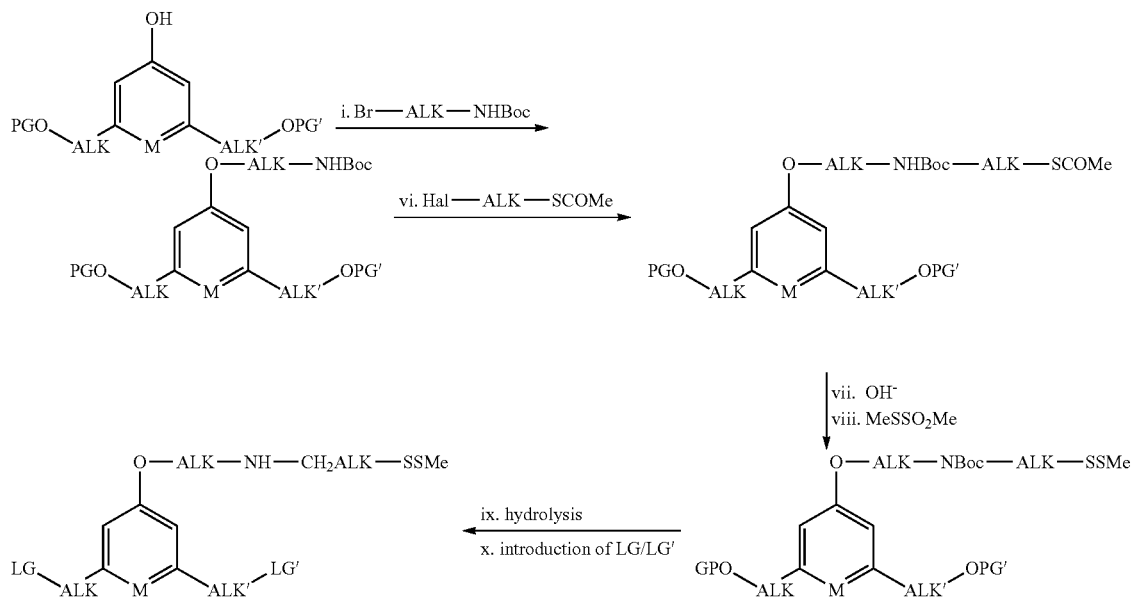

According to this alternative form, the alkylation is carried out using an intermediate Hal-ALK-SCOMe (Hal=I, for example) and then the thiol is released by a treatment in a basic medium:
- vi. alkylation by an alkyl halide carrying a thioacetyl group in the presence of caesium carbonate in a polar aprotic solvent, such as DMF;
- vii. selective cleavage of the acetyl group in a weak basic medium;
- viii. formation of the —SSMe group by reaction of the intermediate thiol with MeSSO$_2$Me;
- ix. cleavage of the protecting groups PG and PG';
- x. conversion of the hydroxyl groups to nucleofuge groups LG/LG', preferably mesylate groups.

Scheme 3'''

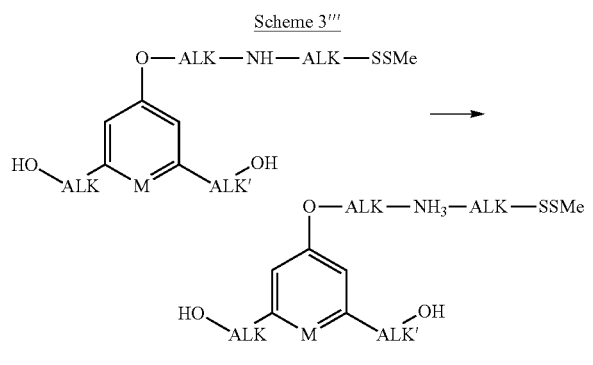

The introduction of an R$_3$ group =(C$_1$-C$_4$)alkyl onto an NH group is possible at different stages of the synthesis (an example is given in Scheme 3'''). It is carried out, for example, by employing the Wallach reaction, which uses an aldehyde (see Ex. 1.5, where the alkylation NH⇒NMe uses formaldehyde).

With Regard to P$_6$

Thermo Fisher Scientific, Rockford, Ill. 61105, USA, Jenkem Technology USA Inc., 2033 W. McDermott Dr, Allen, Tex. 75013-4675, USA, and Quanta BioDesign Ltd., 195 West Olentangy Street, Suite O, Powell, Ohio 43065-8720, USA, sell compounds of general formula

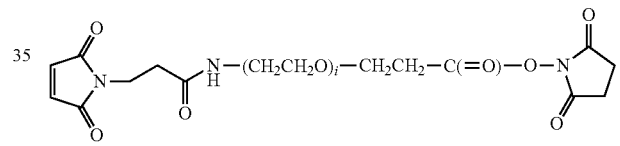

denoted by NHS-PEG-maleimide. The compound of CAS No. 756525-99-2 may more particularly be concerned.

The addition of the thiol to the maleimide unit is described on page 721 of "Bioconjugate Techniques", Greg T. Hermanson, 2nd Ed., Elsevier Inc. (ISBN-13: 978-0-12-370501-3; ISBN-10:0-12-370501-0).

Scheme 4

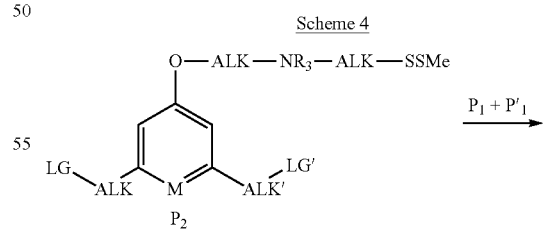

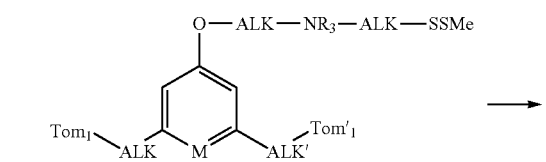

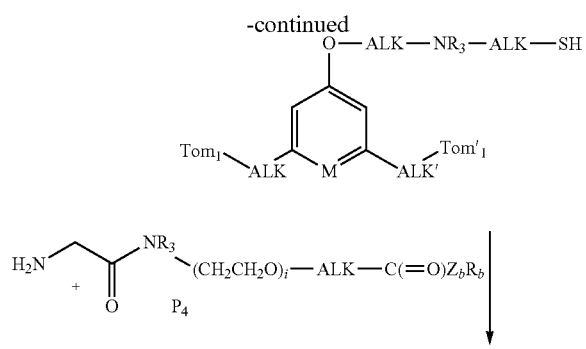

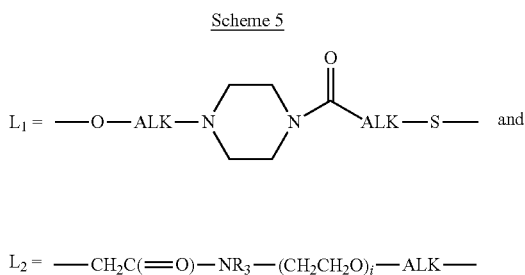

i. deprotection by reduction of the disulphide

Scheme 5

$L_1 =$ —O—ALK—N(piperazine)N—C(=O)—ALK—S— and $L_2 =$ —CH$_2$C(=O)—NR$_3$—(CH$_2$CH$_2$O)$_i$—ALK—

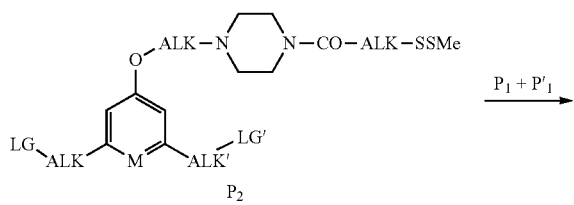

(I)

$L_1 =$ —O—ALK—NR$_3$—ALK—S— and
$L_2 =$ —CH$_2$C(=O)—NR$_3$—(CH$_2$CH$_2$O)$_i$—ALK—

The preparation is similar to that described in Scheme 3, P$_5$ being replaced by P$_4$.

An alternative form described in Scheme 4' corresponds to a preparation similar to that described in Schemes 2 and 2':

Scheme 4'

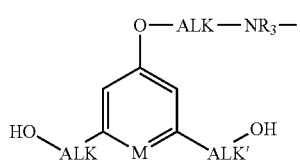

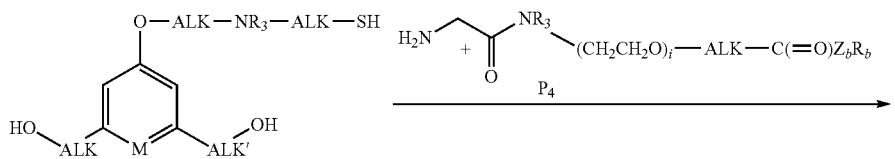

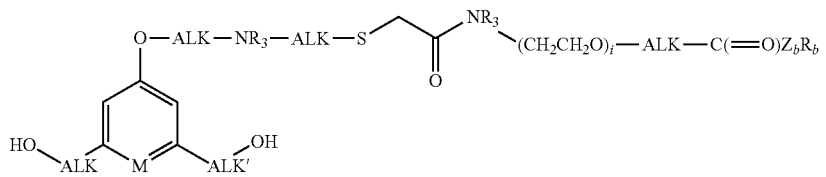

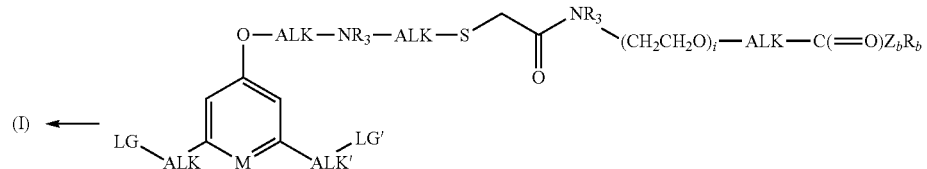

33
-continued
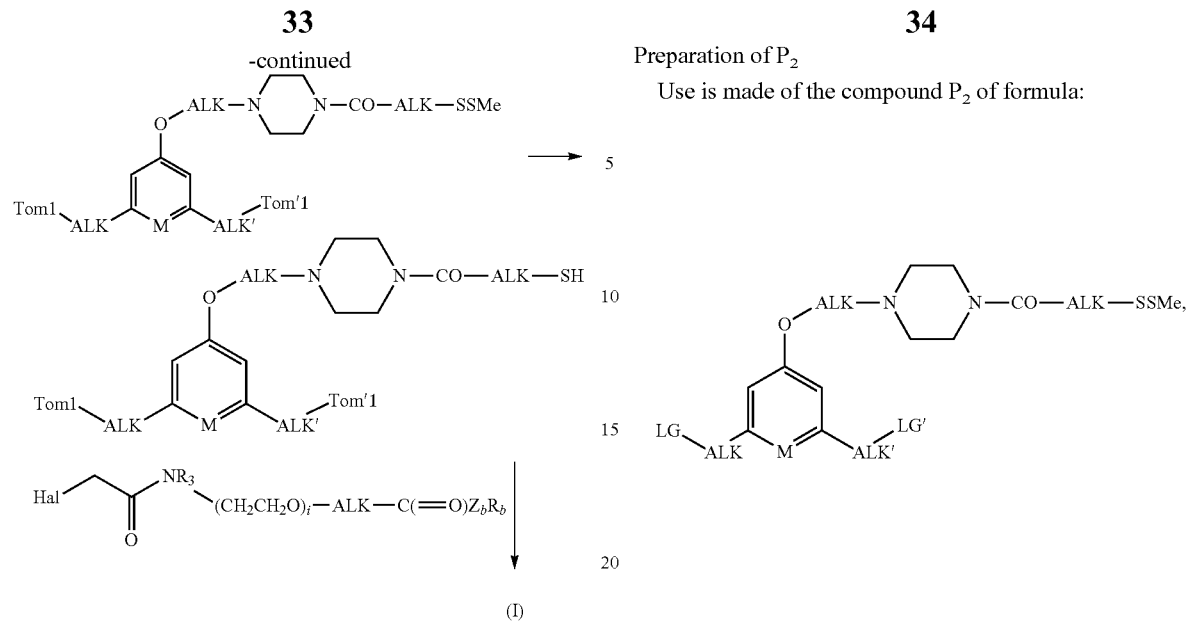
34
Preparation of $P_2$
Use is made of the compound $P_2$ of formula:
which is obtained according to Scheme 5' below:
Scheme 5'
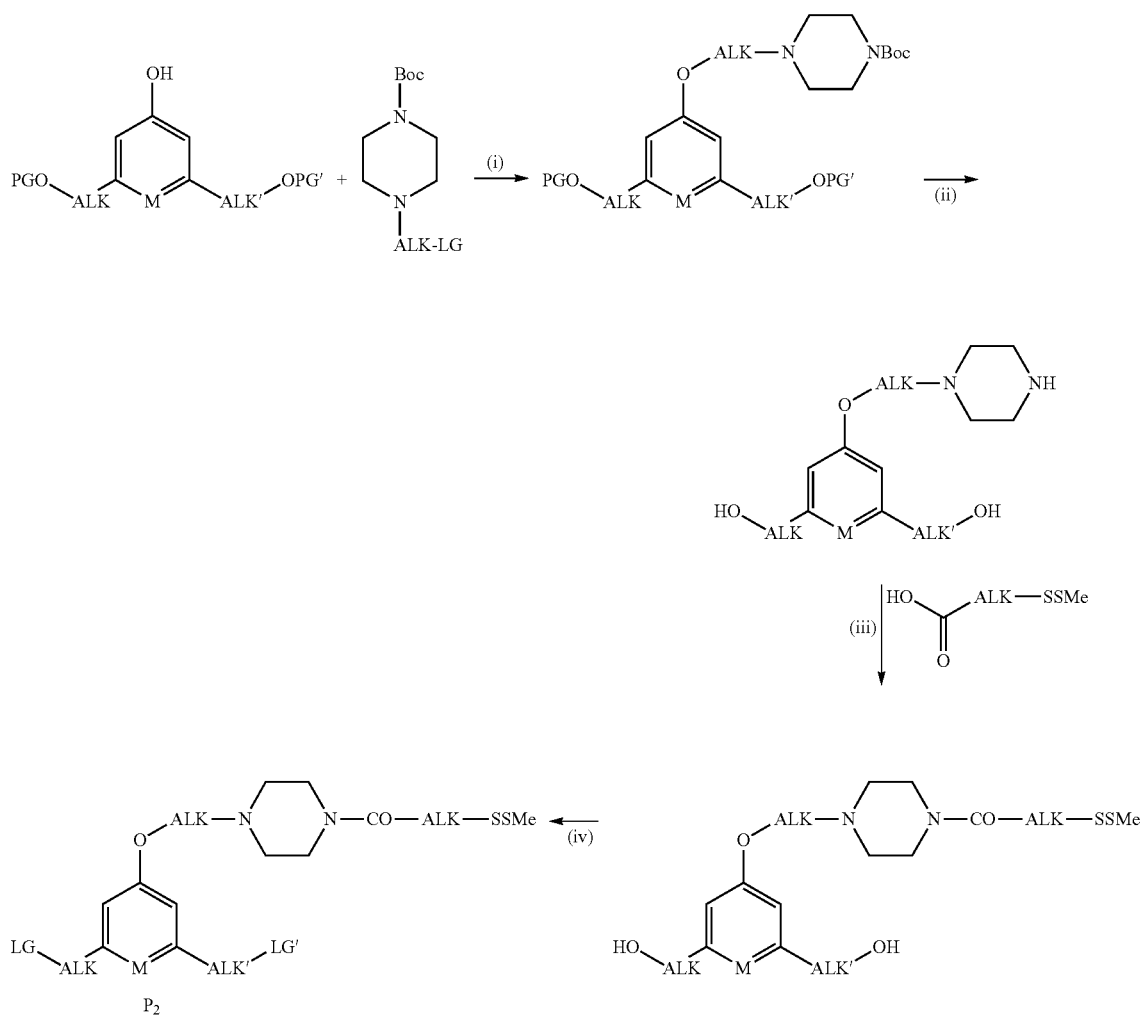

i. alkylation of the hydroxyl of the aromatic ring by a piperazine monoprotected in the 1 position and carrying, in the 4 position, an alkyl chain functionalized in the end position by a nucleofuge LG group. Preferably, the nucleofuge group is a mesylate group and the Williamson reaction is carried out in the presence of a hydride in an anhydrous polar aprotic solvent, such as THF or DMF;

ii. deprotection of the Boc, PG and PG' groups, preferably in an acidic medium, for example in the presence of hydrochloric acid or of TFA when the PG and PG' groups are TBDMS.

According to an alternative form of stages i and ii, it is possible to carry out the nucleophilic substitution of the bromoamine by the hydroxydiester of formula:

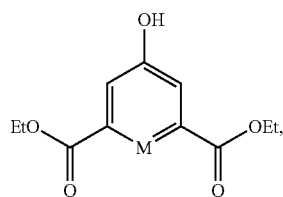

and then to subsequently reduce the ester functional group to give a —CH$_2$OH functional group, for example with sodium borohydride; it is possible to apply, for this, the conditions of the nucleophilic substitution and of the reduction given on pages 62-63 of WO 2007/085930;

iii. coupling carried out after initial activation of the acid to give an NHS ester;

iv. introduction of the leaving groups LG and LG'. In the case of a mesylate group, use is made of methanesulphonyl chloride in the presence of a base, such as a tertiary amine (for example TEA).

Scheme 6

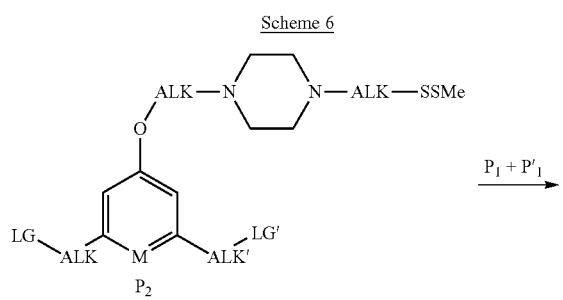

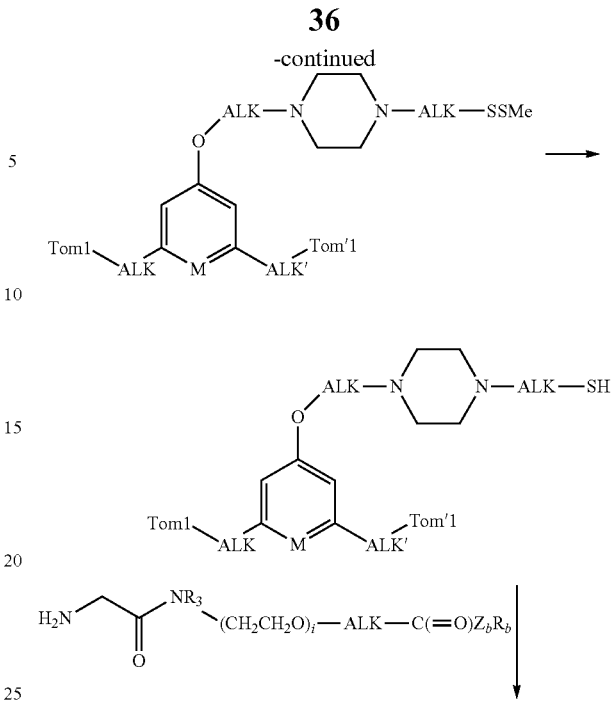

$L_1 = \text{—O—ALK—N} \diagup \diagdown \text{N—ALK—S—}$ and $L_2 = \text{—CH}_2\text{C(=O)—NR}_3\text{—(CH}_2\text{CH}_2\text{O)}_i\text{—ALK—}$ Preparation of P$_2$ Use is made of the compound P$_2$ of formula

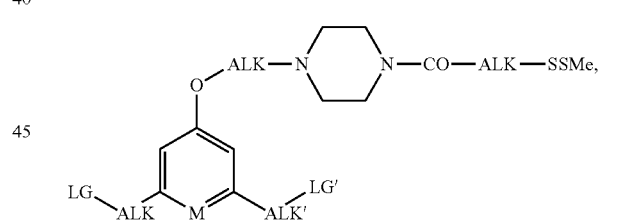

which is obtained by reductive amination according to Scheme 6' below.

Scheme 6'

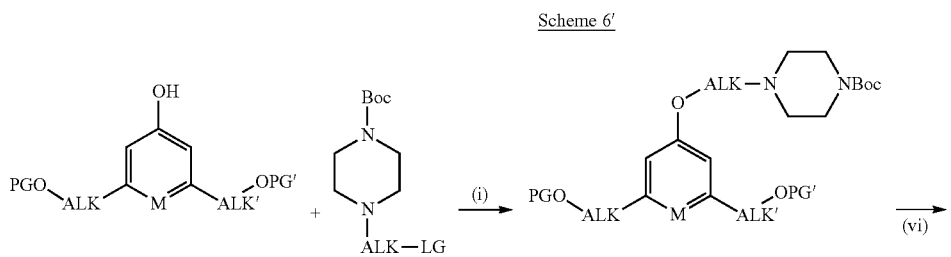

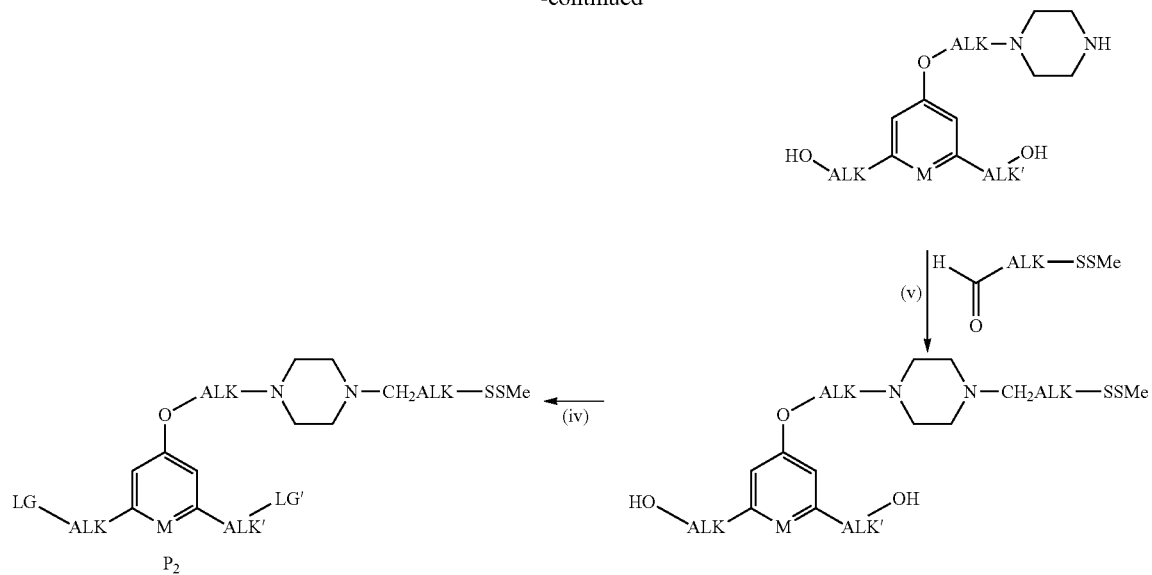
v. introduction of the -ALK-SSMe group by reductive amination carried out, for example, in the presence of cyanoborohydride and of titanium isopropoxide.
An alternative form similar to that represented in Scheme 3" and using the alkylation method described by Kitagawa T. et al., *JACS,* 2006, 128(45), 14448-14449, is given in Scheme 6":

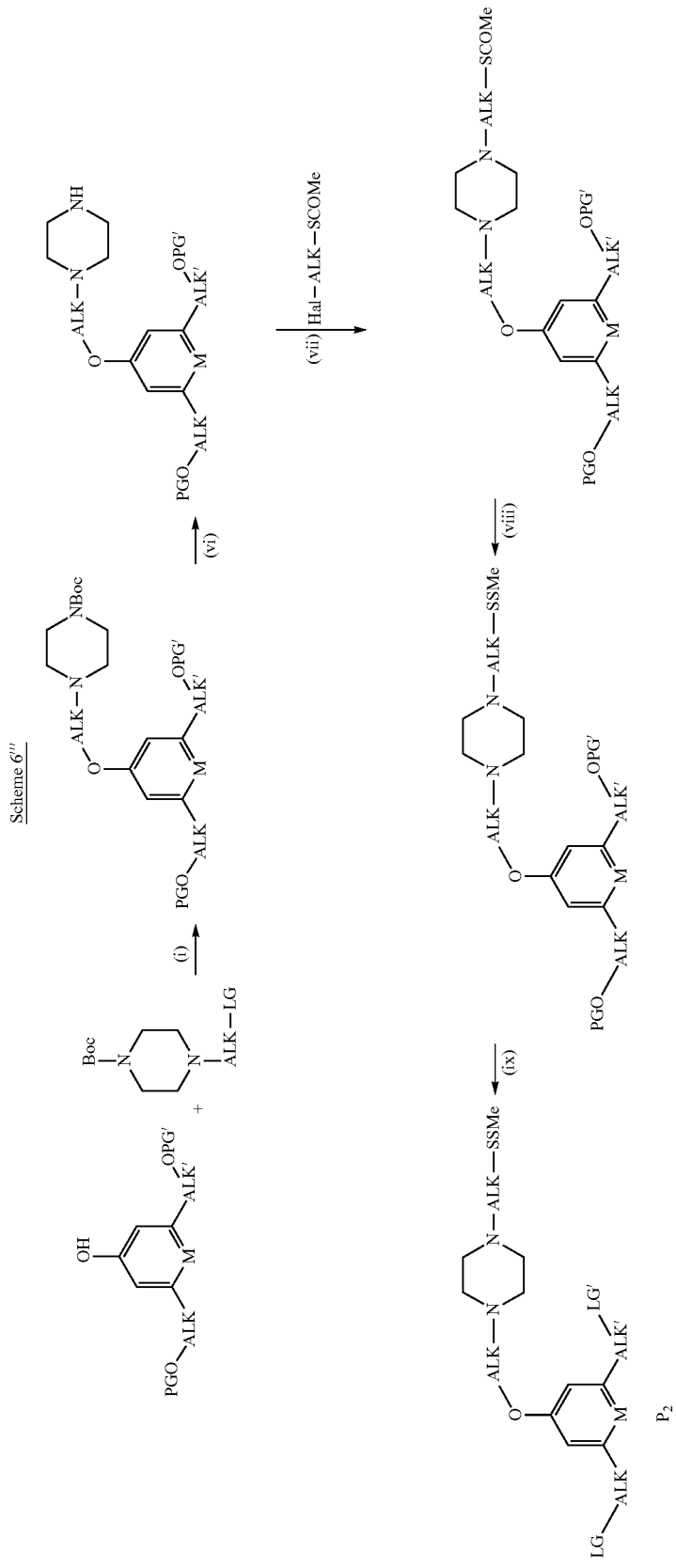

i. alkylation by monoprotected piperazine (cf. stage i. of Scheme 5');

vi. selective deprotection of the Boc group in an acidic medium;

vii. alkylation by an alkyl halide carrying a thioacetyl group in the presence of caesium carbonate in a polar aprotic solvent, such as DMF;

viii. selective cleavage of the acetyl group in a weak basic medium and formation of the —SSMe group by reaction of the intermediate thiol with MeSSO$_2$Me in the presence of a base, such as TEA;

ix. cleavage of the protecting groups PG and PG' and conversion of the hydroxyl groups, preferably to mesylates with methanesulphonyl chloride.

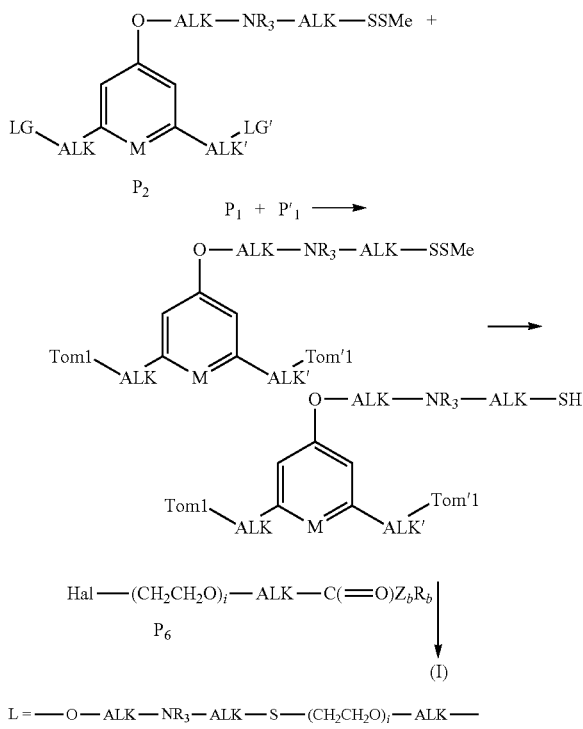

This Scheme draws its inspiration from the preceding Scheme 3. The compound $P_6$ can, for example, be the compound of CAS No. 564476-32-0, which is prepared according to WO 03068144 (cf. compound 10a of FIG. 7), or else the compound of CAS No. 309916-91-4. Analogous compounds with different chain lengths i can be prepared according to the same principle of FIG. 7 of WO 03068144 starting from the corresponding PEG compound.

With Regard to $P_6$

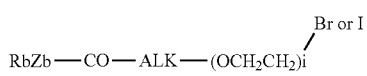

can be prepared according to the schemes below:

Case where ALK=CH$_2$CH$_2$

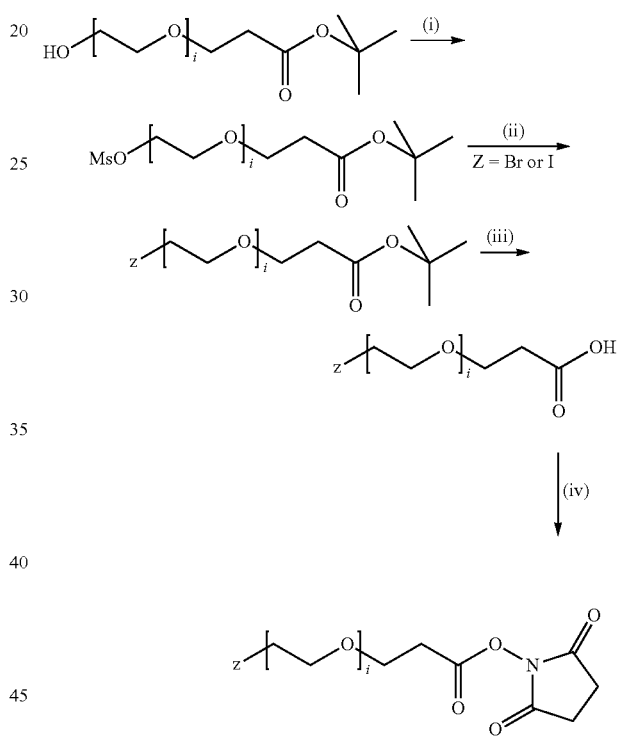

Case where ALK≠CH$_2$CH$_2$

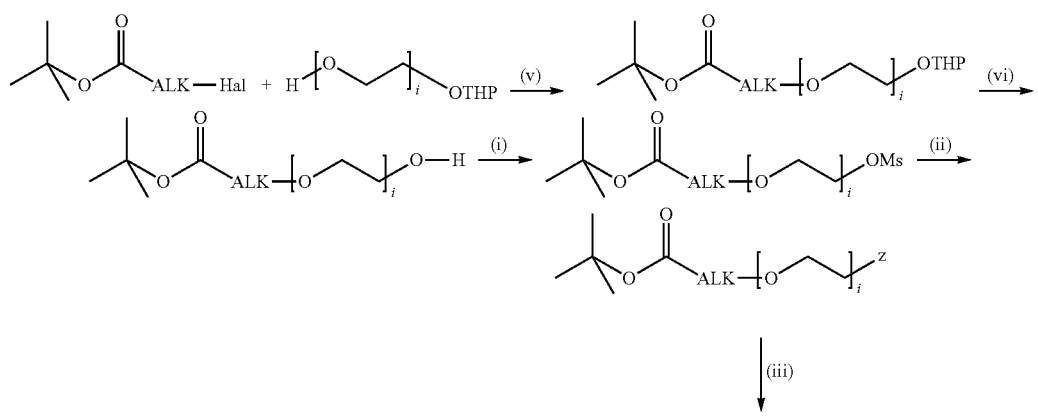

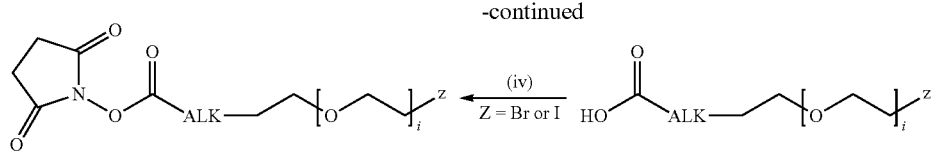

Stage (i): activation of the alcohol in the mesylate form; the reaction is carried out in an anhydrous polar aprotic solvent, such as DCM, by treatment with mesyl chloride in the presence of a base, such as TEA.

Stage (ii): mesylate/halogen exchange; the reaction is carried out at reflux of a polar aprotic solvent, such as acetone, with a sodium halide, such as sodium iodide.

Stage (iii): deprotection using a solution of hydrochloric acid (for example a solution in dioxane) or of trifluoroacetic acid.

Stage (iv): activation of the acid; the reaction is carried out at ambient temperature in a polar aprotic solvent, such as DCM, by treatment with NHS in the presence of a coupling agent, such as DCC.

Stage (v): elongation of the PEG chain; the reaction is carried out in an anhydrous polar aprotic solvent, such as THF or DMF, by treatment of a halogenated ester with the alkoxide of a PEG diol monoprotected in the tetrahydropyran (THP) ether form. The preparation of this type of monoprotected PEG diol is well described in the literature; see, for example, Richard A. et al., *Chem. Eur. J.*, 2005, 11, 7315-7321 or Sakellariou E. G. et al., *Tetrahedron*, 2003, 59, 9083-9090.

Stage (vi): deprotection using a 0.1N hydrochloric acid solution (for example a solution in dioxane or ethanol).

A person skilled in the art can draw his inspiration from the operating conditions of the examples described below.

Process for the Preparation of the Conjugate

The conjugate is obtained by the process consisting in:

(i) bringing into contact and allowing to react an optionally buffered aqueous solution of the binding agent and a solution of a compound of formula (I);

(ii) and then optionally separating the conjugate formed in stage (i) from the compound of formula (I) and/or from the binding agent not having reacted and/or from the aggregates which might be formed.

According to an alternative form, the conjugate which has formed in stage (i) is separated in stage (ii) from the unreacted binding agent and from the aggregates possibly present in the solution. According to another alternative form, the conjugate of stage (i) is separated in stage (ii) only from the unreacted compound of formula (I) and from the aggregates which might be formed and the binding agent which might not have reacted is left in the solution.

The compound of formula (I) preferably comprises an activated functional group —C(=O)$Z_b R_b$, which is reactive with regard to the RCG2 groups, in particular with regard to the amino groups present on the antibodies. A relatively unreactive or insufficiently reactive chemical group can be easily converted into a more reactive group using one or more chemical reactions known to a person skilled in the art; for example —COOH+N-hydroxysuccinimide→

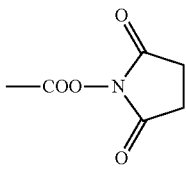

or else —COO($C_1$-$C_6$)alkyl→—COOH→—COOH+N-hydroxysuccinimide→

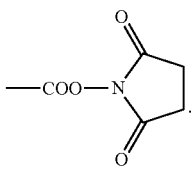

An example of a process applicable in the case of an antibody and of a compound of formula (I) is that given in Example 1.

The aqueous solution of the binding agent can be buffered using, for example, buffers such as, for example, potassium phosphate or N-(2-hydroxyethyl)piperazine-N'-2-ethanesulphonic acid (HEPES buffer). The buffer depends on the nature of the binding agent. The compound of formula (I) is dissolved in a polar organic solvent, for example DMSO or DMA.

The reaction takes place at a temperature generally of between 20 and 40° C. The duration of the reaction can vary between 1 and 24 h. The reaction between the binding agent and compound of formula (I) can be monitored by SEC with a refractometric and/or ultraviolet detector, in order to determine therefrom the state of progression. If the degree of grafting is inadequate, the reaction can be allowed to take place for a longer time and/or further compound of formula (I) can be added. Reference may be made to the general method given in the Examples part for more details on specific conditions which can be used for the conjugation.

A person skilled in the art has available various chromatographic techniques for the separation of stage (ii): the conjugate can be purified, for example, by steric exclusion chromatography (SEC), by adsorption chromatography (such as ion-exchange chromatography, IEC), by hydrophobic interaction chromatography (HIC), by affinity chromatography, by chromatography on mixed supports, such as ceramic hydroxyapatite, or by HPLC. Purification by dialysis or diafiltration can also be used.

The term "aggregates" is understood to mean the combinations which can be formed between two or more binding agents, the binding agents having or not having been modified by conjugation. The aggregates are capable of being formed under the influence of a large number of parameters, such as a high concentration of binding agent in the solution, the pH of the solution, high shear forces, the number of dimers grafted and their hydrophobic nature, or the temperature (see the references cited in the introduction to *J. Membrane Sci.*, 2008, 318, 311-316), the influence of some of them sometimes not being precisely clarified. In the case of proteins or antibodies, reference may be made to *AAPS Journal*, "Protein Aggregation and Bioprocessing", 2006, 8(3), E572-E579. The content of aggregates can be determined using known techniques, such as SEC (see, in this regard, *Analytical Biochemistry*, 1993, 212(2), 469-480).

After stage (i) or (ii), the solution of the conjugate can be subjected to a stage (iii) of ultrafiltration and/or of diafiltration. The conjugate in aqueous solution is thus obtained on conclusion of these stages.

Antibody

The antibody (see, in this regard, Janeway et al., "Immunobiology", 5th edition, 2001, Garland Publishing, New York) can be chosen from those described in particular in Applications WO 04043344, WO 08010101, WO 08047242 and WO 05009369 (anti-CA6). The antibody can in particular be monoclonal, polyclonal or multispecific. An antibody fragment may also be concerned. A murine, human, humanized or chimeric antibody may also be concerned.

Conjugate

A conjugate generally comprises of the order of 1 to 10 pyrrolo[1,4]benzodiazepine dimer(s) attached to the binding agent (this is the degree of grafting or drug-to-antibody ratio (DAR)). This number varies according to the nature of the binding agent and of the dimer and also the operating conditions used for the conjugation (for example, the number of equivalents of dimer with respect to the binding agent, the reaction time, the nature of the solvent and the nature of the possible cosolvent). Bringing the binding agent and the dimer into contact results in a mixture comprising: several conjugates differing individually from one another by different DARs; optionally the unreacted binding agent (in the case of an incomplete reaction); and possibly aggregates. The DAR which is determined on the final solution, for example by UV spectroscopy, thus corresponds to a mean DAR.

In the case where the binding agent is an antibody, UV spectroscopy can be a method used to determine the DAR. This method draws its inspiration from that presented in Antony S. Dimitrov (Ed.), LLC, 2009, "Therapeutic Antibodies and Protocols", vol. 525, 445, Springer Science. It consists in measuring the absorbance of a solution of conjugate after the separation stage (ii) at two wavelengths, denoted LO1 and LO2. Use is made of the following molar extinction coefficients of the naked antibody and of the pyrrolo[1,4]benzodiazepine dimer measured prior to the conjugation.

The absorbances of the solution of conjugate at LO1 and LO2 ($A_{LO1}$ and $A_{LO2}$) are measured either on the corresponding peak of the SEC spectrum (this makes it possible to calculate a "DAR(SEC)") or by using a conventional UV spectrophotometer (this makes it possible to calculate a "DAR(UV)"). The absorbances can be expressed in the form:

$$A_{LO1}=(c_D \times e_{DLO1})+(c_A \times e_{ALO1})$$

$$A_{LO2}=(c_D \times e_{DLO2})+(c_A \times e_{ALO2})$$

equations for which:
- $c_D$ and $c_A$ respectively denote the concentrations in the solution of the part of the conjugate relating to the pyrrolo[1,4]benzodiazepine dimer and the part of the conjugate relating to the antibody;
- $e_{DLO1}$ and $e_{DLO2}$ respectively denote the molar absorption coefficients of the pyrrolo[1,4]benzodiazepine dimer before conjugation at the two wavelengths LO1 and LO2;
- $e_{ALO1}$ and $e_{ALO2}$ respectively denote the molar absorption coefficients of the naked antibody at the two wavelengths LO1 and LO2.

The term "naked antibody" is understood to mean the antibody to which no pyrrolo[1,4]benzodiazepine dimer is attached, that is to say the antibody before the conjugation stage.

The resolution of These two equations results in:

$$c_D=[(e_{ALO1} \times A_{LO2})-(e_{ALO2} \times A_{LO1})]/[(e_{DLO2} \times e_{ALO1})-(e_{ALO2} \times e_{DLO1})]$$

$$c_A=[A_{LO1}-(c_D \times e_{DLO1})]/e_{ALO1}$$

The mean DAR then corresponds to $c_D/c_A$. In the case of the pyrrolo[1,4]benzodiazepine dimers, the two wavelengths LO1=280 nm and LO2=320 nm are considered. The mean DAR measured on the SEC spectrum is preferably between 1 and 10, preferably between 1.5 and 7.

The conjugate can be used as anticancer agent. Due to the presence of the binding agent, the conjugate is rendered highly selective with regard to the tumour cells rather than the healthy cells. This makes it possible to direct the compound of formula (I) which has an anticancer activity to the close surroundings of these or directly inside these (in this regard, see the following publications, which describe the use of conjugates of monoclonal antibodies in the treatment of cancers: "Antibody-drug conjugates for cancer therapy", Carter P. J. et al., *Cancer J.*, 2008, 14, 154-169; "Targeted cancer therapy: conferring specificity to cytotoxic drugs", Chari R., *Acc. Chem. Res.*, 2008, 41, 98-107). It is possible to treat solid or non-solid cancers.

The conjugate is formulated in the form of a buffered aqueous solution at a concentration generally of between 1 and 10 mg/ml. This solution can be injected in the infusion form as is or else can be rediluted to form an infusion solution.

EXAMPLES

The chemical shifts (delta in ppm) are expressed in ppm.
Method A: High Pressure Liquid Chromatography-Mass Spectrometry (LCMS)

The spectra were obtained on a Waters HPLC-SQD device in positive and/or negative electrospray mode (ES+/−). Chromatographic conditions: column: ACQUITY BEH C18 1.7 μm-2.1×50 mm; solvents: A: $H_2O$ (0.1% formic acid), B: $CH_3CN$ (0.1% formic acid); column temperature: 50° C.; flow rate: 1 ml/min; gradient (2 min): from 5 to 50% of B in 0.8 min; 1.2 min: 100% of B; 1.85 min: 100% of B; 1.95 min: 5% of B.
Method B: High Pressure Liquid Chromatography-Mass Spectrometry (LCMS)

The spectra were obtained on a Waters ZQ device in positive and/or negative electrospray mode (ES+/−). Chromatographic conditions: column: XBridge C18 2.5 μm 3×50 mm; solvents: A: $H_2O$ (0.1% formic acid), B: $CH_3CN$ (0.1% formic acid); column temperature: 70° C.; flow rate: 0.9 ml/min; gradient (7 min): from 5 to 100% of B in 5.3 min; 5.5 min: 100% of B; 6:3 min: 5% of B.
Method C: Mass Spectrometry (MS)

The spectra were recorded using chemical ionization (reactant gas: ammonia) on a WATERS GCT of device (direct introduction without LC).
Method D: High Pressure Liquid Chromatography-Mass Spectrometry (LCMS)

The spectra were obtained on a Waters HPLC-SQD device in positive and/or negative electrospray mode (ES+/−). Chromatographic conditions: column: ACQUITY BEH C18 1.7 μm-2.1×50 mm; solvents: A: $H_2O$ (0.1% formic acid), B: $CH_3CN$ (0.1% formic acid); column temperature: 70° C.; flow rate: 1 ml/min; gradient (2 min): from 5 to 50% of B in 1 min; 1.3 min: 100% of B; 1.45 min: 100% of B; 1.75 min: 5% of B.

Method E: High Pressure Liquid Chromatography-Mass Spectrometry (LCMS)

The spectra were obtained on a Waters HPLC-SQD device in electrospray ionization mode in positive and/or negative mode (ES+/−). Chromatographic conditions: column: ACQUITY BEH C18 1.7 μm-2.1×50 mm; solvents: A: $H_2O$ (0.1% formic acid), B: $CH_3CN$ (0.1% formic acid); column temperature: 70° C.; flow rate: 1 ml/min; gradient (4 min): from 5 to 100% of B in 3.15 min; 3.75 min: 5% of B.

Method F: High Pressure Liquid Chromatography-Mass Spectrometry (LCMS)

The spectra were obtained on a Waters HPLC-SQD device in electrospray ionization mode in positive and/or negative mode (ES+/−). Chromatographic conditions: column: ACQUITY BEH C18, 1.7 μm-2.1×30 mm; solvents: A: $H_2O$ (0.1% formic acid), B: $CH_3CN$ (0.1% formic acid); column temperature: 45° C.; flow rate: 0.6 ml/min; gradient (2 min): from 5 to 50% of B in 1 min; 1.3 min: 100% of B; 1.45 min: 100% of B; 1.75 min: 5% of B.

Method G: Deglycosylation and Mass Spectrometry (HRMS) of a Conjugate

Deglycosylation is a technique for enzymatic digestion using glycosidase. It is carried out starting from 500 μl of conjugate+100 μl of Tris HCl 50 mM buffer+10 μl of glycanase-F enzyme (100 units of lyophilized enzyme/100 μl of water). The mixture is vortexed and maintained overnight at 37° C. The deglycosylated sample is then ready to be analysed by HRMS. As the case may be, the HRMS analysis of the sample can also be carried out without prior deglycosylation. In both cases, the mass spectra were obtained on a Waters Q-Tof-2 device in positive electrospray mode (ES+). Chromatographic conditions: column: 4 μm BioSuite 250 URH SEC 4.6×300 mm (Waters); solvents: A: 25 mM ammonium formate+1% of formic acid: B: $CH_3CN$; column temperature 30° C.: flow rate 0.4 ml/min; isocratic 70% A+30% B (15 min).

All the intermediate compounds described in this patent application are claimed for their use in the preparation of a compound of formula (I). More particularly, for each example, all the intermediate compounds described are claimed for their use in the preparation of the respective compound of formula (I).

Example 1

1.1. Preparation of the Conjugate

A conjugate is prepared by reacting hu2H11 (also known as hu53 2H11 on page 15 of WO 2008010101; it is an antibody comprising a VH having the amino acid sequence SED ID No. 24) and N-hydroxysuccinimidyl 3-(2-{2-[2-(2-{3-[3-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)-2,5-dioxopyrrolidin-1-yl] propanoylamino}ethoxy)ethoxy]ethoxy}ethoxy) propanoate.

516 μg of N-hydroxysuccinimidyl 3-(2-{2-[2-(2-{3-[3-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)-2,5-dioxopyrrolidin-1-yl] propanoylamino}ethoxy)ethoxy]ethoxy}ethoxy)propanoate in solution in 540 μl of DMA are added to 8.19 mg of hu2H11 in 2.16 ml of an aqueous buffer with a 0.05 M concentration of N-(2-hydroxyethyl)piperazine-N'-2-ethanesulphonic acid (HEPES), a 0.05 M concentration of NaCl and a 2 mM concentration of ethylenediaminetetraacetic acid (EDTA) of pH=8. After stirring at AT for 3 h, the mixture is filtered through Millex®-SV 0.45 μM (PVDF Durapore Millipore) and purified on a Superdex™ 200 prep grade column (Hiload™ 26/60 GE column) preequilibrated in a saline phosphate buffer brought to pH=6.5 by addition of HCl. The fractions of interest are combined and concentrated on Amicon Ultra-15 (Ultracel 50 k Millipore) and then filtered through Sephadex G-25 (NAP-5 and NAP-10 GE columns) preequilibrated in an aqueous buffer with a 10 mM concentration of histidine comprising 10% of sucrose and 5% of NMP.

The conjugate obtained (2.5 ml) is quantitatively determined by spectrophotometry using the extinction coefficients of 4-{2-[methyl(2-methyl-2-mercaptopropyl)amino] ethoxy}-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine ($e_{319\ nm}$=8848 $M^{-1}cm^{-1}$ and $e_{280\ nm}$=8634 $M^{-1}$ $cm^{-1}$) and of hu2H11 ($e_{280\ nm}$=208 380 $M^{-1}cm^{-1}$): a mean of 3.8 tomaymycin dimers per antibody molecule at the concentration of 1.52 mg/ml was determined.

1.2. N-hydroxysuccinimidyl 3-(2-{2-[2-(2-{3-[3-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl) amino}-1,1-dimethylethylsulphanyl)-2,5-dioxopyrrolidin-1-yl]propanoylamino}ethoxy) ethoxy]ethoxy}ethoxy)propanoate

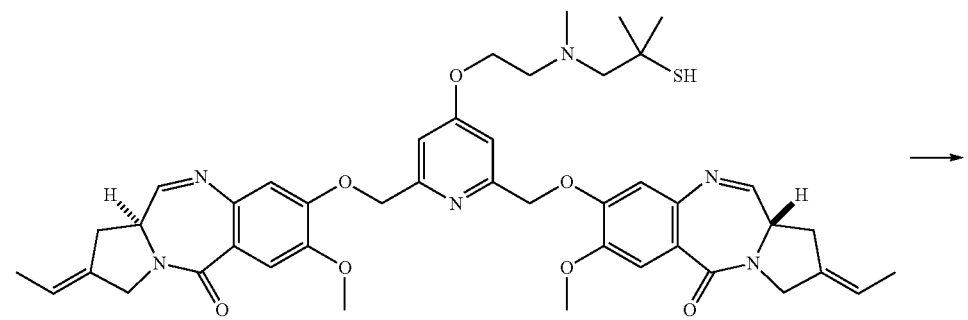

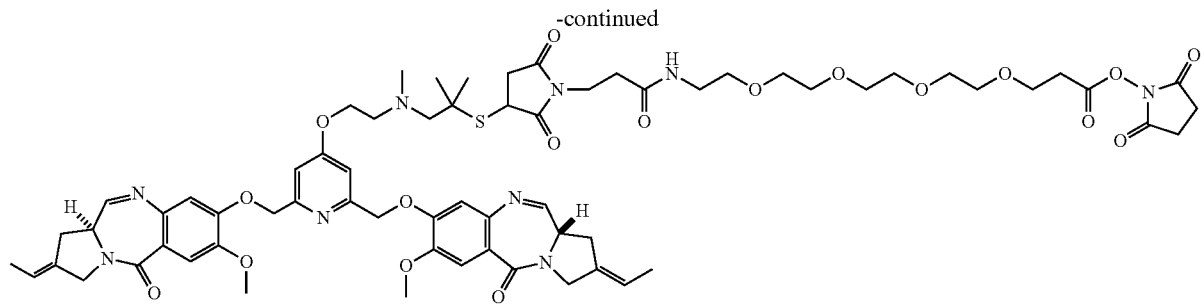

A solution of 9.82 mg of 4-{2-[methyl(2-methyl-2-mercaptopropyl)amino]ethoxy)-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine in 50 μl of DMA and a solution of 6.8 mg of N-hydroxysuccinimidyl 3-{2-[2-(2-{2-[3-(2,5-dioxo-2,5-dihydropyrrol-1-yl)propanoylamino]ethoxy}ethoxy)ethoxy]ethoxy}propanoate in 50 μl of DMA are added to 3.3 mg of diisopropylethylamine supported on resin (3.72 mmol/g). The mixture obtained is stirred at AT for 24 h and then filtered through silica (Interchrom Puriflash Silica 15/35U 2G) using a gradient from 0 to 10% of methanol in DCM. The fractions comprising the desired product are combined, concentrated under RP and then purified by flash chromatography on silica (Interchrom Puriflash Silica 15/35U 2G) using a gradient from 0 to 10% of MeOH in DCM. The fractions comprising the desired product are combined and concentrated under RP. 1.16 mg of N-hydroxysuccinimidyl 3-(2-{2-[2-(2-{3-[3-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino]-1,1-dimethylethylsulphanyl)-2,5-dioxopyrrolidin-1-yl]propanoylamino}ethoxy)ethoxy]ethoxy}ethoxy)propanoate are thus obtained. LC/MS (E): rt=1.38 min; [M+H]⁺: m/z 1322.

1.3. 4-{2-methyl(2-methyl-2-mercaptopropyl)amino]ethoxy)-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine

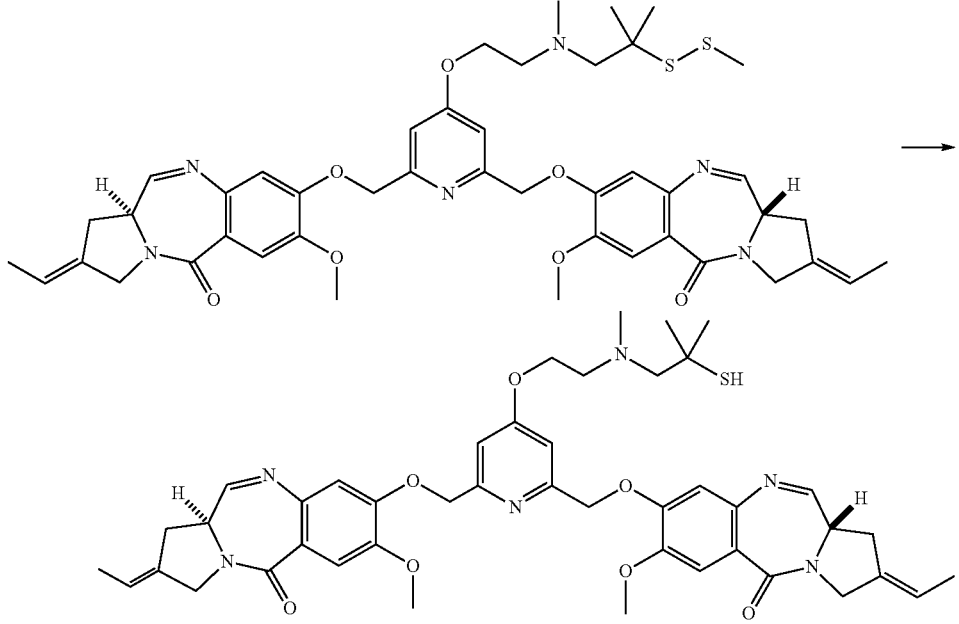

A solution of 40 mg of tris(2-carboxyethyl)phosphine hydrochloride and of 36.6 mg of NaHCO₃ in 680 μl of water is added to 40 mg of 4-{2-[methyl(2-methyl-2-methyldisulphanylpropyl)amino]ethoxy}-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine in solution in 2.1 ml of methanol and 930 μl of DMF. The mixture is stirred at AT for 45 min, then concentrated under RP and purified by flash chromatography on silica (Merck SuperVarioFlash 15 g column, Si60 15-40 μm), using a gradient from 0 to 10% of MeOH in a DCM/acetonitrile 9:1 mixture. The fractions comprising the desired product are combined and concentrated under RP. 21 mg of 4-{2-[methyl(2-methyl-2-mercaptopropyl)amino]ethoxy}-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine are thus obtained. LC/MS (E): rt=1.28 min; [M+H]⁺: m/z 809; [M+H₂O+H]⁺: m/z 827.

1.4. 4-{2-[methyl(2-methyl-2-(methyldisulphanyl)propyl)amino]ethoxy}-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine

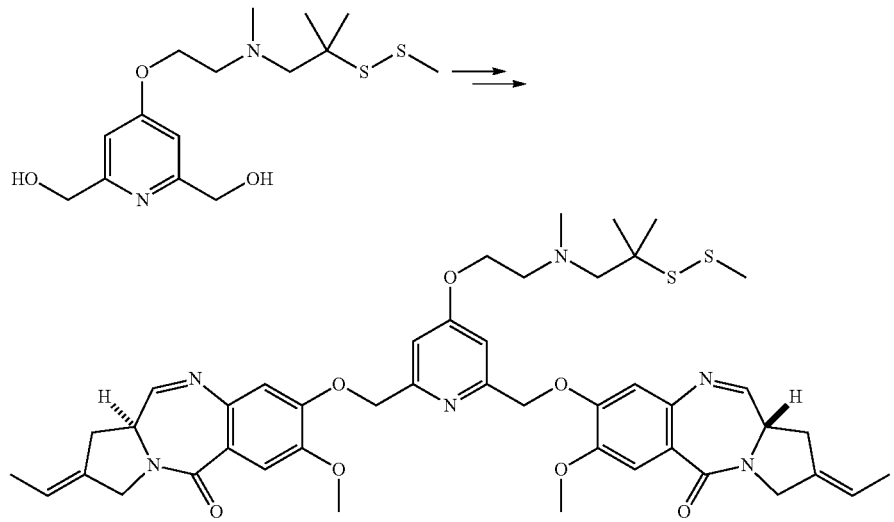

19.6 μl of methanesulphonyl chloride are added to a solution, cooled to −25° C., of 22 mg of 4-{2-[methyl(2-methyl-2-(methyldisulphanyl)propyl)amino]ethoxy}-2,6-bis(hydroxymethyl)pyridine and of 53 μl of TEA in 0.5 ml of DCM. After stirring for 30 min, the mixture is hydrolysed and the organic phase is washed with water, then dried over $MgSO_4$ and concentrated under RP. The residue thus obtained (22 mg) is added to a solution of 20 mg of tomaymycin in 0.7 ml of DMF, and also 30 mg of $K_2CO_3$ and 12 mg of KI. The mixture is stirred at 30° C. for 2 h and then hydrolysed with 4 ml of water. The resulting precipitate is washed with water, dried under vacuum, then dissolved in DCM, concentrated under RP and purified by flash chromatography on silica (Merck SuperVarioFlash 15 g column, Si60 15-40 μm), using a gradient from 0 to 5% of MeOH in DCM. The fractions comprising the desired product are combined and concentrated under RP. 8 mg of 4-{2-[methyl(2-methyl-2-(methyldisulphanyl)propyl)amino]ethoxy}-2,6-bis[(S)-2-eth-(E)-ylidene-7-methoxy-1,2,3,11a-tetrahydropyrrolo[2,1-c][1,4]benzodiazepin-5-one-8-yloxymethyl]pyridine are thus obtained. $^1$H NMR (500 MHz, d-chloroform): 1.28 (s, 6H); 1.76 (d, J=6.4 Hz, 6H); 2.39 (s, 3H); 2.43 (s, 3H); 2.60 (s, 2H); 2.91 (s, 2H); 2.97 (s, 4H); 3.91 (d, J=4.2 Hz, 2H); 4.00 (s, 6H); 4.09 (s, 2H); 4.27 (s, 4H); 5.27 (s, 4H); 5.61 (q, J=6.4 Hz, 2H); 6.85 (s, 2H); 7.00 (s, 2H); 7.56 (s, 2H); 7.65 (d, J=4.2 Hz, 2H). LC/MS (A): rt=0.74 min; [M+H]$^+$: m/z 855; [M−H]$^-$: m/z 853.

1.5. 4-{2-methyl(2-methyl-2-(methyldisulphanyl)propyl)amino]ethoxy}-2,6-bis(hydroxymethyl)pyridine

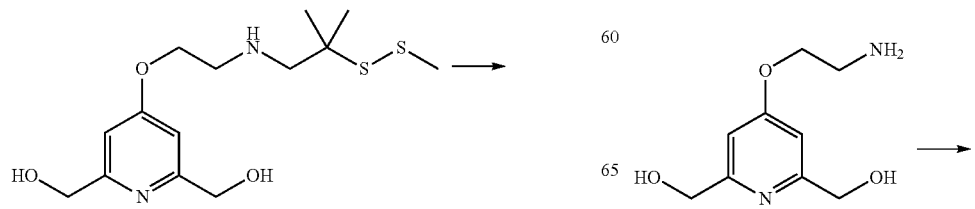

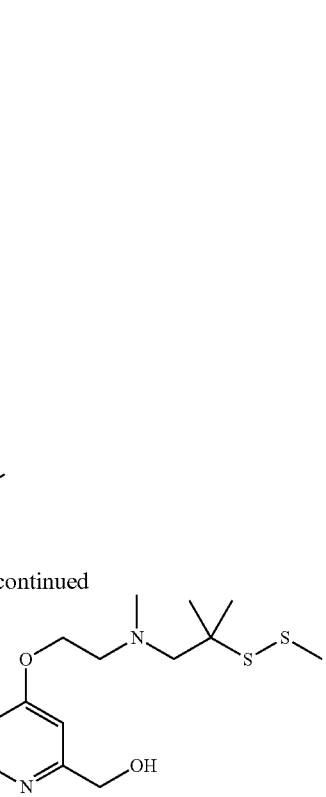

365 μl of formic acid are added to a suspension, cooled to 0° C., of 322 mg of 4-[2-(2-methyl-2-(methyldisulphanyl)propylamino)ethoxy]-2,6-bis(hydroxymethyl)pyridine in 262 μl of formaldehyde. The mixture is heated at 100° C. for 1¼ hours. After returning to ambient temperature, the mixture is hydrolysed and then a 5N aqueous sodium hydroxide solution is added until a pH=12 is obtained. The aqueous phase is extracted 3× with AcOEt and the combined organic phases are dried over $MgSO_4$ and concentrated under RP. 310 mg of 4-{2-[methyl(2-methyl-2-(methyldisulphanyl)propyl)amino]ethoxy}-2,6-bis(hydroxymethyl)pyridine are thus obtained.
$^1$H NMR (300 MHz, d$_6$-DMSO): 1.26 (s, 6H); 2.39 (s, 3H); 2.40 (s, 3H); 2.60 (s, 2H); 2.88 (t, J=5.7 Hz, 2H); 4.13 (t, J=5.7 Hz, 2H); 4.45 (d, J=6.0 Hz, 4H); 5.31 (t, J=6.0 Hz, 2H); 6.85 (s, 2H). LC/MS (A): rt=0.22 min; [M+H]$^+$: m/z 333; [M+HCO2H−H]$^-$: m/z 377.

1.6. 4-[2-(2-methyl-2-(methyldisulphanyl)propylamino)ethoxy]-2,6-bis(hydroxymethyl)pyridine

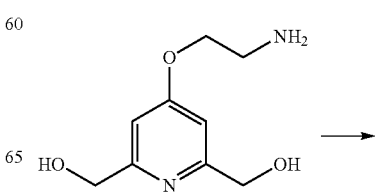

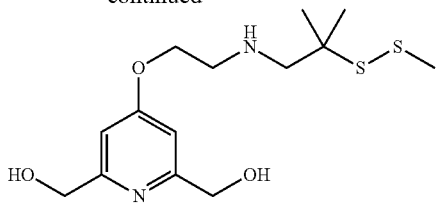

270 µl of 2-(methyldithio)isobutyraldehyde and 730 µl of titanium isopropoxide are added to a suspension of 390 mg of 4-[2-aminoethoxy]-2,6-bis(hydroxymethyl)pyridine (prepared after deprotection of the Boc group from 4-(2-(tert-butoxycarbonylamino)ethoxy)-2,6-bis(hydroxymethyl)pyridine described on page 101 of WO 07085930) in 2 ml of THF. After 20 min, an additional 270 µl of 2-(methyldithio)isobutyraldehyde and an additional 730 µl of titanium isopropoxide are added and the mixture is stirred at AT for 2 h. 6 ml of ethanol are then added to the mixture, the mixture is stirred at AT for 20 min and then 124 mg of sodium cyanoborohydride are added to the mixture. After stirring for 45 min, an additional 124 mg of sodium cyanoborohydride are added and, after stirring for 1 h, the mixture is concentrated under RP and the residue is diluted in AcOEt and water. The resulting precipitate is filtered off and dissolved in a 1M aqueous HCl solution. The aqueous phase obtained is brought to basic pH with a 5M aqueous sodium hydroxide solution and extracted three times with DCM, and the combined organic phases are concentrated under RP. 322 mg of 4-[2-(2-methyl-2-(methyldisulphanyl)propylamino)ethoxy]-2,6-bis(hydroxymethyl)pyridine are thus obtained.

¹H NMR (400 MHz, d₆-DMSO): 1.26 (s, 6H); 1.81 (broad m, 1H); 2.39 (s, 3H); 2.67 (broad s, 2H); 2.94 (broad t, J=5.7 Hz, 2H); 4.11 (t, J=5.7 Hz, 2H); 4.45 (d, J=5.5 Hz, 4H); 5.32 (t, J=5.5 Hz, 2H); 6.85 (s, 2H). LC/MS (A): rt=0.24 min; [M+H]⁺: m/z 347.

Example 2

2.1. Preparation of the Conjugate

A conjugate is prepared as for Ex. 1 by reacting hu2H11 and N-hydroxysuccinimidyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoate. The conjugate obtained is quantitatively determined by spectrophotometry using the extinction coefficients of 4-{2-[methyl(2-methyl-2-mercaptopropyl)amino]ethoxy}-2,6-bis[(S)-2-eth-(E)-ylidene-7-methoxy-1,2,3,11a-tetrahydropyrrolo[2,1-c][1,4]benzodiazepine-5-one-8-yloxymethyl]pyridine ($e_{319\,nm}$=8848 M⁻¹cm⁻¹, $e_{280\,nm}$=8634 M⁻¹cm⁻¹) and of hu2H11 ($e_{280\,nm}$=208 380 M⁻¹cm⁻¹): a mean of 5.6 tomaymycin dimers per antibody molecule was determined.

2.1. N-hydroxysuccinimidyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoate

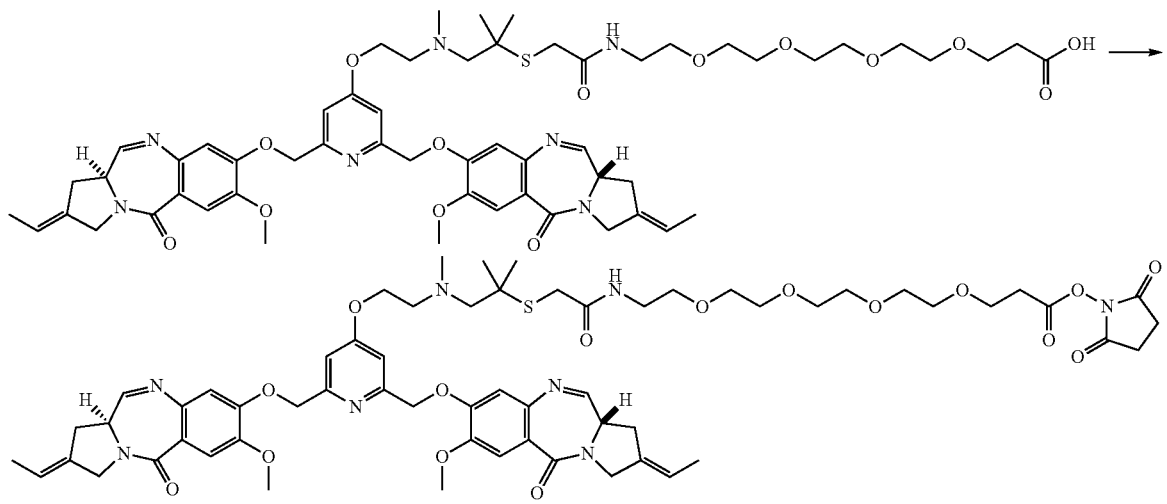

5.5 mg of N,N'-disuccinimidyl carbonate and 15 µl of DIPEA are added to 12 mg of 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoic acid in solution in 1 ml of THF and 1 ml of DCM. After 3 h at AT, 4 ml of DCM are added and the resulting organic phase is washed twice with water, dried over MgSO₄ and concentrated under RP and the residue is purified by flash chromatography on silica (Interchrom Puriflash Silica 15/35U 2G) using a gradient from 3 to 8% of methanol in DCM. 8 mg of N-hydroxysuccinimidyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoate are thus obtained. LC/MS (E): rt=1.36 min; [M+2H₂O+Na]⁺: m/z 1270; [M+H₂O+Na]⁺: m/z 1252; [M+H₂O+H]⁺: m/z 1229; [M+H]⁻: m/z 1211.

2.2. 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoic acid

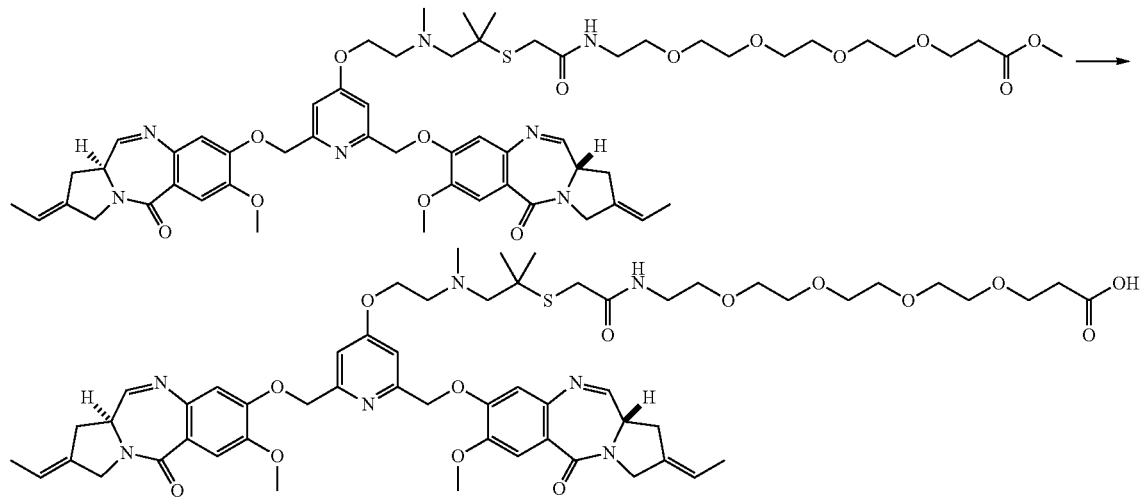

17.5 μl of an aqueous lithium hydroxide solution and 100 μl of water are added to 18 mg of methyl 3-{2-[2-(2-{2-[2-(2-([2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoate in solution in 270 μl of THF. After 2 h, the mixture is diluted in DCM and a phosphate buffer is added to pH=3. The resulting aqueous phase is extracted 3× with DCM, the combined organic phases are dried over MgSO$_4$ and concentrated under RP and the residue is purified by flash chromatography on silica (Interchrom Puriflash Silica 15/35U 2G) using a gradient from 3 to 15% of methanol in DCM. 11.5 mg of 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}-ethoxy)ethoxy]ethoxy}propanoic acid are thus obtained. LC/MS (D): rt=0.88 min; [M+H$_2$O+Na]$^+$: m/z 1154; [M+H$_2$O+H]$^+$: m/z 1133; [M+H]$^+$: m/z 1115.

2.3. Methyl 3-{2-[2-(2-{2-[2-(2-{(2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetylamino]ethoxy}ethoxy)ethoxy]ethoxy}propanoate Prepared according to Ex. 1 from methyl 3-{2-[2-(2-{2-[2-(2-{[2-(2,6-bis(hydroxymethyl)pyridin-4-yloxy)ethyl]methylamino}-1,1-dimethylethylsulphanyl)acetylamino]ethoxy}ethoxy)ethoxy]ethoxy}-propanoate:

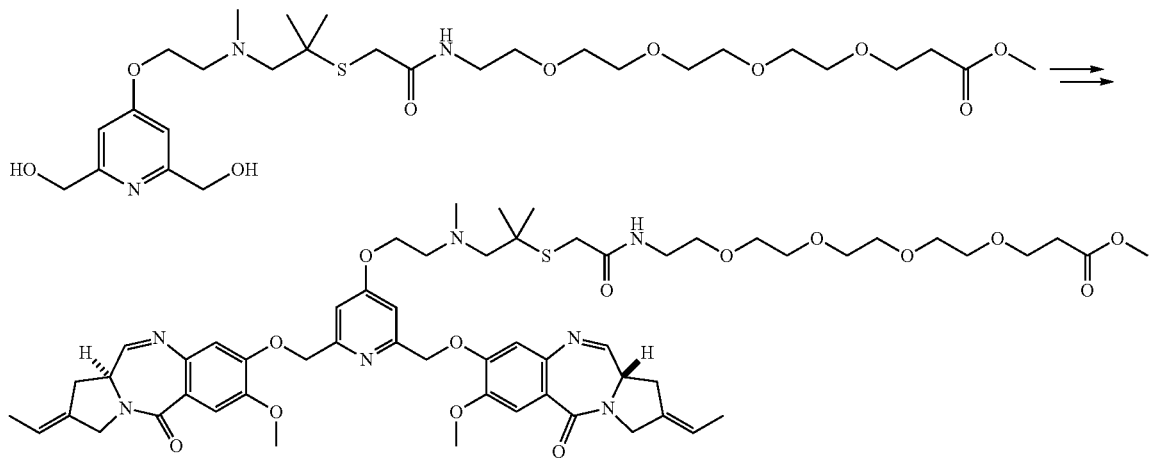

LC/MS (D): rt=0.93 min; [M+H₂O+H]⁺: m/z 1146; [M+H]⁺: m/z 1128.

2.4. Methyl 3-{2-[2-(2-{2-[2-(2-{[2-(2,6-bis(hydroxymethyl)pyridin-4-yloxy)ethyl](methyl)amino}-1,1-dimethylethylsulphanyl)acetylamino]ethoxy}ethoxy)ethoxy]ethoxy}propanoate

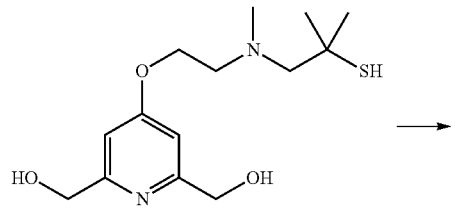

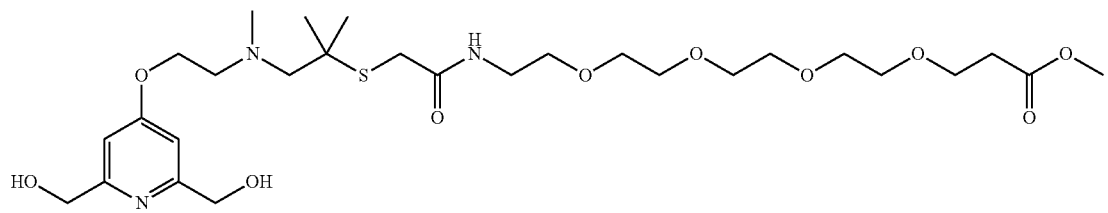

73.7 mg of methyl 3-[2-(2-{2-[2-(2-iodoacetylamino)ethoxy]ethoxy}ethoxy)ethoxy]propanoate in solution in 1 ml of DMF and 39 µl of DIPEA are added to 45 mg of 4-{2-[(2-mercapto-2-methylpropyl)(methyl)amino]ethoxy}-2,6-bis(hydroxymethyl)pyridine in solution in 1 ml of DMF. After 24 h at AT, the mixture is concentrated under RP and purified by flash chromatography on silica (Analogix Super Flash SiO₂ SF25-8 g), using a gradient from 0 to 10% of methanol in DCM. 53 mg of methyl 3-{2-[2-(2-{2-[2-(2-{[2-(2,6-bis(hydroxymethyl)pyridin-4-yloxy)ethyl](methyl)amino}-1,1-dimethylethylsulphanyl)acetylamino]ethoxy}ethoxy)ethoxy]ethoxy}propanoate are thus obtained.

¹H NMR (400 MHz, d₆-DMSO): 1.21 (s, 6H); 2.40 (s, 3H); 2.50 to 2.56 (m, 4H); 2.87 (t, J=5.8 Hz, 2H); 3.15 to 3.23 (m, 4H); 3.40 (t, J=5.8 Hz, 2H); 3.47 to 3.52 (m, 12H); 3.59 (s, 3H); 3.62 (t, J=6.2 Hz, 2H); 4.13 (t, J=5.8 Hz, 2H); 4.45 (d, J=5.8 Hz, 4H); 5.31 (t, J=5.8 Hz, 2H); 6.85 (s, 2H); 7.98 (t, J=5.8 Hz, 1H). LC/MS (A): rt=0.35 min; [M+H]⁺: m/z 620; [M+2H]²⁺: m/z 310.5 (base peak); [M−H+HCO₂H]⁻: m/z 664.

2.5. Methyl 3-[2-(2-{2-[2-(2-iodoacetylamino)ethoxy]ethoxy}ethoxy)ethoxy]propanoate

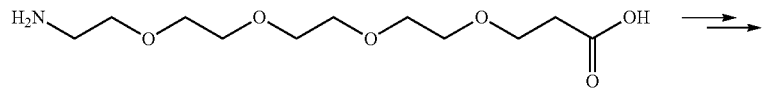

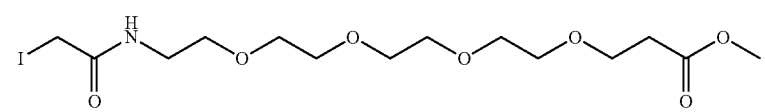

117.4 mg of N-hydroxysuccinimidyl iodoacetate in solution in 3 ml of DCM are added to 100 mg of 3-(2-{2-[2-(2-aminoethoxy)ethoxy]ethoxy}ethoxy)propanoic acid. After 2 h at AT, 330 µl of MeOH are added and the mixture is cooled to 0° C. 360 µl of a 2M solution of trimethylsilyldiazomethane in hexane are added. After 1 h, the mixture is neutralized by addition of 50 µl of acetic acid and then a saturated aqueous NaHCO₃ solution is added until pH=8 is obtained. The organic phase is dried over MgSO₄ and concentrated under RP, and the residue is purified by flash chromatography on silica (Interchrom Puriflash Silica 15/35U 10G) using a gradient from 0 to 10% of methanol in DCM. 132 mg of methyl 3-[2-(2-{2-[2-(2-iodoacetylamino)ethoxy]ethoxy}ethoxy)ethoxy]propanoate are thus obtained.

¹H NMR (400 MHz, d₆-DMSO): 2.54 (t, J=6.4 Hz, 2H); 3.20 (q, J=5.8 Hz, 2H); 3.41 (t, J=5.8 Hz, 2H); 3.48 to 3.53 (m, 12H); 3.60 (s, 3H); 3.63 (t, J=6.4 Hz, 2H); 3.65 (s, 2H); 8.27 (broad t, J=5.8 Hz, 1H). LC/MS (A): rt=0.54 min; [M+H]⁺: m/z 448; [M+HCO₂H−H]⁻: m/z 492.

2.6. 4-{2-[(2-mercapto-2-methylpropyl)(methyl)amino]ethoxy}-2,6-bis(hydroxymethyl)pyridine

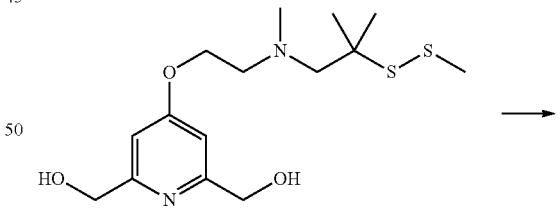

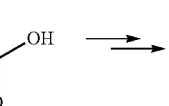

-continued

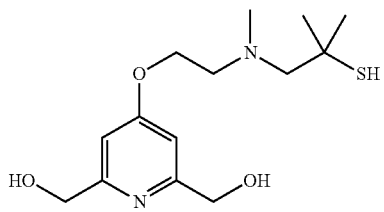

A solution of 198 mg of tris(2-carboxyethyl)phosphine hydrochloride in 730 µl of water is added to 80 mg of 4-{2-[methyl(2-methyl-2-(methyldisulphanyl)propyl)amino]ethoxy}-2,6-bis(hydroxymethyl)pyridine in solution in 1.95 ml of methanol. After 2 h at AT, the mixture is concentrated under RP and the residue is taken up in 10 ml of water. The aqueous phase is brought to pH=8 by addition of an aqueous sodium hydroxide solution and then extracted 2× with AcOEt. The combined organic phases are washed with a saturated aqueous NaCl solution and concentrated under RP. 68 mg of 4-{2-[(2-mercapto-2-methylpropyl)(methyl)amino]ethoxy}-2,6-bis(hydroxymethyl)pyridine are obtained.

$^1$H NMR (400 MHz, d$_6$-DMSO): 1.28 (s, 6H); 2.43 (s, 3H); 2.54 (s, 2H); 2.62 (s, 1H); 2.91 (t, J=5.7 Hz, 2H); 4.15 (t, J=5.7 Hz, 2H); 4.45 (d, J=5.8 Hz, 4H); 5.30 (t, J=5.8 Hz, 2H); 6.85 (s, 2 H). LC/MS (A): rt=0.11 min; [M+H]$^+$: m/z 301.

Example 3

3.1. Preparation of the Conjugate

A conjugate is prepared as for Ex. 1 by reacting hu2H11 and N-hydroxysuccinimidyl 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin- 5-one-8-yloxymethyl]phenyl-4-yl)-1-methylethylsulphanyl]acetylamino}ethoxy)ethoxy]-ethoxy}ethoxy)propanoate.

The conjugate obtained is quantitatively determined by spectrophotometry using the extinction coefficients of 1-(1-methyl-1-(methyldisulphanyl)ethyl)-3,5-bis[(S)-2-eth-(E)-ylidene-7-methoxy-1,2,3,11a-tetrahydropyrrolo[2,1-c][1,4]benzodiazepin-5-one-8-yloxymethyl]benzene (e$_{319\,nm}$=8460 M$^{-1}$cm$^{-1}$ and e$_{280\,nm}$=10 531 M$^{-1}$cm$^{-1}$) and of hu2H11 (e$_{280\,nm}$=208 380 M$^{-1}$cm$^{-1}$): a mean of 4.2 tomaymycin derivatives per antibody molecule was determined.

3.2. N-hydroxysuccinimidyl 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin-5-one-8-yloxymethyl]phenyl-4-yl)-1-methylethylsulphanyl]acetylamino}ethoxy)ethoxy]ethoxy}ethoxy)propanoate Prepared as for Ex. 2 from 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin-5-one-8-yloxymethyl]phenyl-4-yl)-1-methylethylsulphanyl]acetylamino}ethoxy)ethoxy]ethoxy}ethoxy)propanoic acid:

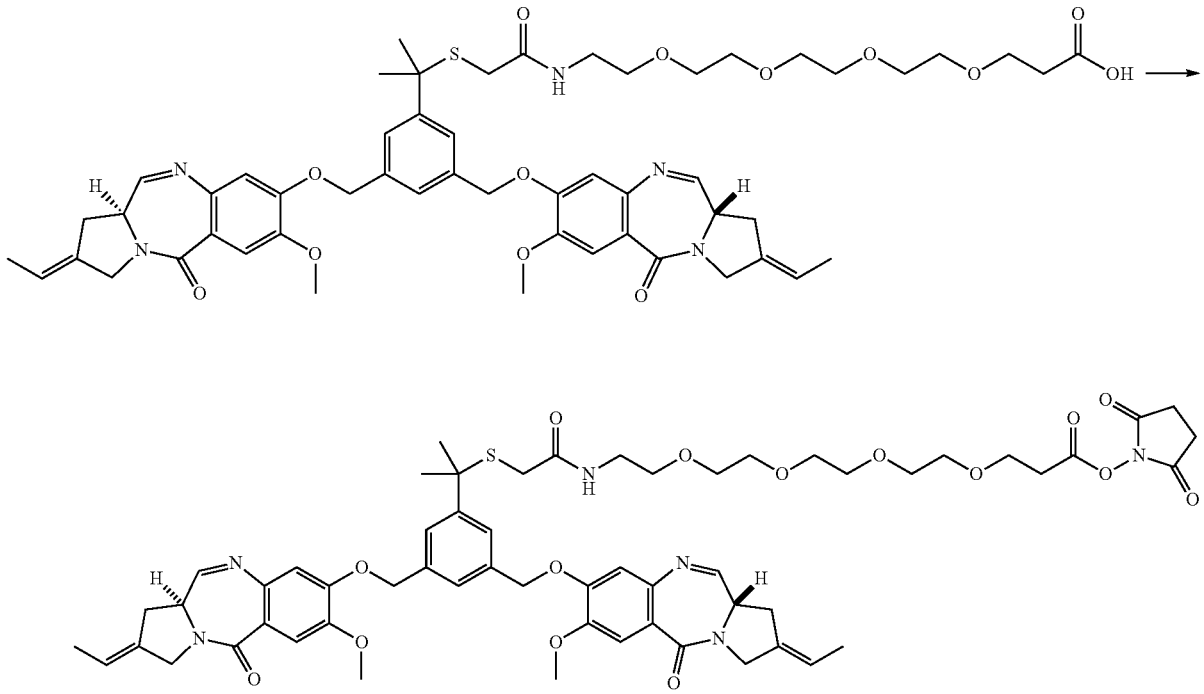

LC/MS (F): rt=1.27 min; [M+H]$^+$: m/z 1123.

3.3. 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin-5-one-8-yloxymethyl]phenyl-4-yl)-1-methylethylsulphanyl]acetylamino}ethoxy)ethoxy]ethoxy}ethoxy)propanoic acid Prepared as for Ex. 2 from methyl 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin-5-one-8-yloxymethyl]phenyl-4-yl)-1-methylethylsulphanyl]acetylamino}ethoxy)ethoxy]ethoxy}ethoxy)propanoate:

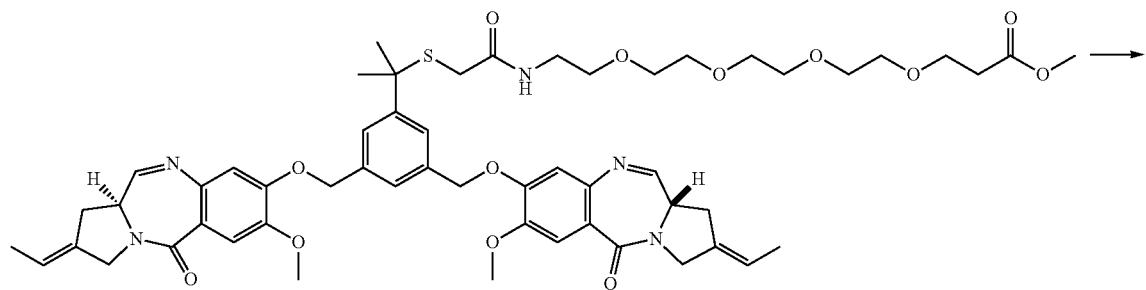
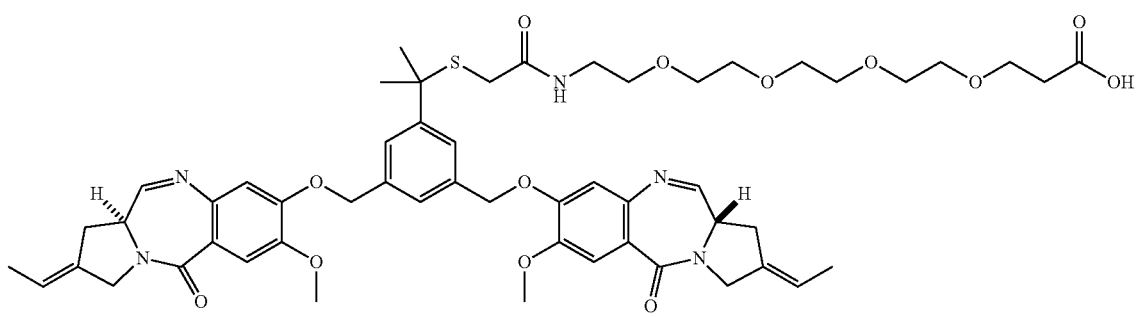
LC/MS (F): rt=1.19 min; [M+H]⁺: m/z 1026.
3.4. Methyl 3-(2-{2-[2-(2-{2-[1-(3,5-bis[(S)-2-eth-(E)-ylidene-7-methoxy-1,2,3,11a-tetrahydropyrrolo[2,1-c][1,4]benzodiazepin-5-one-8-yloxymethyl]phenyl-4-yl)-1-methylethylsulphanyl]acetylamino}ethoxy)ethoxy]ethoxy}ethoxy)propanoate
Prepared as for Ex. 2 from methyl 3-(2-{2-[2-(2-{2-[1-(3,5-bis(hydroxymethyl)phenyl)-1-methylethylsulphanyl]acetylamino}ethoxy)ethoxy]ethoxy}ethoxy)propanoate:
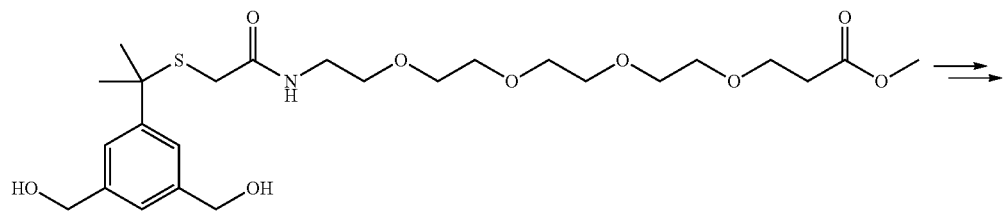
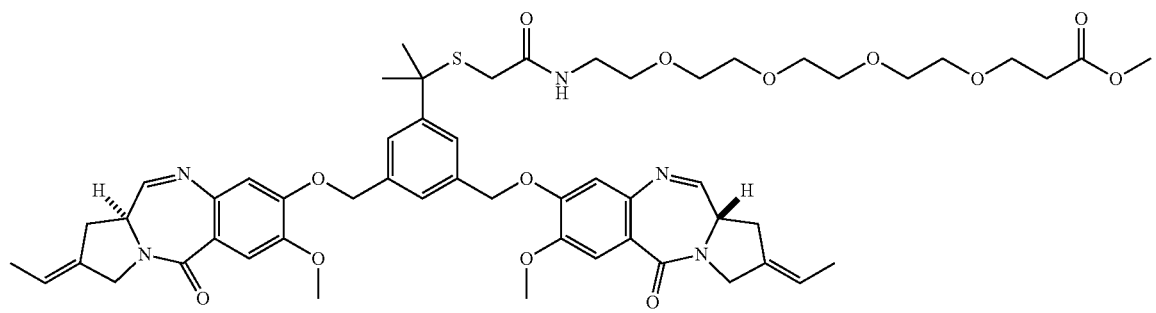
LC/MS (F): rt=1.28 min; [M+H]⁺: m/z 1040.

3.5. Methyl 3-(2-{2-[2-(2-{2-[1-(3,5-bis(hydroxymethyl)phenyl)-1-methylethylsulphanyl]-acetylamino}ethoxy)ethoxy]ethoxy}ethoxy)propanoate Prepared as for Ex. 2 from 3,5-bis(hydroxymethyl)-1-(1-mercapto-1-methylethyl)benzene:

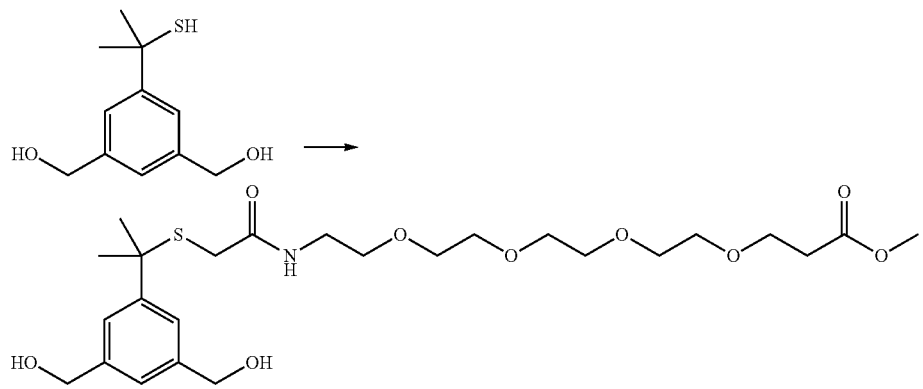

$^1$H NMR (400 MHz, d$_6$-DMSO): 1.64 (s, 6H); 2.53 (t, J=6.2 Hz, 2H); 2.93 (s, 2H); 3.15 (q, J=6.0 Hz, 2H); 3.37 (t, J=6.0 Hz, 2H); 3.49 (m, 12H); 3.59 (s, 3H); 3.62 (t, J=6.2 Hz, 2H); 4.49 (d, J=5.6 Hz, 4H); 5.13 (t, J=5.6 Hz, 2H); 7.14 (s, 1H); 7.32 (s, 2H); 7.84 (t, J=6.0 Hz, 1H). LC/MS (B): rt=2.98 min; [M+H]$^+$: m/z 532; base peak: m/z 354; [M−H+HCO$_2$H]$^-$: m/z 576.

3.8. 3,5-bis(hydroxymethyl)-1-(1-mercapto-1-methylethyl)benzene

A solution of 43 mg of 5-hydroxymethyl-1-(1-mercapto-1-methylethyl)-3-[(tert-butyl)dimethylsilanyloxymethyl]benzene in 1 ml of an acetic acid/THF/water (3/1/1) mixture is stirred at AT for 4.5 h and concentrated under RP, and then the residue is taken up in 3 ml of water. The pH of the aqueous phase is brought to 7 by addition of a 10% aqueous Na$_2$CO$_3$ solution and then the aqueous phase is extracted with AcOEt. The organic phase is dried over MgSO$_4$ and concentrated under RP. 18 mg of 3,5-bis(hydroxymethyl)-1-(1-mercapto-1-methylethyl)benzene are thus obtained.

$^1$H NMR (400 MHz, d$_6$-DMSO): 1.76 (s, 6H); 3.19 (s, 1H); 4.48 (d, J=5.9 Hz, 4H); 5.14 (t, J=5.9 Hz, 2H); 7.13 (s, 1H); 7.36 (s, 2H). MS (C): CI: [M+NH$_4$]$^+$: m/z 230.

3.9. 5-Hydroxymethyl-1-(1-mercapto-1-methylethyl)-3-[(tert-butyl)dimethylsilanyloxymethyl]benzene

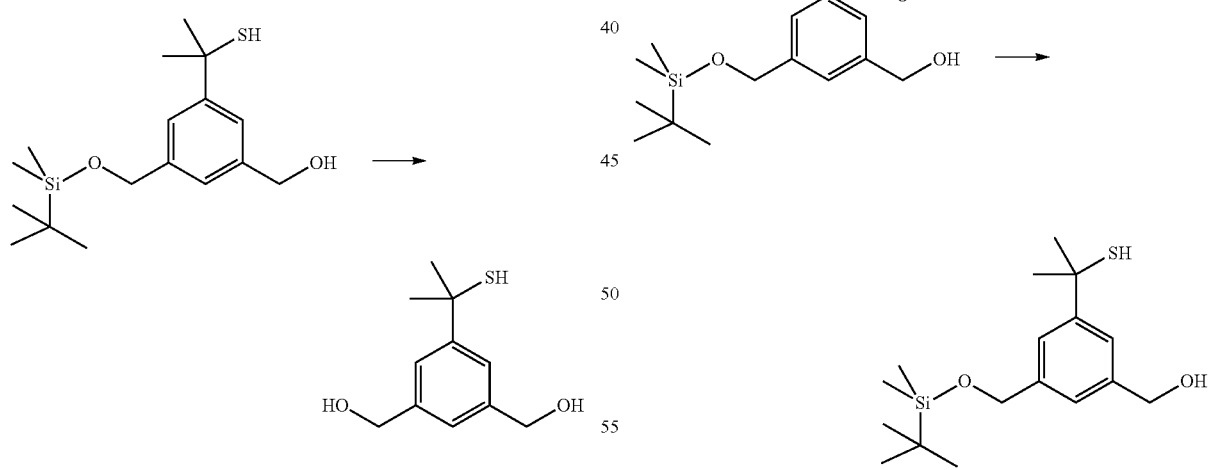

114 µl of hydrazine hydrate are added to 336 mg of 1-{3-[(tert-butyl)dimethylsilanyloxymethyl]-5-(hydroxymethyl)phenyl}-1-methylethyl thioacetate in solution in 3.7 ml of acetonitrile. After 3 h at AT, the mixture is concentrated under RP and the residue is purified by flash chromatography on silica (Biotage 25+M) using a gradient from 0 to 55% AcOEt in heptane. 230 mg of 5-hydroxymethyl-1-(1-mercapto-1-methylethyl)-3-[(tert-butyl)dimethylsilanyloxymethyl]benzene are thus obtained.

$^1$H NMR (400 MHz, d$_6$-DMSO): 0.08 (s, 6H); 0.92 (s, 9H); 1.76 (s, 6H); 3.19 (s, 1H); 4.48 (d, J=5.7 Hz, 2H); 4.71 (s, 2H); 5.14 (t, J=5.7 Hz, 1H); 7.10 (s, 1H); 7.33 to 7.42 (m, 2H). MS (C): CI: [M+NH$_4$]$^+$: m/z 344.

3.10. 1-[3-[(tert-butyl)dimethylsilanyloxymethyl]-5-(hydroxymethyl)phenyl]-1-methylethyl thioacetate

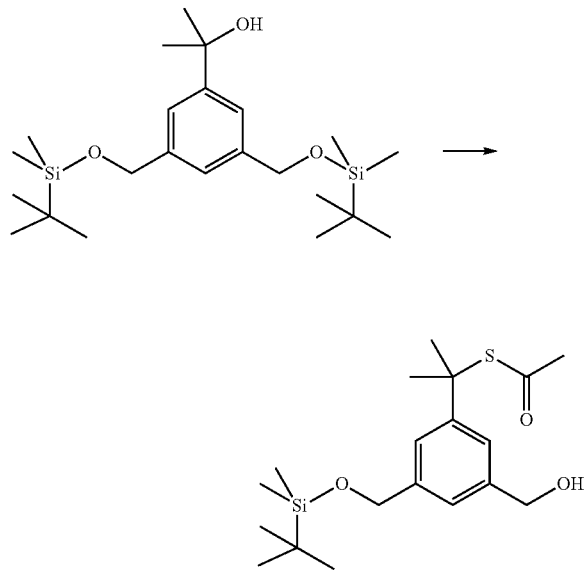

404 μl of thioacetic acid and 376 mg of zinc iodide are added to 1 g of 1-(1-hydroxy-1-methylethyl)-3,5-bis[(tert-butyl)dimethylsilanyloxymethyl]benzene in solution in 4.7 ml of 1,2-dichloroethane. The mixture is heated at 50° C. for 40 min. After returning to AT, the salts are removed by filtration, the organic phase is concentrated under RP and the residue is purified by flash chromatography on silica (Biotage 40+M) using a gradient from 0 to 30% AcOEt in heptane. 248 mg of 1-[3-[(tert-butyl)dimethylsilanyloxymethyl]-5-(hydroxymethyl)phenyl]-1-methylethyl thioacetate are thus obtained.

$^1$H NMR (400 MHz, d$_6$-DMSO): 0.08 (s, 6H); 0.91 (s, 9H); 1.79 (s, 6H); 2.17 (s, 3H); 4.48 (d, J=5.6 Hz, 2H); 4.70 (s, 2H); 5.16 (t, J=5.6 Hz, 1H); 7.11 (s, 1H); 7.33 (s, 1H); 7.35 (s, 1H). LC/MS (A): rt=1.23 min; [M+Na]$^+$: m/z 391.

3.11. 1-(1-Hydroxy-1-methylethyl)-3,5-bis[(tert-butyl)dimethylsilanyloxymethyl]benzene

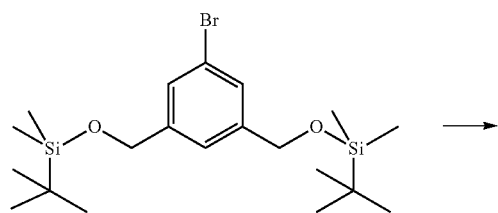

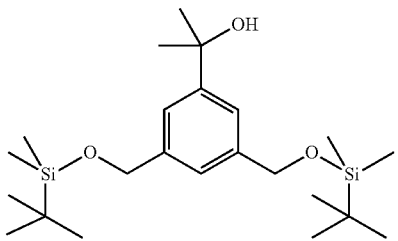

10.5 ml of n-BuLi as a 1.6M solution in hexane are added dropwise to 4.32 g of 1-bromo-3,5-bis[(tert-butyl)dimethylsilanyloxymethyl]benzene (G. T. Crisp and P. D. Turner, *Tetrahedron*, 2000, 56 (42), 8335) in solution in 150 ml of THF cooled to −71° C. After 1 h 30, 4.27 ml of acetone are added dropwise. The mixture is allowed to return to AT and then hydrolysed with a saturated aqueous NH$_4$Cl solution. The aqueous phase is extracted with 100 ml of AcOEt, the combined organic phases are dried over MgSO$_4$ and concentrated under RP, and the residue is purified by flash chromatography on silica (Biotage 65+M) using a gradient from 0 to 20% AcOEt in heptane. 2.48 g of 1-(1-hydroxy-1-methylethyl)-3,5-bis[(tert-butyl)dimethylsilanyloxymethyl]benzene are thus obtained.

$^1$H NMR (400 MHz, d-chloroform): 0.11 (s, 12H); 0.96 (s, 18H); 1.59 (s, 6H); 1.69 (s, 1H); 4.76 (s, 4H); 7.21 (s, 1H); 7.33 (s, 2H). LC/MS (B): rt=6.43 min; [M+Na]$^+$: m/z 447; base peak: m/z 407.

Example 4

4.1. Preparation of the Conjugate

A conjugate is prepared as for Ex. 1 by reacting hu2H11 and N-hydroxysuccinimidyl 3-{2-[2-(2-{2-[2-(4-{4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl]piperazin-1-yl}-1,1-dimethyl-4-oxobutylsulphanyl)acetylamino]ethoxy}ethoxy)ethoxy]ethoxy}propanoate. The conjugate obtained is quantitatively determined by spectrophotometry using the extinction coefficients e$_{320\,nm}$=7876 M$^{-1}$ cm$^{-1}$ and e$_{280\,nm}$=4334 M$^{-1}$ cm$^{-1}$ for the tomaymycin dimer and e$_{280\,nm}$=208 380 M$^{-1}$ cm$^{-1}$ for hu2H11: a mean of 3.13 tomaymycin dimers per antibody molecule was determined.

4.2. N-hydroxysuccinimidyl 3-{2-[2-(2-{2-[2-(4-(4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]-pyridin-4-yloxy)ethyl]piperazin-1-yl}-1,1-dimethyl-4-oxobutylsulphanyl) acetylamino]-ethoxy}ethoxy)ethoxy]ethoxy}propanoate Prepared according to Example 2 from 3-{2-[2-(2-{2-[2-(4-{4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl]piperazin-1-yl]-1,1-dimethyl-4-oxobutylsulphanyl)acetylamino]ethoxy}ethoxy)ethoxy]ethoxy}propanoic acid

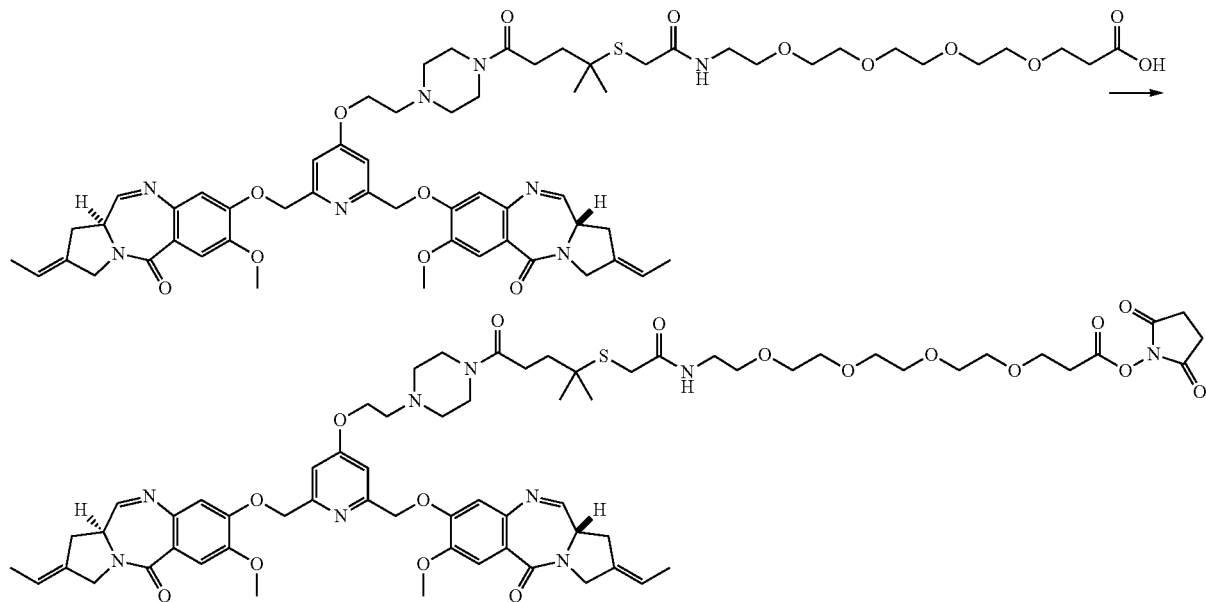

LC/MS (B): rt=3.27 min; [M+H]+: m/z 1309; [M+2H]2+: m/z 655.

4.3. 3-{2-[2-(2-{2-[2-(4-{4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl]piperazin-1-yl]-1,1-dimethyl-4-oxobutylsulphanyl)acetylamino]ethoxy}ethoxy)ethoxy]ethoxy}propanoic acid Prepared according to Example 2 from methyl 3-{2-[2-(2-{2-[2-(4-{4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl]piperazin-1-yl}-1,1-dimethyl-4-oxobutylsulphanyl)acetylamino]ethoxy}ethoxy)ethoxy]ethoxy}propanoate LC/MS (B): rt=3.16 min; [M+H]+: m/z 1212; [M+2H]2+: m/z 606.

4.4. Methyl 3-{2-[2-(2-{2-[2-(4-{4-[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl]-piperazin-1-yl}-1,1-dimethyl-4-oxobutylsulphanyl)acetylamino]ethoxy}ethoxy)ethoxy]-ethoxy}propanoate Prepared according to Example 2 from methyl 3-{2-[2-(2-{2-[2-(4-{4-[2-(2,6-bis(hydroxymethyl)pyridin-4-yloxy)ethyl]piperazin-1-yl}-1,1-dimethyl-4-oxobutylsulphanyl)acetylamino]ethoxy}ethoxy)ethoxy]ethoxy}propanoate

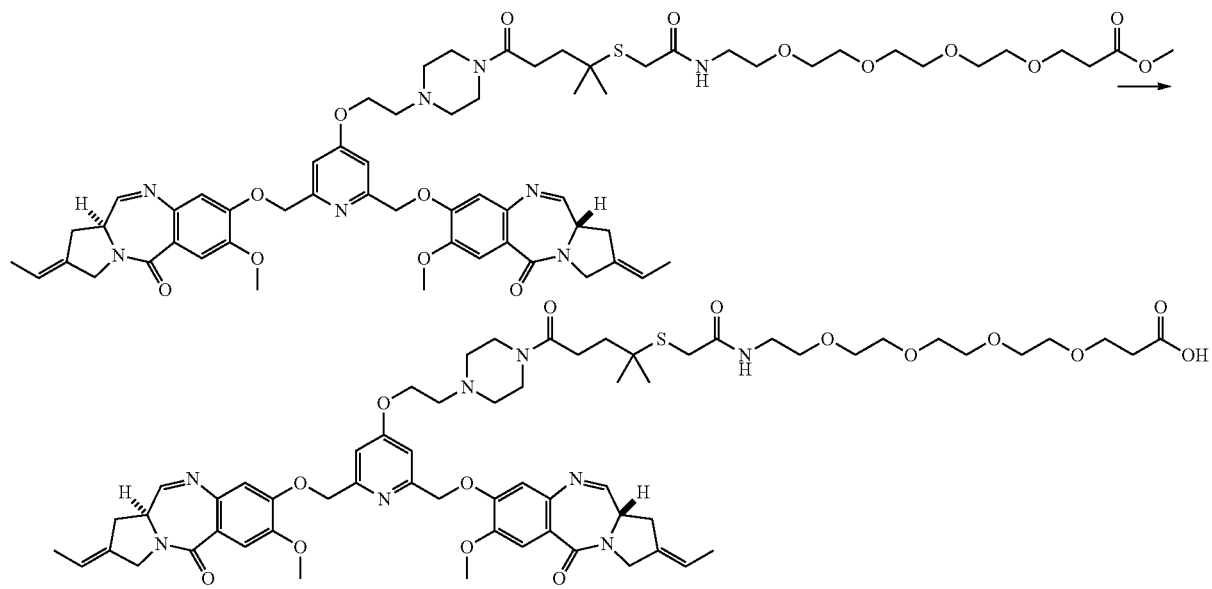

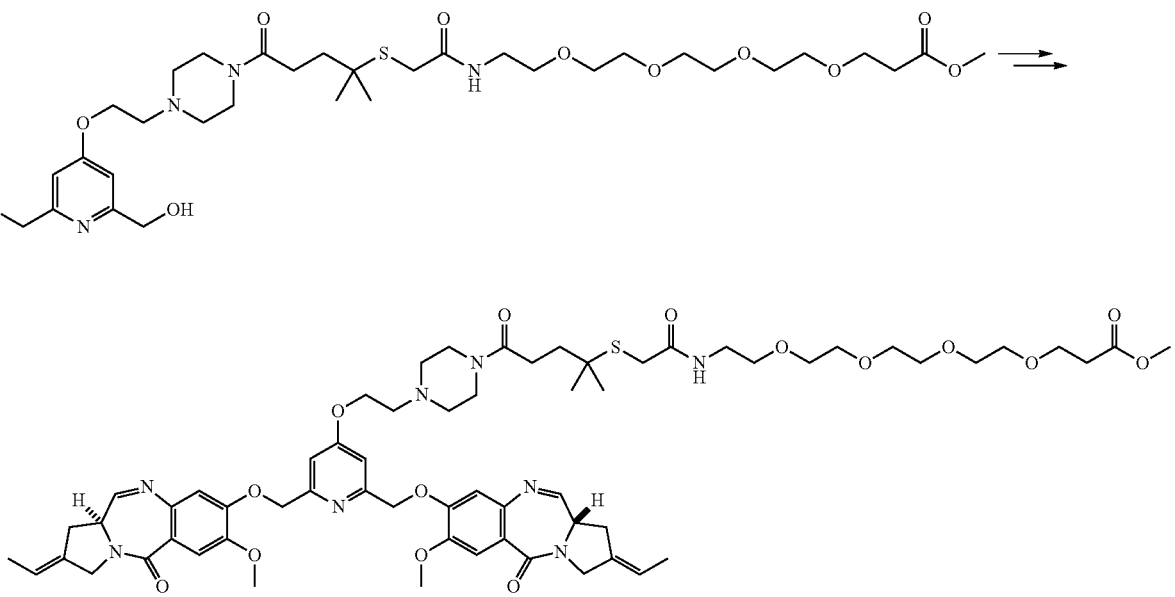

¹H NMR (500 MHz, d₆-DMSO): 1.22 (s, 6H); 1.69 (m, 8H); 2.37 (m, 2H); 2.40 (m, 2H); 2.48 (m, 2H); 2.53 (t, J=6.1 Hz, 2H); 2.72 (m, 2H); 2.92 (m, 2H); 3.04 (m, 2H); 3.11 (s, 2H); 3.19 (q, J=5.4 Hz, 2H); 3.39 (t, J=5.4 Hz, 2H); 3.42 (m, 4H); 3.49 (m, 12H); 3.59 (s, 3H); 3.62 (t, J=6.1 Hz, 2H); 3.86 (s, 6H); 3.88 (m, 2H); 4.10 (m, 4H); 4.22 (m, 2H); 5.17 (d, J=13.0 Hz, 2'H); 5.22 (d, J=13.0 Hz, 2H); 5.55 (m, 2H); 6.94 (s, 2H); 7.09 (s, 2H); 7.38 (s, 2H); 7.77 (d, J=3.9 Hz, 2H); 8.01 (t, J=5.4 Hz, 1H). LC/MS (B): rt=3.30 min; [M+H]⁺: m/z 1225; [M+2H]²⁺: m/z 613 (base peak).

4.5. Methyl 3-{2-[2-(2-{2-[2-(4-{4-[2-(2,6-bis(hydroxymethyl)pyridin-4-yloxy)ethyl]piperazin-1-yl}-1,1-dimethyl-4-oxobutylsulphanyl)acetylamino]ethoxy}ethoxy)ethoxy]ethoxy}-propanoate Prepared according to Example 2 from 4-(2-[4-(4-mercapto-4-methylpentanoyl)piperazin-1-yl]ethoxy)-2,6-bis(hydroxymethyl)pyridine ¹H NMR (500 MHz, d₆-DMSO): all the signals are broad with 1.22 (s, 6H); 1.71 (m, 2H); 2.20 to 2.58 (partially masked m, 8H); 2.75 (m, 2H); 3.12 (m, 2H); 3.19 (m, 2H); 3.47 to 3.53 (m, 18H); 3.60 (m, 5H); 4.18 (m, 2H); 4.46 (m, 4H); 5.31 (m, 2H); 6.86 (s, 2H); 8.00 (m, 1H). LC/MS (B): rt=2.20 min; [M+H]⁺: m/z 717; [M−H+HCO₂H]⁻: m/z 761.

4.6. 4-(2-[4-(4-mercapto-4-methylpentanoyl)piperazin-1-yl]ethoxy)-2,6-bis(hydroxymethyl)pyridine Prepared according to Example 2 from 4-(2-[4-(4-methyl-4-(methyldisulphanyl)pentanoyl)piperazin-1-yl]ethoxy)-2,6-bis(hydroxymethyl)pyridine

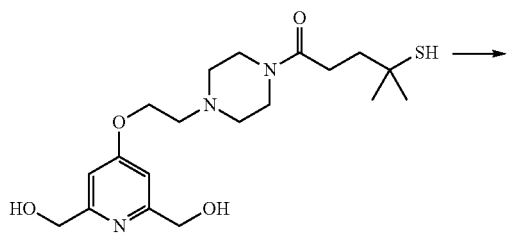

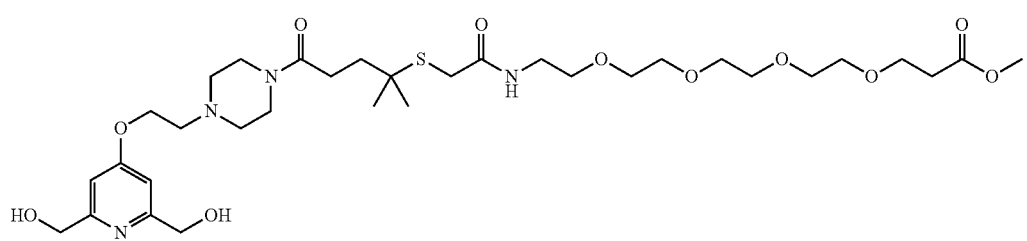

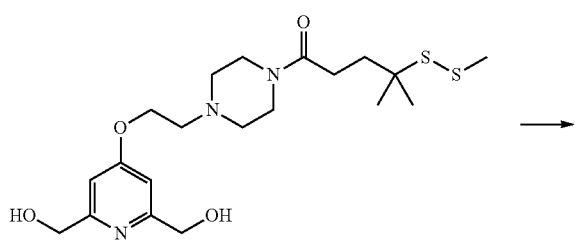

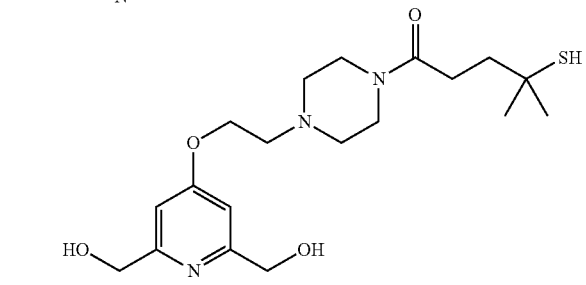

¹H NMR (400 MHz, d₆-DMSO): 1.32 (s, 6H); 1.76 (m, 2H); 2.36 to 2.53 (partially masked m, 6H); 2.66 (s, 1H); 2.75 (t, J=5.5 Hz, 2H); 3.40 to 3.52 (m, 4H); 4.18 (t, J=5.5 Hz, 2H); 4.46 (s, 4H); 5.30 (very broad m, 2H); 6.86 (s, 2H). LC/MS (B): rt=0.76 min; [M+H]⁺: m/z 398; [M−H]⁻: m/z 396.

4.7. 4-(2-[4-(4-methyl-4-(methyldisulphanyl)pentanyl)piperazin-1-yl]ethoxy)-2,6-bis(hydroxymethyl)pyridine

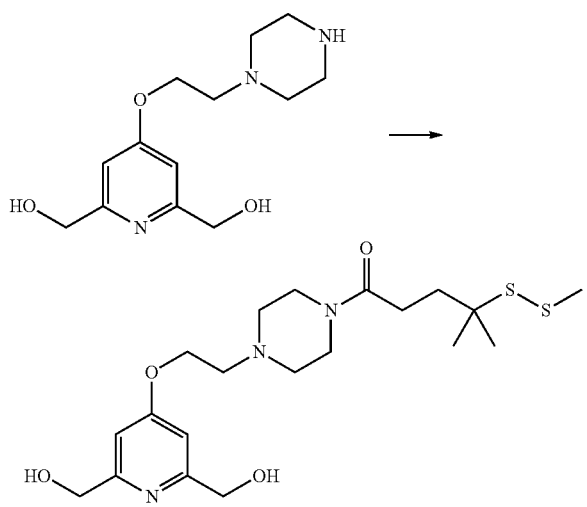

344 µL of TEA and then, after stirring for 10 min, 748 mg of 4-methyl-4-(methyldisulphanyl)pentanoic acid, 417 µl of diisopropylcarbodiimide and 69 mg of 1-hydroxybenzotriazole hydrate are added to 600 mg of 4-[2-(piperazin-1-yl)ethoxy]-2,6-bis(hydroxymethyl)pyridine in solution in 12 ml of DMF. After 15 h at AT, the mixture is concentrated under RP, 15 ml of water are added and extraction is carried out 2× with AcOEt. The combined organic phases are dried over MgSO₄ and concentrated under RP, and the residue is purified by flash chromatography on silica (Analogix Super Flash SiO₂ SF25-80 g) using a gradient from 2 to 10% of MeOH in DCM. 390 mg of 4-(2-[4-(4-methyl-4-(methyldisulphanyl)pentanoyl)piperazin-1-yl]ethoxy)-2,6-bis(hydroxymethyl)pyridine are thus obtained.

¹H NMR (400 MHz, d₆-DMSO): 1.26 (s, 6H); 1.79 (m, 2H); 2.36 (m, 2H); 2.39 (s, 3H); 2.40 to 253 (partially masked m, 4H); 2.75 (t, J=5.6 Hz, 2H); 3.45 (m, 4H); 4.18 (t, J=5.6 Hz, 2H); 4.46 (d, J=5.9 Hz, 4H); 5.30 (t, J=5.9 Hz, 2H); 6.86 (s, 2H). LC/MS (A): rt=0.42 min; [M+H]⁺: m/z 444; [M−H+HCO₂H]⁻: m/z 488.

4.8. 4-[2-(piperazin-1-yl)ethoxy]-2,6-bis(hydroxymethyl)pyridine 19 ml of a 4M solution of HCl in dioxane are added to 2.3 g of 4-(2-(4-(tert-butoxycarbonyl)piperazin-1-yl)ethoxy)-2,6-bis(hydroxymethyl)pyridine in solution in 33 ml of dioxane. After 12 h at AT, the resulting precipitate is recovered by filtration on a sintered glass funnel, taken up in MeOH and then concentrated under RP, and the residue is diluted in 40 ml of an MeOH/water 1/1 mixture. The resulting solution is deposited on Mega BE-SCX, 25GM 150ML (Varian). After washing the phase with MeOH, the product of interest is eluted with a 2N solution of ammonia in methanol. The MeOH/NH₃ phase is concentrated under RP. 1.6 g of 4-[2-(piperazin-1-yl)ethoxy]-2,6-bis(hydroxymethyl)pyridine are thus obtained.

¹H NMR (400 MHz, d₆-DMSO): 2.40 (m, 4H); 2.68 (m, 6H); 4.15 (t, J=5.7 Hz, 2H); 4.44 (m, 4H); 5.29 (m, 2H); 6.85 (s, 2H). LC/MS (A): rt=0.10 min; [M+H]⁺: m/z 268; [M+2H] 2⁺: m/z 134.5; base peak: m/z 113.

4.9. 4-(2-(4-(tert-butoxycarbonyl)piperazin-1-yl)ethoxy)-2,6-bis(hydroxymethyl)pyridine

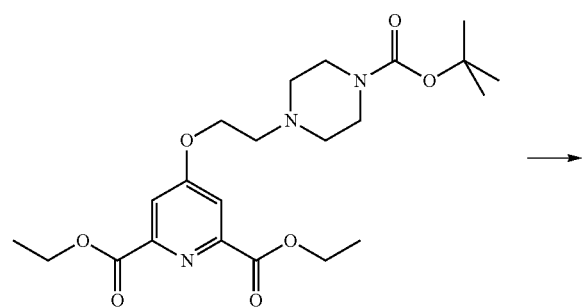

-continued

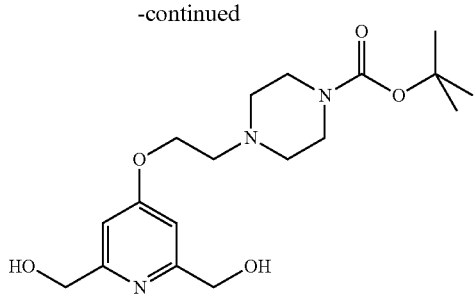

779 mg of sodium borohydride and 2.29 g of CaCl$_2$ are added to 3.1 g of diethyl 412-(4-(tert-butoxycarbonyl)piperazin-1-yl)ethoxy]pyridine-2,6-dicarboxylate in solution in 105 ml of EtOH. After 3 h at AT, the mixture is hydrolysed and concentrated under RP. Water is added to the residue obtained and the resulting aqueous phase is extracted 4× with AcOEt. The combined organic phases are washed with a saturated aqueous NaCl solution and then concentrated under RP. 2.4 g of 4-(2-(4-(tert-butoxycarbonyl)piperazin-1-yl)ethoxy)-2,6-bis(hydroxymethyl)pyridine are thus obtained.

$^1$H NMR (400 MHz, d$_6$-DMSO): 1.39 (s, 9H); 2.43 (m, 4H); 2.73 (t, J=5.6 Hz, 2H); 3.30 (partially masked m, 4H); 4.17 (t, J=5.6 Hz, 2H); 4.45 (d, J=5.9 Hz, 4H); 5.30 (t, J=5.9 Hz, 2H); 6.86 (s, 2H). LC/MS (A): rt=0.24 min; [M+H]$^+$: m/z 368.

4.10. Diethyl 4-[2-(4-(tert-butoxycarbonyl)piperazin-1-yl)ethoxy]pyridine-2,6-dicarboxylate

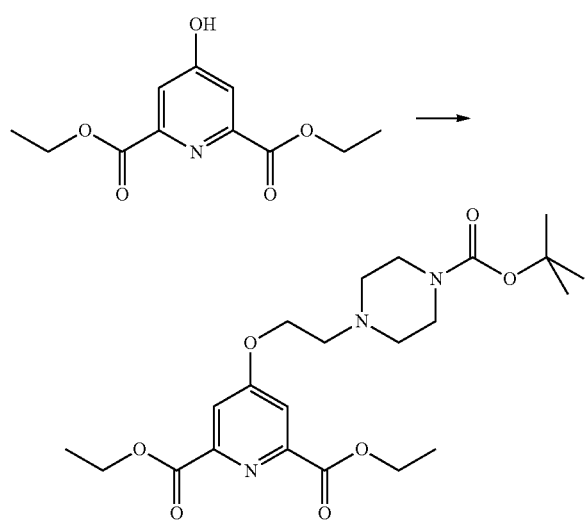

4.5 ml of TEA and then 2 ml of methanesulphonyl chloride are added to a solution, cooled to 0° C., of 5 g of 1-(tert-butoxycarbonyl)-4-(2-hydroxyethyl)piperazine in 102 ml of DCM. After 1 h, the mixture is brought back to AT. After stirring for an additional 1 h, the mixture is hydrolysed and the organic phase is washed 2× with water, then dried over MgSO$_4$ and concentrated under RP. 140 ml of DMF are added to the residue thus obtained (6.7 g) and the mixture is brought to 60° C. 190 mg of the diethyl ester of chelidamic acid (Scrimin P., Tecilla P., Tonellato U. and Vendrame T. J., Org. Chem., 1989, 54, 5988) and 549 mg of K$_2$CO$_3$ are then added and the mixture is heated at 80° C. for 20 h. After concentrating under RP, the mixture is hydrolysed and extracted 3× with AcOEt, the combined organic phases are washed with a saturated NaCl solution and concentrated under RP, and the residue is purified by flash chromatography on silica (Analogix Super Flash SiO$_2$ SF25-150 g) using a gradient from 60 to 85% of AcOEt in heptane. 3.1 g of diethyl 4-[2-(4-(tert-butoxycarbonyl)piperazin-1-yl)ethoxy]pyridine-2,6-dicarboxylate are thus obtained.

$^1$H NMR (400 MHz, d$_6$-DMSO): 1.34 (t, J=7.2 Hz, 6H); 1.39 (s, 9H); 2.44 (m, 4H); 2.76 (t, J=5.7 Hz, 2H); 3.30 (partially masked m, 4H); 4.34 (t, J=5.7 Hz, 2H); 4.38 (q, J=7.1 Hz, 4H); 7.74 (s, 2H). LC/MS (B): rt=2.81 min; [M+H]$^+$: m/z 452; [MH+HCO$_2$H]$^-$: m/z 496.

Example 5

5.1. 4-{2-[4-(2-Methyl-2-(methyldisulphanyl)propyl)piperazin-1-yl]ethoxy}-2,6-bis(hydroxymethyl)pyridine Prepared according to Example 1 from 4-[2-(piperazin-1-yl)ethoxy]-2,6-bis(hydroxymethyl)pyridine.

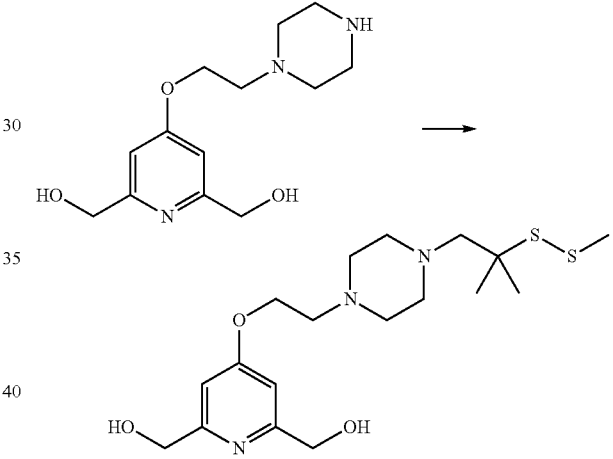

$^1$H NMR (400 MHz, d$_6$-DMSO): 1.25 (s, 6H); 2.39 (s, 3H); 2.40 (s, 2H); 2.44 to 2.57 (partially masked m, 8H); 2.69 (t, J=5.7 Hz, 2H); 4.14 (t, J=5.7 Hz, 2H); 4.45 (d, J=5.7 Hz, 4H); 5.29 (t, J=5.7 Hz, 2H); 6.85 (s, 2H). LC/MS (B): rt=0.51 min; [M+H]$^+$: m/z 402.

Example 6

6.1. Preparation of the Conjugate

A conjugate is prepared as for Ex. 1 by reacting hu2H11 and N-hydroxysuccinimidyl 3-{2-[2-(2-{2-[2-(2-{[2-(2,6-bis[(S)-2-eth-(E)-ylidene-7-methoxy-1,2,3,11a-tetrahydro-pyrrolo[2,1-c][1,4]benzodiazepin-5-one-8-yloxymethyl]pyridin-4-yloxy)ethyl]methyl)amino}-1,1-dimethylethylsulphanyl)acetyl(methyl)amino]ethoxy}ethoxy)ethoxy]ethoxy}propanoate. The conjugate obtained is quantitatively determined by spectrophotometry using the extinction coefficients $e_{319\ nm}$=7789 M$^{-1}$ cm$^{-1}$ and $e_{280\ nm}$=4362 M$^{-1}$ cm$^{-1}$ for the tomaymycin dimer and $e_{280\ nm}$=208 380 M$^{-1}$ cm$^{-1}$ for hu2H11: a mean of 2.90 tomaymycin dimers per antibody of molecule was determined.

6.2. N-hydroxysuccinimidyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetyl(methyl)amino]ethoxy}ethoxy)ethoxy]ethoxy}propanoate Prepared according to Example 2 from 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino)-1,1-dimethylethylsulphanyl)acetyl(methyl)amino]ethoxy}ethoxy)ethoxy]ethoxy}propanoic acid:

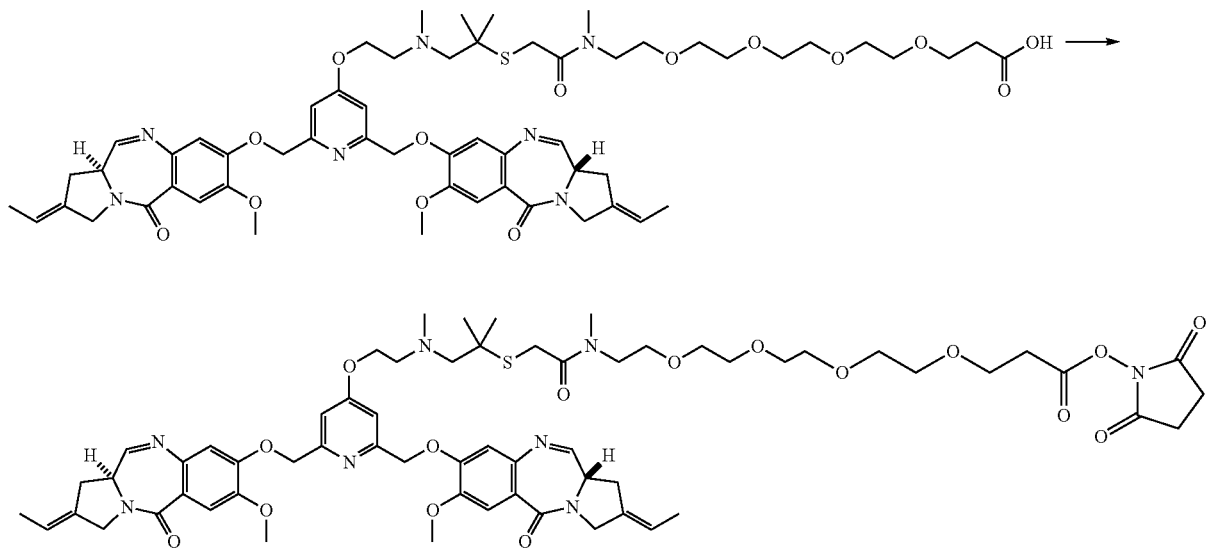

LC/MS (F): rt=1.02 min; [M+H]$^+$: m/z 1225; [M+H$_2$O+H]$^+$: m/z 1243

6.3. 3-{2-[2-(2-{2-[2-(2-{[2-(2,6-bis[(S)-2-Eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetyl(methyl)amino]ethoxy}ethoxy)ethoxy]ethoxy}propanoic acid Prepared according to Ex. 2 from methyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetyl(methyl)amino]ethoxy}ethoxy)ethoxy]ethoxy}propanoate:

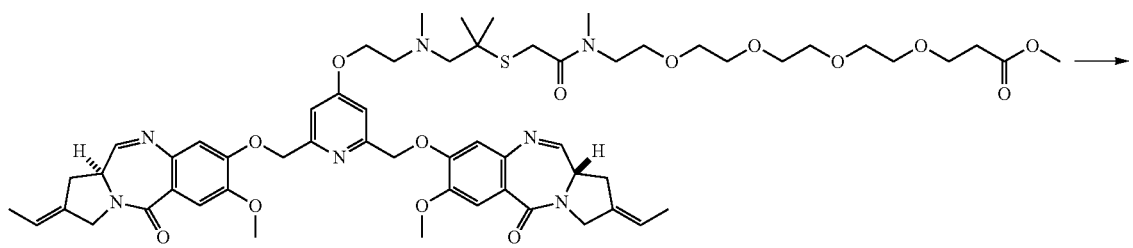

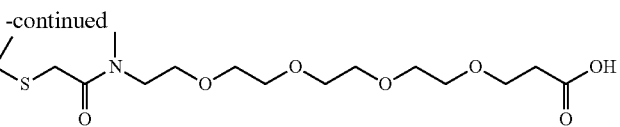
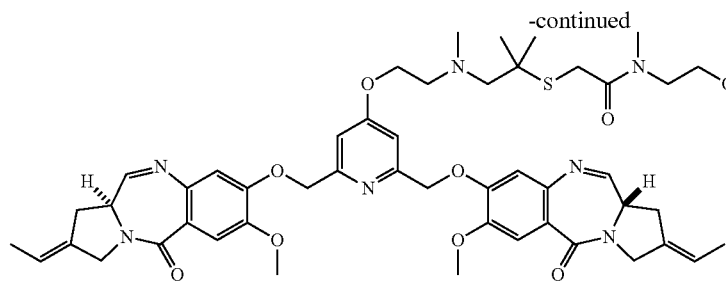

LC/MS (F): rt=0.97 min; [M+H]+: m/z 1129

6.4. Methyl 3-{2-[2-(2-{2-[2-(2-{[2-(2,6-bis[(S)-2-eth-(E)-ylidene-7-methoxy-1,2,3,11a-tetrahydropyrrolo[2,1-c][1,4]benzodiazepin-5-one-8-yloxymethyl]pyridin-4-yloxy)ethyl](methyl)amino}-1,1-dimethylethylsulphanyl)acetyl(methyl)amino]ethoxy}-ethoxy)ethoxy]ethoxy}propanoate Prepared according to Ex. 2 from methyl 3-{2-[2-(2-{2-[2-(2-{[2-(2,6-bis(hydroxymethyl)pyridin-4-yloxy)ethyl](methyl)amino}-1,1-dimethylethylsulphanyl)acetyl(methyl)amino]ethoxy}ethoxy)ethoxy]ethoxy}propanoate:

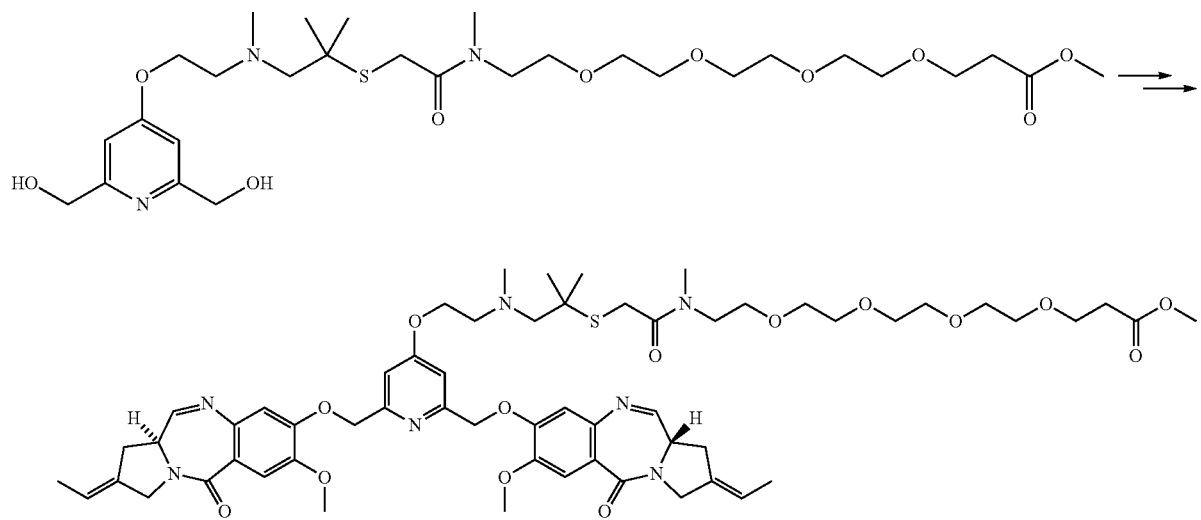

¹H NMR (500 MHz, d₆-DMSO): the absorptions are broad with 1.20 (s, 6H); 1.58 to 1.73 (m, 6H); 2.38 (s, 3H); 2.52 to 3.07 (m, 13H); 3.36 to 3.63 (m, 23H); 3.67 to 3.91 (m, 8H); 4.06 to 4.26 (m, 6H); 5.02 to 5.26 (m, 4H); 5.33 to 5.60 (m, 2H); 6.39 to 7.42 (m, 6H); 7.76 (m, 2H).

LC/MS (A): rt=0.77 min; [M+H]+: m/z 1142; [M+2H]²⁺: m/z 571.5 (base peak).

6.5. Methyl 3-{2-[2-(2-{2-[2-(2-{[2-(2,6-bis(hydroxymethyl)pyridin-4-yloxy)ethyl](methyl)amino}-1,1-dimethylethylsulphanyl)acetyl(methyl)amino]ethoxy}ethoxy)ethoxy]ethoxy}-propanoate Prepared according to Ex. 2 from methyl 3-{2-[2-(2-{2-[(2-iodoacetyl)(methyl)amino]ethoxy}-ethoxy)ethoxy]ethoxy}propanoate:

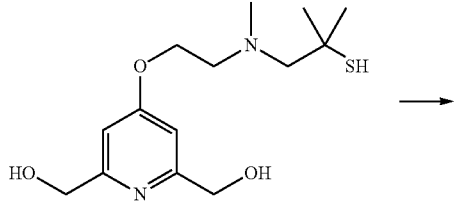

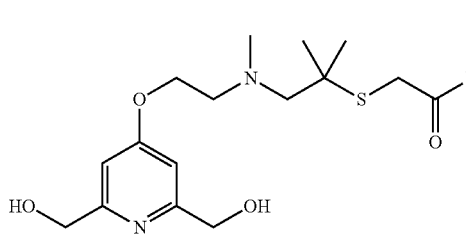

$^1$H NMR (400 MHz, d$_6$-DMSO): 50/50 resolution of rotamers with: 1.22 (s, 3H); 1.24 (s, 3H); 2.41 (s, 3H); 2.53 (t, J=6.2 Hz, 2H); 2.56 (m, 2H); 2.80 (s, 1H); 2.88 (t, J=5.9 Hz, 2H); 3.05 (s, 2H); 3.35 to 3.58 (m, 18H); 3.59 (s, 3H); 3.62 (t, J=6.2 Hz, 2H); 4.13 (t, J=5.9 Hz, 2H); 4.45 (d, J=5.9 Hz, 4H); 5.29 (t, J=5.9 Hz, 2H); 6.85 (s, 2H). LC/MS (B): rt=2.18 min; [M+H]$^+$: m/z 634; [M−H+HCO$_2$H]$^−$: m/z 678.

6.6. Methyl 3-{2-[2-(2-{2-[(2-iodoacetyl)(methyl)amino]ethoxy}ethoxy)ethoxy]ethoxy}-propanoate

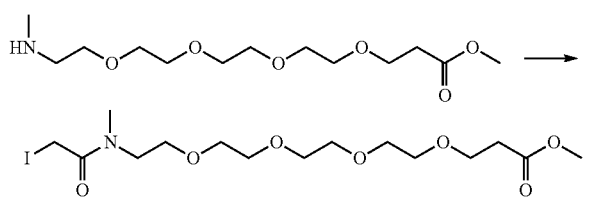

117.4 mg of N-hydroxysuccinimidyl iodoacetate in solution in 6.5 ml of DCM are added to 215 mg of methyl 3-(2-{2-[2-(2-(methylamino)ethoxy)ethoxy]ethoxy}ethoxy)propanoate. After 2 h at AT, the mixture is concentrated under RP and the residue is purified by flash chromatography on silica (Analogix Super Flash SiO$_2$ SF25-24 g) using a gradient from 0 to 6% of MeOH in DCM. 210 mg of methyl 3-{2-[2-(2-{2-[(2-iodoacetyl)(methyl)amino]ethoxy}ethoxy)ethoxy]ethoxy}-propanoate are thus obtained. $^1$H NMR (400 MHz, d$_6$-DMSO): 55/45 resolution of rotamers with 2.54 (t, J=6.2 Hz, 2H); 2.83 (s, 1.35H); 3.02 (s, 1.65H); 3.36 to 3.55 (m, 16H); 3.60 (s, 3H); 3.63 (t, J=6.2 Hz, 2H); 3.83 (s, 1.1H); 3.88 (s, 0.9H). LC/MS (A): rt=0.62 min; [M+H]$^+$: m/z 462.

6.7. Methyl 3-(2-{2-[2-(2-(methylamino)ethoxy)ethoxy]ethoxy}ethoxy)propanoate

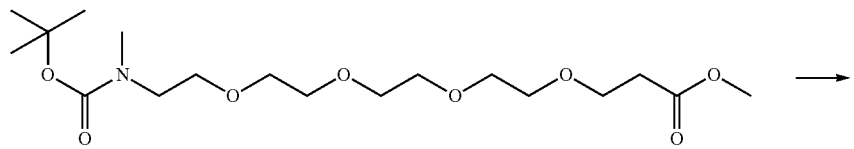
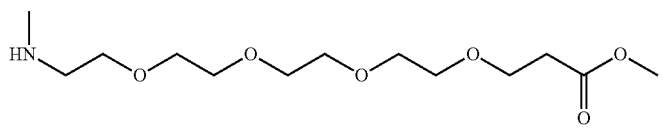

3 ml of a 4M solution of HCl in dioxane are added to 390 mg of methyl 3-[2-(2-{2-[2-((tert-butoxycarbonyl)(methyl)amino)ethoxy]ethoxy}ethoxy)ethoxy]propanoate in solution in 5.3 ml of dioxane. After 12 h at AT, the mixture is concentrated under RP and the residue is dissolved in a minimum of methanol and deposited on Mega BE-SCX, 10GM 60ML (Varian). After washing the phase with MeOH, the product of interest is eluted with a 2N solution of ammonia in methanol. The methanol/NH$_3$ phase is concentrated under RP. 270 mg of methyl 3-(2-{2-[2-(2-(methylamino)ethoxy)ethoxy]ethoxy}ethoxy)propanoate are thus obtained. $^1$H NMR (400 MHz, d$_5$-DMSO): 2.28 (s, 3H); 2.54 (t, J=6.2 Hz, 2H); 2.59 (t, J=5.9 Hz, 2H); 3.44 (t, J=5.9 Hz, 2H); 3.47 to 3.54 (m, 12H); 3.60 (s, 3H); 3.63 (t, J=6.2 Hz, 2H). LC/MS (A) (ELSD): rt=0.30 min; [M+H]$^+$: m/z 294.

6.8. Methyl 3-[2-(2-{2-[2-((tert-butoxycarbonyl)(methyl)amino)ethoxy]ethoxy}ethoxy)ethoxy]propanoate

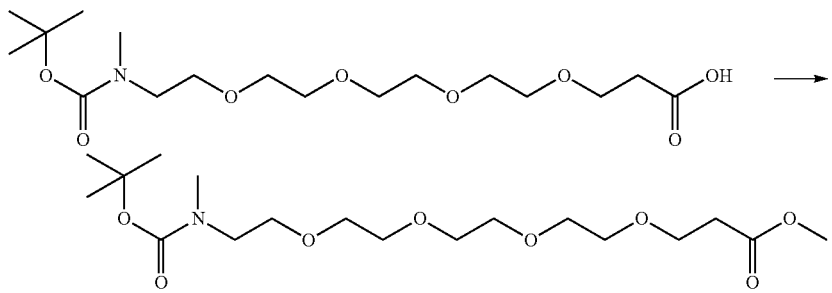

2 ml of a 2M solution of trimethylsilyldiazomethane in hexane are added to a solution, cooled to 0° C., of 500 mg of 3-[2-(2-{2-[2-((tert-butoxycarbonyl)(methyl)amino)ethoxy]ethoxy}ethoxy)ethoxy]propanoic acid in 4.8 ml of MeOH. After 2 h, the mixture is neutralized by addition of 120 µl of acetic acid and then concentrated under RP, and the residue is purified by flash chromatography on silica (Analogix Super Flash $SiO_2$ SF25-40 g) using a gradient from 0 to 5% of methanol in DCM. 400 mg of methyl 3-[2-(2-{2-[2-((tert-butoxycarbonyl)(methyl)amino)ethoxy]ethoxy}ethoxy)ethoxy]propanoate are thus obtained.

$^1$H NMR (400 MHz, $d_6$-DMSO): 1.38 (s, 9H); 2.54 (t, J=6.2 Hz, 2H); 2.80 (broad s, 3H); 3.29 (partially masked t, J=5.9 Hz, 2H); 3.45 to 3.55 (m, 14H); 3.59 (s, 3H); 3.63 (t, J=6.2 Hz, 2H). LC/MS (A): rt=0.84 min; [M+Na]$^+$: m/z 416 (base peak); LC/MS (A): rt=0.84 min; [M+Na]$^+$: m/z 416 (base peak).

6.9. 3-[2-(2-{2-[2-((tert-Butoxycarbonyl)(methyl)amino)ethoxy]ethoxy}ethoxy)ethoxy]-propanoic acid

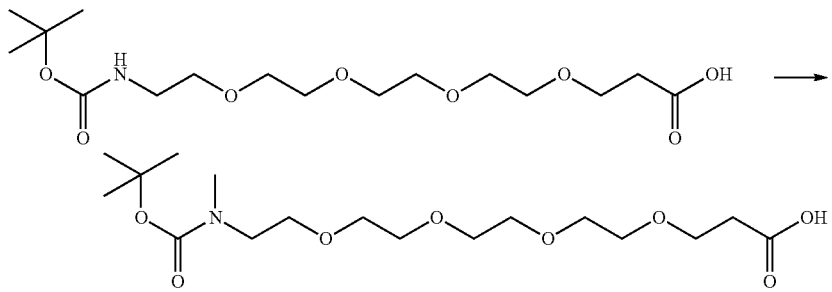

85.4 mg of NaH are added portionwise to a solution, cooled to 0° C., of 520 mg of 3-[2-(2-{2-[2-((tert-butoxycarbonyl)amino)ethoxy]ethoxy}ethoxy)ethoxy]propanoic acid in 14 ml of THF. After stirring for 5 min, 150 µl of iodomethane are added. The mixture is then stirred at AT for 2 h and then an additional 150 µl of iodomethane are added. After 12 h at AT, the mixture is hydrolysed and then brought to acidic pH by addition of aqueous acetic acid at 0° C. The aqueous phase is extracted 3× with AcOEt, the combined organic phases are dried over $MgSO_4$ and concentrated under RP, and the crude product obtained is reacted again according to the same protocol with 85 mg of NaH and 176 µl of iodomethane for an additional 2 h. 500 mg of 3-[2-(2-{2-[2-((tert-butoxycarbonyl)(methyl)amino)ethoxy]ethoxy}ethoxy)ethoxy]propanoic acid are thus obtained.

LC/MS (F): rt=1.01 min; [M+H]$^+$: m/z 380.

Evaluation of the Inhibition of the Proliferation of the MDA-MB-231, MDA-A1 and HCT116 Cell Lines by the Compounds of Formula IA with $Z_bR_b$=–OMe and Y=Y'=–OMe The MDA-MB-231, MDA-A1 or HCT116 cells in their exponential growth phase are trypsinized and resuspended in their respective culture medium (DMEM/F12 Gibco #21331, 10% FCS Gibco #10500-056, 2 nM glutamine Gibco #25030 for the MDA cells; DMEM Gibco #11960, 10% FCS Gibco #10500-056, 2 mM glutamine Gibco #25030 for the HCT116 cells). The cell suspension is seeded in Cytostar 96-well culture plates (GE Healthcare Europe, #RPNQ0163) in the complete culture medium containing serum at a density of 5000 cells/well (MDA-MB-231, MDA-A1, HCT116). After incubation for 4 hours, successive dilutions of the tomaymycin dimers are added to the wells in triplicate for each concentration. The cells are cultured for 3 days at 37° C. under an atmosphere containing 5% $CO_2$ in the presence of the cytotoxic agents. On the 4$^{th}$ day, 10 µl of a $^{14}$C-thymidine solution (0.1 µCi/well, Perkin Elmer #NEC56825000) are added to each well. The incorporation of $^{14}$C-thymidine is measured 96 hours after the start of the experiment using a MicroBeta radioactivity counter (Perkin Elmer). The data are expressed in the form of a % of survival by determining the ratio between the count obtained with the cells treated with the cytotoxic agent and the count obtained with the cells of the control wells (treated with the culture medium alone).

TABLE II

Inhibition of the proliferation ($^{14}$C-thymidine pulse at 96 h)

| Structure of the compound of formula (IA) | HCT116 | IC$_{50}$ [nM] MDA-A1 | MDA-MB231 |
|---|---|---|---|
| | 0.030 | 1.991 | 0.009 |
| | 0.120 | 2.260 | 0.070 |
| | 0.127 | >10 | 0.084 |

TABLE II-continued
Inhibition of the proliferation ($^{14}$C-thymidine pulse at 96 h)
| Structure of the compound of formula (IA) | IC$_{50}$ [nM] | | |
|---|---|---|---|
| | HCT116 | MDA-A1 | MDA-MB231 |
| 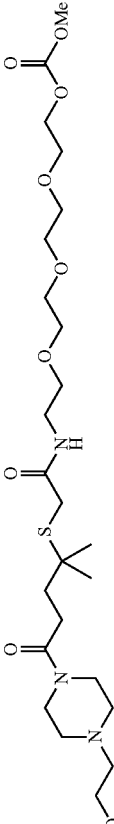 | 1.250 | >10 | 0.450 |

It is found that the test compounds for which $Z_bR_b$=—OMe have a powerful anticancer activity; this allows it to be supposed that the similar compounds characterized by another $Z_bR_b$ group are liable to exhibit an identical activity.

Evaluation of the Inhibition of the Proliferation of the MDA-MB-231 Cell Lines by the hu2H11-Cytotoxic Agent Conjugates MDA-MB-231 cells in their exponential growth phase are trypsinized and resuspended in their culture medium (DMEM/F12 Gibco #21331, 10% FCS Gibco #10500-056, 2 nM glutamine Gibco #25030). The cell suspension is seeded in Cytostar 96-well culture plates (GE Healthcare Europe, #RPNQ0163) in the complete culture medium containing serum at a density of 5000 cells/well. After incubation for 4 hours, successive dilutions of the antibody-cytotoxic agent immunoconjugates are added to the wells at concentrations decreasing from $10^{-7}$ to $10^{-12}$ M (in triplicate for each concentration). The cells are cultured at 37° C. in an atmosphere containing 5% $CO_2$ in the presence of the antibody-cytotoxic agent immunoconjugates for 3 days. On the $4^{th}$ day, 10 μl of a $^{14}$C-thymidine solution (0.1 μCi/well, Perkin Elmer #NEC56825000) are added to each well. The incorporation of $^{14}$C-thymidine is measured 96 hours after the start of the experiment with a MicroBeta radioactivity counter (Perkin Elmer). The data are expressed in the form of a % of survival by determining the ratio between the count obtained with the cells treated with the immunoconjugate and the count obtained with the cells of the control wells (treated with the culture medium alone). In certain experiments*, the naked antibody hu2H11 was added to the wells at a concentration of 1 μM at the start of the experiment and the inhibition of the proliferation was measured as described above.

TABLE III

Inhibition of the proliferation ($^{14}$C-thymidine pulse at 96 h)

| Structure | IC$_{50}$ [pM] | | IC$_{50}$ ratio |
|---|---|---|---|
| | Mean IC$_{50}$ | Mean IC$_{50}$ (+naked hu2H11*) | |
| [structure 1] | 31 | 540 | 17 |
| [structure 2] | 910 | 5095 | 6 |
| [structure 3] | 54 | 3981 | 74 |

TABLE III-continued

Inhibition of the proliferation ($^{14}$C-thymidine pulse at 96 h)

| Structure | IC$_{50}$ [pM] | | IC$_{50}$ ratio |
|---|---|---|---|
| | Mean IC$_{50}$ | Mean IC$_{50}$ (+naked hu2H11*) | |
| (structure 1) | 1255 | 9125 | 7 |
| (structure 2) | 68.5 | 1119 | 16 |

Monomer Stability of the Noncleavable Tomaymycin Dimer Conjugates

The noncleavable hu2H11 conjugates prepared with tomaymycin dimers described in Examples 3 and 5 of International Application WO 09016516 have a tendency to experience a decrease in their monomer purity over time after storing for several months at 3-5° C. Specifically, these conjugates, formulated in an aqueous buffer at pH 6.5 with a histidine concentration of 10 mM containing 10% of sucrose and 5% of NMP, exhibiting a mean of 3 to 3.5 tomaymycin dimers per antibody molecule, with an initial monomer purity of the order of 97.5%, can decline in monomer purity by 6 to 15% in 6 to 8 months. This phenomenon was not observed with the conjugate of Example 3 which, with a mean of 3.5 tomaymycin dimers per antibody molecule, retains a monomer purity of greater than 99% in 4 months under the same storage conditions, thus suggesting a better stability of this particular conjugate. This is a general objective desired in the field of conjugates to be able to have available a conjugate which retains a monomer purity over time.

Evaluation of the Antitumour Activity of hu2H11-Cytotoxic Agent Conjugates on Female SCID Mice Carrying an Advanced Human Breast Adenocarcinoma, MDA-MB-231

Two conjugates of the same antibody hu2H11, denoted C1 (prepared with the tomaymycin dimer described in Example 5 of International Application WO 09016516) and C2 (conjugate of Example 3), were evaluated at 4 dose levels on measurable mammary tumours MDA-MB-231 implanted s.c. on female SCID mice. The control groups were not treated. The doses of the two conjugates are given in µg of tomaymycin dimer/kg. They were administered at 80, 40, 20 and 10 µg/kg by injection of intravenous (IV) bolus type on day 13 for C1 and on day 24 for C2.

As regards the evaluation of the antitumour activity of the conjugates, the animals were weighed daily and the tumours were measured twice weekly using a calliper rule. The antitumour activity was evaluated at the Maximum Tolerated Dose (MTD). A dose producing a loss in weight of 20% at nadir or 10% (or more) mortality linked to the conjugate is regarded as being toxic. The body weight of the animals includes the weight of the tumours. The weight of the tumours is calculated according to the formula: weight (mg)=[length (mm)×width (mm)$^2$]/2. The efficacy parameters are the ΔT/ΔC, the mean percentage of regression, the partial and complete regressions (PR and CR) and the number of tumour-free mice at the end of the study (TFM).

The change in the volume of the tumours for each treated mouse (T) and control mouse (C) is calculated for each tumour by subtracting the volume of the tumour on the day of the start of the study from the volume of the tumour on the day of observation specified. The mean ΔT is calculated for the treated group and the mean ΔC is calculated for the control group. The ratio ΔT/ΔC is then calculated and expressed as a percentage: ΔT/ΔC=(delta T/delta C)×100.

A dose is regarded as being therapeutically active for a ΔT/ΔC of less than 40% and very active for a ΔT/ΔC of less than 10%. When the ΔT/ΔC is less than 0, the dose is regarded as highly active and the percentage of regression is then calculated (according to Plowman J., Dykes D. J., Hollingshead M., Simpson-Herren L. and Alley M. C., *Human tumor xenograft models in NCI drug development: Feibig H. H. B A, editor. Basel: Karger.;* 1999, pp. 101-125).

The percentage of tumour regression is defined as being the percentage of decrease in the tumour volume in the treated group on the day of observation specified in comparison with its volume on the first day of treatment. The percentage of tumour regression is calculated at a specific time t and for each animal. The mean percentage of regression is then calculated for the group.

$$\text{Percentage of regression (at time } t\text{)} = \frac{volume_{t0} - volume_t}{volume_{t0}} \times 100$$

Partial regression (PR): The regressions are defined as being partial when the decrease in the tumour volume reaches 50% of the volume of the tumour at the beginning of treatment.

Complete regression (CR): The complete regression is obtained when the volume of the tumour=0 mm$^3$ (a CR is regarded as being present when the volume of the tumour cannot be measured).

TFM: The tumour-free mice are defined as being mice not exhibiting a detectable tumour at the end of the study (beyond 100 days of treatment).

TABLE IV

Evaluation of the antitumour activity of the conjugates C1 and C2 on female SCID mice carrying an advanced human breast adenocarcinoma, MDA-MB-231

| Conjugate | Administration route/Dose in ml/kg by injection | Dose in µg/kg of tomaymycin dimer (mg prot/kg) | Day of administration | Mortality | Mean loss in weight in % at nadir (day) | Mean ΔT/ΔC in % (day) | Mean percentage of regression (day) | Regressions Partial | Regressions Complete | TFM (day 120) | Biological interpretation |
|---|---|---|---|---|---|---|---|---|---|---|---|
| C1 DAR 2.9 | IV 10 ml/kg | 80 (3.76) | 13 | 5/5 | — | — | — | — | — | — | Toxic |
| | | 40 (1.88) | | 0/5 | −9.6 (20) | 7 (28) | — | 3/5 | 0/5 | 0/5 | MTD, very active |
| | | 20 (0.94) | | 0/5 | −3.5 (30) | 13 (28) | — | 0/5 | 0/5 | 0/5 | Active |
| | | 10 (0.47) | | 0/5 | −1.1 (27) | 23 (28) | — | 0/5 | 0/5 | 0/5 | Active |
| C2 DAR 3.5 | IV 10 ml/kg | 80 (2.98) | 24 | 4/6 | — | — | — | — | — | — | Toxic |
| | | 40 (1.49) | | 0/6 | −5.0 (31) | <0 (46) | 96.2 (46) | 6/6 | 1/6 | 1/6 | MTD, highly active |
| | | 20 (0.75) | | 0/6 | −4.4 (31) | <0 (46) | 66.4 (46) | 4/6 | 0/6 | 0/6 | Highly active |
| | | 10 (0.37) | | 0/6 | −4.0 (31) | 14 (46) | — | 0/6 | 0/6 | 0/6 | Active |

Abbreviations:
MTD = Maximum Tolerated Dose,
TFM = Tumour-Free Mice at the end of the study According to a single-dose administration scheme, the highest dose tested for these two conjugates in this study (80 μg/kg) proved to be toxic, resulting in loss in weight and mortality.

At the MTD (40 μg/kg), C1 is very active and results in a loss in weight of 9.6% at nadir, a ΔT/ΔC of 7% and 3 PRs for 5 SCID mice. An antitumour activity was also observed at the lower doses of 20 and 10 μg/kg without resulting in PR.

At the MTD (40 μg/kg), C2 is highly active and results in a loss in weight of 5% at nadir and a tumour regression of 96.2% with 6 PRs for 6 mice, including 1 TFM. It is also very active at the lower dose of 20 μg/kg with a tumour regression of 66.4% and 4 PRs for 6 mice. An antitumour activity was also observed at the lowest dose of 10 μg/kg without, however, resulting in regression or PR.

In conclusion, it is found that C2 exhibits a strong anticancer activity and showed a better activity than C1 with a tumour regression, PR and TFM at the MTD which are not observed with C1 at the same doses.

The invention claimed is:

1. A compound of according to formula (I):

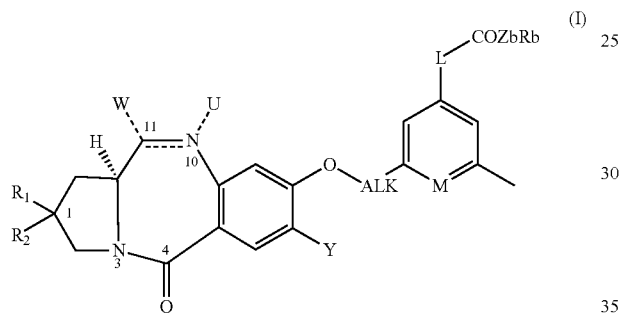

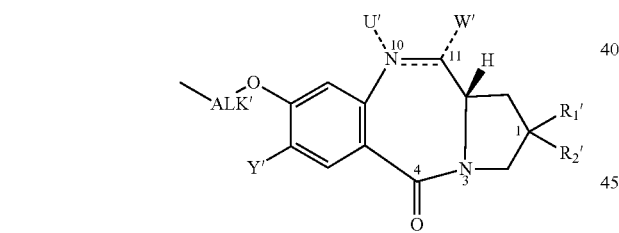

wherein:
- ≈≈≈ represents a single bond or a double bond,
- $R_1$ and $R_2$, which are identical or different, represent, independently of one another: H, Hal or a ($C_1$-$C_6$)alkyl group option any substituted by one or more substituent(s) chosen from Hal, CN, NRR', CF, OR, an aryl or heteroaryl group, or S(O)$_q$R with q=0, 1 or 2; or $R_1$ and $R_2$ together form a double bond =$CH_2$ or =CH—$CH_3$;
- $R_1'$ and $R_2'$, which are identical or different, represent, independently of one another: H, Hal or a ($C_1$-$C_6$)alkyl group optionally substituted by one or more substituent(s) chosen from: Hal, CN, NRR', $CF_3$, OR an aryl or heteroaryl group, or S(O)$_q$R with q=0, 1 or 2 or $R_1'$ and $R_2'$ together form a double bond =$CH_2$ or =CH—$CH_3$;
- Y and Y', which are identical or different, represent, independently of one another, H or OR;
- M represents CH or N;
- ALK and ALK', which are identical or different, represent, independently of one another, a ($C_1$-$C_6$)alkylene group;
- R and R' represent, independently of one another, H or a ($C_1$-$C_6$)alkyl or aryl group optionally substituted by one or more substituent(s) chosen from: Hal, CN, NRR', $CF_3$, OR or an aryl or heteroaryl group;
- L represents an -$L_1$-$L_2$- group, wherein:
  - $L_1$ is attached to the aromatic ring comprising M via the ALK or OALK group and represents one of the following groups:

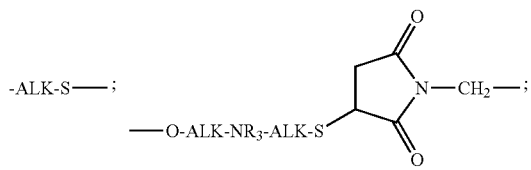

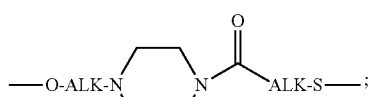

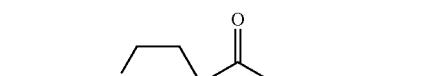

and $L_2$ represents the —$CH_2$C(=O)—$NR_3$—($CH_2CH_2$O),-ALK- group attached to $L_1$ via —$CH_2$C(=O)—; or L represents the —O-ALK-$NR_3$-ALK-S—($CH_2CH_2$O)-ALK- group attached to the aromatic ring comprising M via the OALK group;

- $R_3$ represents H or a ($C_1$-$C_6$)alkyl group;
- I represents an integer ranging from 1 to 40, and
- $Z_b$ represents a single bond, —O— or —NH— and $R_b$ represents H or a ($C_1$-$C_6$)alkyl, ($C_3$-$C_7$)-cycloalkyl, aryl, heteroaryl or ($C_3$-$C_7$)heterocycloalkyl group;
- or $Z_b$ represents a single bond and $R_b$ represents Hal;

provided that when ≈≈≈ represents a single bond, then:
- ---- represents a single bond;
- U and U' each is H; and
- W and W', which are identical or different, each represents, independently of one another, —OH, OR, —OCOR, —COOR, —OCOOR, —OCONRR', a cyclic carbamate such that N10 and C11 are included in a ring, —NRCONRR', —OCSNHR, a cyclic thiocarbamate such that N10 and C11 are included in a ring, —SH, —SR, —SOR, —SOOR, —NRSOOR', —NRR', a cyclic amine such that N10 and C11 are included in a ring, —NROR', —NRCOR', —$N_3$, —CN, Hal or a trialkylphosphonium or triarylphosphonium group;

or a pharmaceutically acceptable salt thereof.

2. A compound according to claim 1, wherein said compound according to formula:

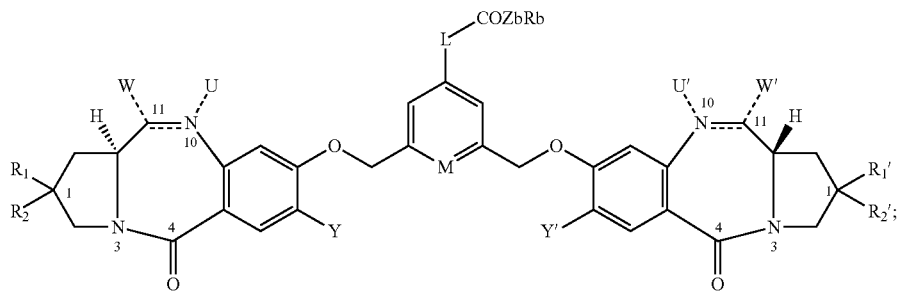

or a pharmaceutically acceptable salt thereof.

3. A compound according to claim 1, wherein said compound is according to formula (IA) or (IB):

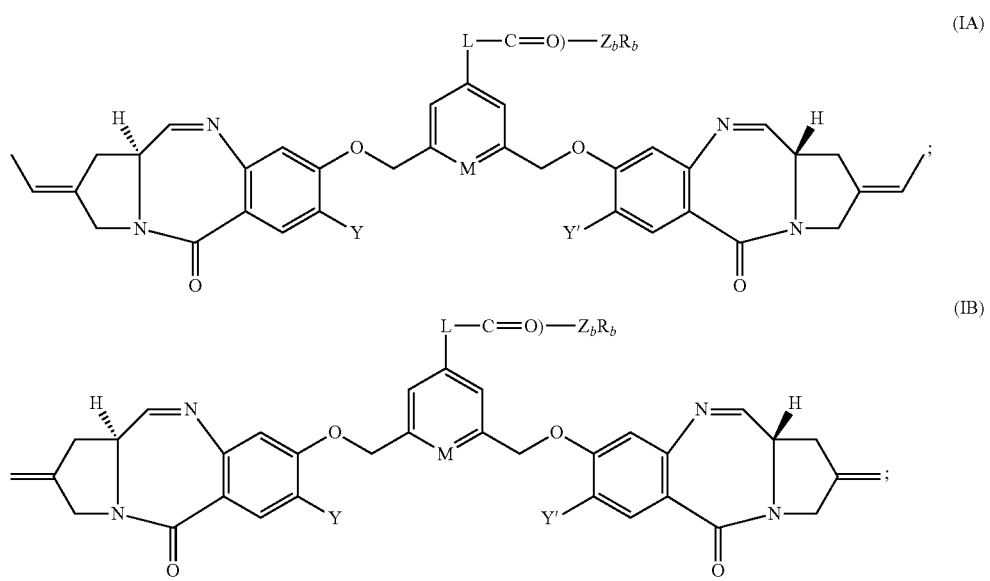

or a pharmaceutically acceptable salt thereof.

4. A compound according to claim 1, wherein each of Y and Y' represent, independently, a $(C_1\text{-}C_4)$alkoxy group, more particularly a methoxy group; or a pharmaceutically acceptable salt thereof.

5. A compound according to claim 1, wherein L is:

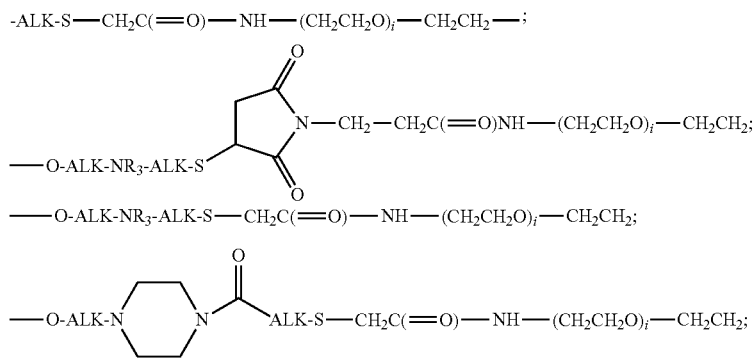

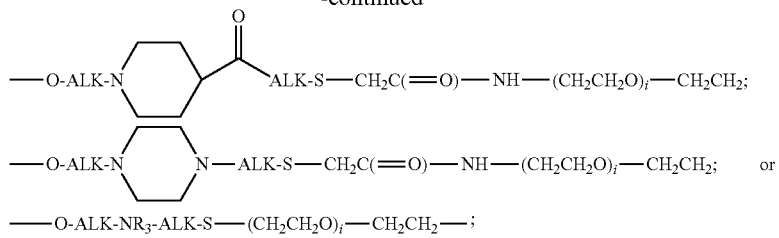
or a pharmaceutically acceptable salt thereof.
6. A compound according to claim 1, wherein L is:
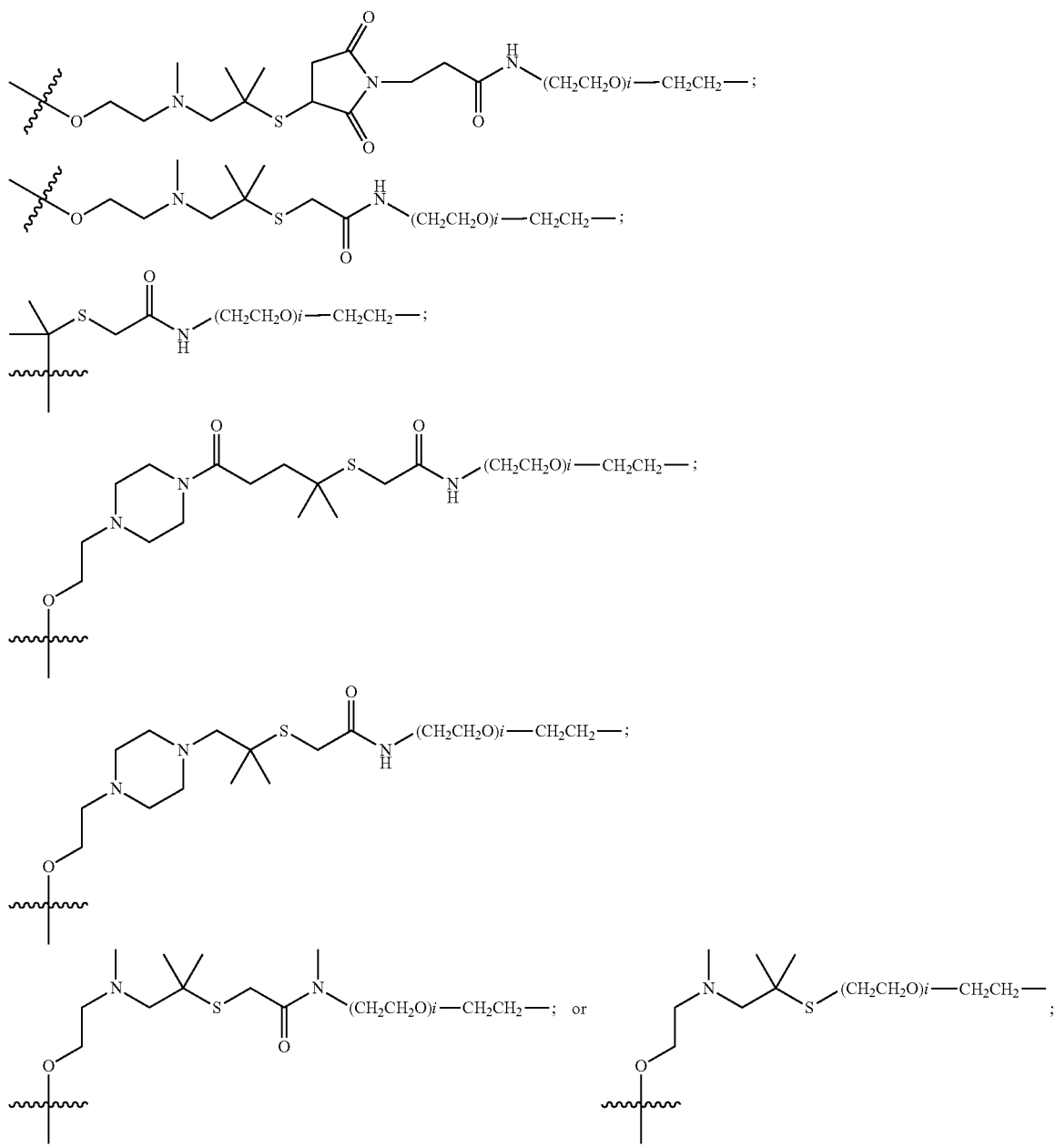
or a pharmaceutically acceptable salt thereof.

7. A compound according to claim 1, wherein L is:
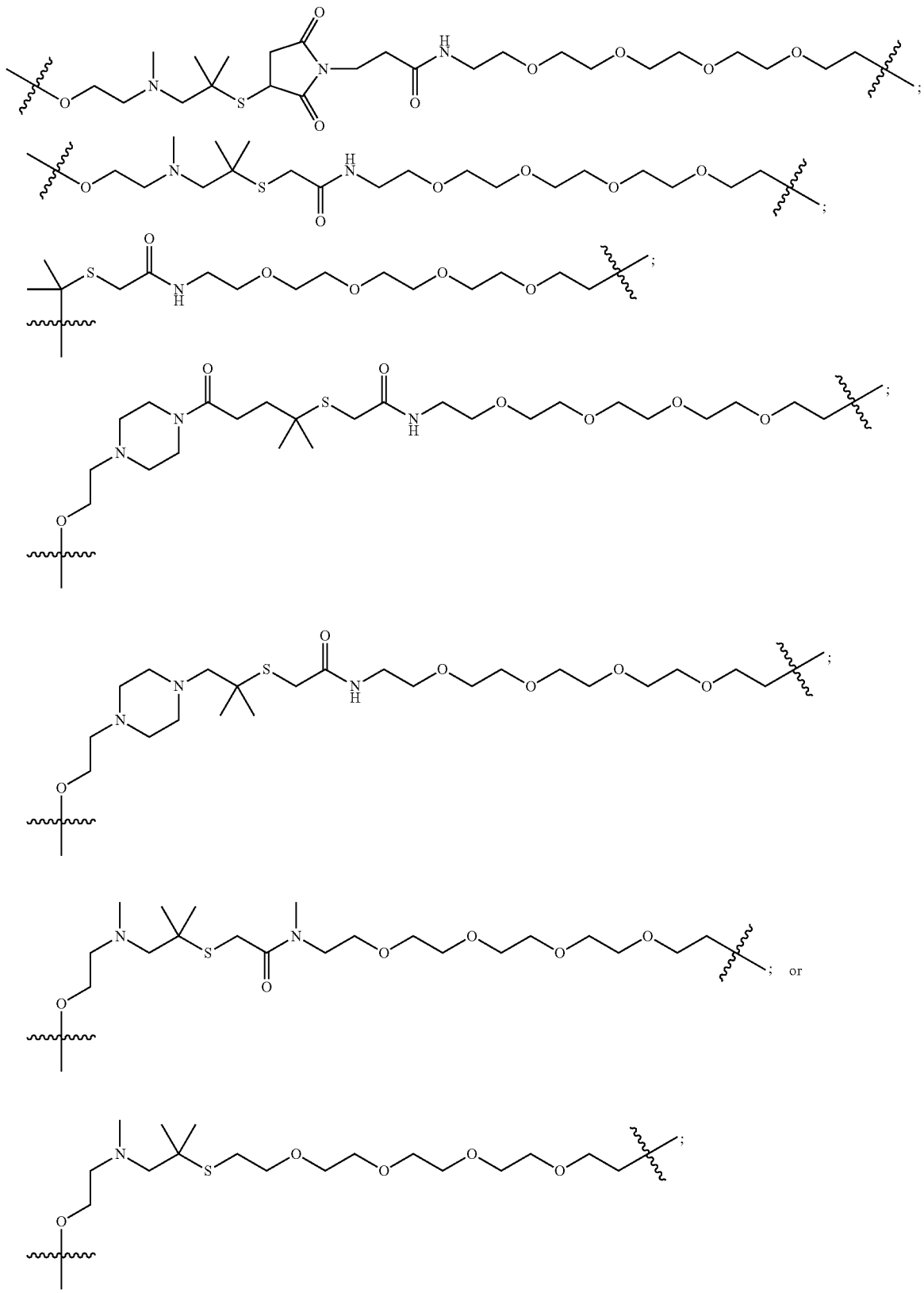
or a pharmaceutically acceptable salt thereof.

8. A compound according to claim 1, wherein —COZ$_b$R$_b$ represents —COOH, —COO(C$_1$-C$_6$)alkyl, —COOCH$_3$, —COOCH$_2$CH=CH$_2$,
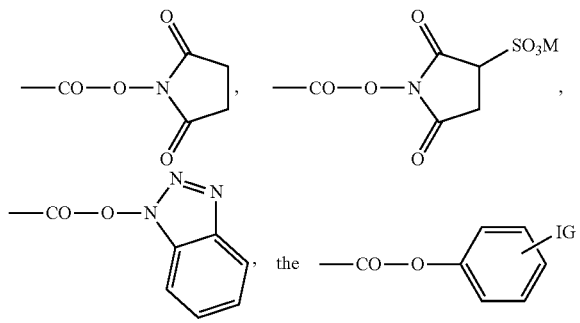
M = H or cation
the —CO—O—⟨aryl⟩—IG group, in which IG represents at least one inductive group, more particularly
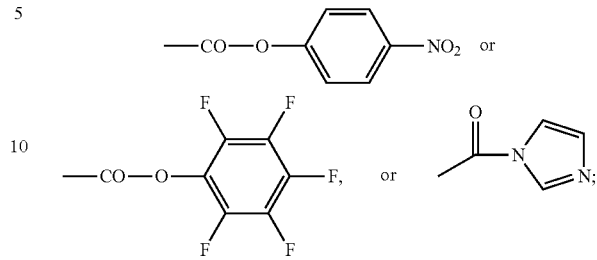
or a pharmaceutically acceptable salt thereof.
9. A compound according to claim 1, wherein said compound is:
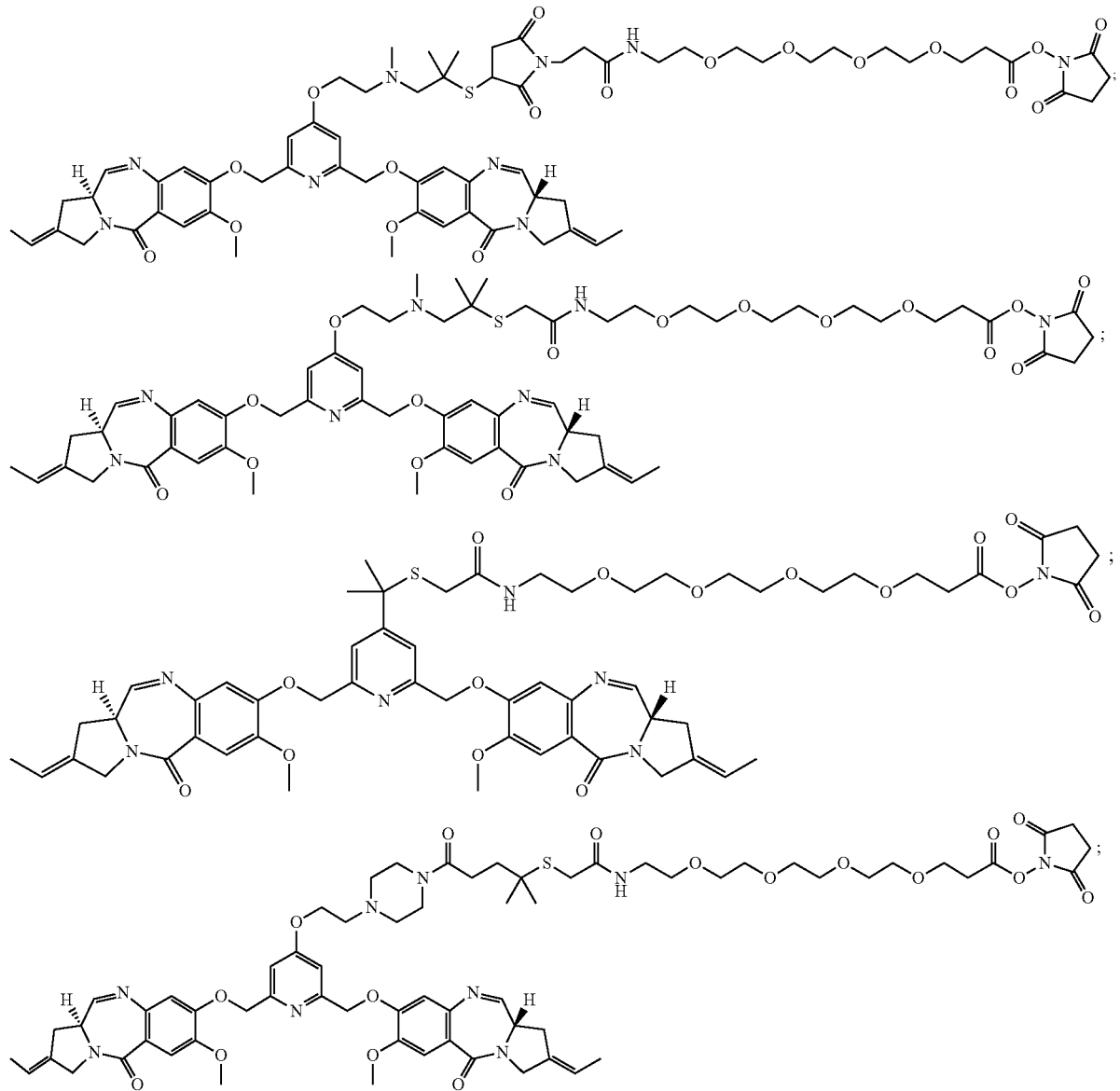

-continued
or

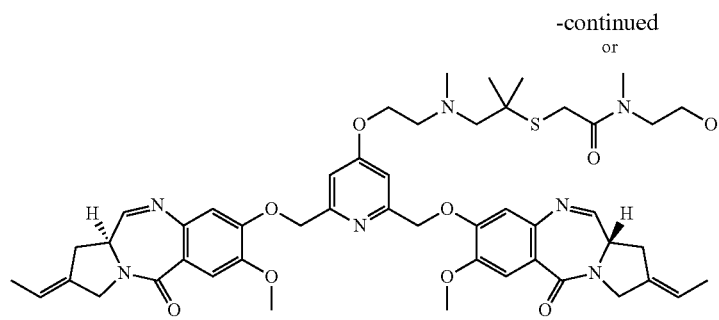;

or a pharmaceutically acceptable salt thereof.

10. Pharmaceutical composition comprising a compound according to claim 1 or a pharmaceutically acceptable salt thereof and at least one excipient.

11. A compound according to claim 1, wherein l represents an integer ranging from 1 to 20; or a pharmaceutically acceptable salt thereof.

12. A compound according to claim 1, wherein represents an integer ranging from 1 to 10;
or a pharmaceutically acceptable salt thereof.

13. A compound according to claim 4, wherein each of Y and Y' represent a methoxy group;
or a pharmaceutically acceptable salt thereof.

* * * * *